US010195281B2

(12) United States Patent
Benedict et al.

(10) Patent No.: US 10,195,281 B2
(45) Date of Patent: Feb. 5, 2019

(54) ANTIBODY FORMULATIONS AND USES THEREOF

(71) Applicant: Tracon Pharmaceuticals, Inc., San Diego, CA (US)

(72) Inventors: Suzanne Benedict, Carlsbad, CA (US); Mark Cornell Manning, Johnstown, CO (US); Brian M. Murphy, Fort Collins, CO (US); Sharon Real, San Diego, CA (US); Charles Theuer, San Diego, CA (US)

(73) Assignee: Tracon Pharmaceuticals, Inc., San Diego, CA (US)

( * ) Notice: Subject to any disclaimer, the term of this patent is extended or adjusted under 35 U.S.C. 154(b) by 476 days.

(21) Appl. No.: 14/421,108

(22) PCT Filed: Sep. 5, 2013

(86) PCT No.: PCT/US2013/058265
§ 371 (c)(1),
(2) Date: Feb. 11, 2015

(87) PCT Pub. No.: WO2014/039682
PCT Pub. Date: Mar. 13, 2014

(65) Prior Publication Data
US 2015/0209430 A1 Jul. 30, 2015

Related U.S. Application Data

(60) Provisional application No. 61/697,111, filed on Sep. 5, 2012.

(51) Int. Cl.
| | |
|---|---|
| *A61K 39/395* | (2006.01) |
| *A61K 47/22* | (2006.01) |
| *C07K 16/28* | (2006.01) |
| *A61K 9/00* | (2006.01) |
| *A61K 47/26* | (2006.01) |
| *A61K 47/12* | (2006.01) |
| *C07K 16/30* | (2006.01) |
| *A61K 47/18* | (2017.01) |
| *A61K 9/08* | (2006.01) |
| *A61K 39/00* | (2006.01) |

(52) U.S. Cl.
CPC ............ *A61K 47/22* (2013.01); *A61K 9/0019* (2013.01); *A61K 9/0048* (2013.01); *A61K 47/12* (2013.01); *A61K 47/26* (2013.01); *C07K 16/2863* (2013.01); *C07K 16/2896* (2013.01); *C07K 16/30* (2013.01); *A61K 9/08* (2013.01); *A61K 47/183* (2013.01); *A61K 2039/505* (2013.01); *C07K 2317/52* (2013.01); *C07K 2317/56* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 928,641 | A | 7/1909 | Edmunds |
| 4,472,509 | A | 9/1984 | Gansow et al. |
| 4,683,202 | A | 7/1987 | Mullis |
| 4,816,567 | A | 3/1989 | Cabilly et al. |
| 4,868,103 | A | 9/1989 | Stavrianopoulos et al. |
| 4,938,948 | A | 7/1990 | Ring et al. |
| 5,021,236 | A | 6/1991 | Gries et al. |
| 5,391,377 | A | 2/1995 | Barnwell |
| 5,530,101 | A | 6/1996 | Queen et al. |
| 5,631,169 | A | 5/1997 | Lakowicz et al. |
| 5,756,097 | A | 5/1998 | Landucci et al. |
| 5,796,097 | A | 8/1998 | Lawrence |
| 5,928,641 | A | 7/1999 | Seon |
| 6,096,289 | A | 8/2000 | Goldenberg |
| 6,096,871 | A | 8/2000 | Presta et al. |
| 6,190,660 | B1 | 2/2001 | Seon |
| 6,200,566 | B1 | 3/2001 | Seon |
| 6,267,958 | B1 * | 7/2001 | Andya ...................... 424/130.1 |
| 6,350,861 | B1 | 2/2002 | Co et al. |
| 6,407,213 | B1 | 6/2002 | Carter et al. |
| 6,610,293 | B1 | 8/2003 | Fischer et al. |
| 6,737,056 | B1 | 5/2004 | Presta |
| 6,881,557 | B2 | 4/2005 | Foote |

(Continued)

FOREIGN PATENT DOCUMENTS

| | | |
|---|---|---|
| CN | 101084015 A | 12/2007 |
| CN | 102414221 A | 4/2012 |

(Continued)

OTHER PUBLICATIONS

Altman et al., "The American College of Rheumatology criteria for the classification and reporting of osteoarthritis of the hip," Arthritis Rheum. 34:505-514 (1991).
Altschul et al., "Basic Local Alignment Search Tool," J. Mol. Biol. 215:403-410 (1990).
Altschul et al., "Gapped BLAST and PSI-BLAST: a new generation of protein database search programs," Nucl. Acids. Res. 25(17):3389-3402 (1997).
Antitope, "Meeting Report" 5th Annual Monoclonal Antibodies Conference, Aug. 2000, pp. 308-317.

(Continued)

*Primary Examiner* — Yunsoo Kim
(74) *Attorney, Agent, or Firm* — Wilson Sonsini Goodrich & Rosati

(57) ABSTRACT

The present application relates to formulations of anti-CD105 antibodies, antigen-binding fragments thereof, and uses thereof. Another aspect relates to pre-filled syringes of the formulations of anti-CD105 antibodies or antigen-binding fragments thereof. Another aspect relates to the use of the formulations to reduce one or more signs or symptoms of an angiogenesis-related disorder such as cancers and ophthalmologic diseases.

36 Claims, 2 Drawing Sheets
Specification includes a Sequence Listing.

(56) References Cited

U.S. PATENT DOCUMENTS

| | | | |
|---|---|---|---|
| 7,091,321 | B2 | 8/2006 | Gillies et al. |
| 7,097,836 | B1 | 8/2006 | Seon |
| 7,112,412 | B1 | 9/2006 | Bander |
| 7,115,716 | B2 | 10/2006 | Watkins |
| 7,217,798 | B2 | 5/2007 | Hinton et al. |
| 8,092,803 | B2 | 1/2012 | Furfine et al. |
| 8,110,546 | B2 | 2/2012 | Dix et al. |
| 8,221,753 | B2 | 7/2012 | Theuer |
| 8,609,094 | B2 | 12/2013 | Theuer et al. |
| RE45,499 | E | 4/2015 | Schneider et al. |
| 9,518,122 | B2 | 12/2016 | Theuer et al. |
| 9,926,375 | B2 | 3/2018 | Theuer |
| 2002/0136725 | A1 | 9/2002 | Blackburn et al. |
| 2003/0003048 | A1 | 1/2003 | Li et al. |
| 2003/0129193 | A1 | 7/2003 | Thorpe |
| 2003/0185832 | A1 | 10/2003 | Thorpe et al. |
| 2004/0023313 | A1 | 2/2004 | Boyle |
| 2004/0033228 | A1 | 2/2004 | Krause et al. |
| 2004/0175756 | A1 | 9/2004 | Kolkman et al. |
| 2005/0037421 | A1 | 2/2005 | Honda et al. |
| 2005/0048512 | A1 | 3/2005 | Kolkman et al. |
| 2005/0053973 | A1 | 3/2005 | Kolkman et al. |
| 2005/0089932 | A1 | 4/2005 | Kolkman et al. |
| 2005/0164301 | A1 | 7/2005 | Kolkman et al. |
| 2005/0221384 | A1 | 10/2005 | Kolkman et al. |
| 2005/0238646 | A1 | 10/2005 | Ledbetter et al. |
| 2006/0147379 | A1 | 7/2006 | Bornhop |
| 2006/0223096 | A1 | 10/2006 | Umana et al. |
| 2006/0292643 | A1 | 12/2006 | Goletz et al. |
| 2007/0008238 | A1 | 1/2007 | Liu et al. |
| 2007/0065437 | A1 | 3/2007 | Elson et al. |
| 2007/0071761 | A1 | 3/2007 | Seon |
| 2007/0072797 | A1 | 3/2007 | Robinson et al. |
| 2007/0077310 | A1 | 4/2007 | Zemel et al. |
| 2007/0082380 | A1 | 4/2007 | Pardridge et al. |
| 2008/0199464 | A1 | 8/2008 | Plowman et al. |
| 2009/0142343 | A1 | 6/2009 | Fuh et al. |
| 2010/0015157 | A1 | 1/2010 | Andya et al. |
| 2010/0098692 | A1 | 4/2010 | Theuer et al. |
| 2011/0076263 | A1 | 3/2011 | Theuer et al. |
| 2012/0244147 | A1 | 9/2012 | Theuer et al. |
| 2012/0294864 | A1 | 11/2012 | Theuer et al. |
| 2014/0234319 | A1 | 8/2014 | Kapur et al. |
| 2014/0314742 | A1 | 10/2014 | Theuer |
| 2016/0009811 | A1 | 1/2016 | Theuer et al. |
| 2016/0257755 | A1 | 9/2016 | Theuer |
| 2017/0335005 | A1 | 11/2017 | Theuer |
| 2018/0057602 | A1 | 3/2018 | Theuer et al. |

FOREIGN PATENT DOCUMENTS

| | | |
|---|---|---|
| CN | 104788562 A | 7/2015 |
| EP | 0404097 A2 | 12/1990 |
| EP | 0404097 A2 | 10/1991 |
| EP | 0404097 A3 | 9/1996 |
| EP | 2892559 A1 | 7/2015 |
| JP | 2000-511425 A | 5/1997 |
| JP | 2010506911 A | 3/2010 |
| JP | 2010536786 A | 12/2010 |
| WO | WO 93/11161 A1 | 6/1993 |
| WO | WO 97/45450 A1 | 12/1997 |
| WO | WO-9856418 A1 | 12/1998 |
| WO | WO-0042012 A1 | 7/2000 |
| WO | WO-0230463 A2 | 4/2002 |
| WO | WO 02/069232 A2 | 9/2002 |
| WO | WO-02072824 A2 | 9/2002 |
| WO | WO-02069232 A3 | 2/2003 |
| WO | WO-03068260 A1 | 8/2003 |
| WO | WO-03070234 A1 | 8/2003 |
| WO | WO 2008/038127 A | 4/2008 |
| WO | WO-2008045373 A2 | 4/2008 |
| WO | WO 2008/154351 | 12/2008 |
| WO | WO 2009/033581 A | 3/2009 |
| WO | WO 2009/091810 | 7/2009 |
| WO | WO 2010/039873 | 4/2010 |
| WO | WO-2010039875 A2 | 4/2010 |
| WO | WO-2010066762 A1 | 6/2010 |
| WO | WO-2010102241 A1 | 9/2010 |
| WO | WO 2011/022339 | 2/2011 |
| WO | WO 2010/032059 | 4/2011 |
| WO | WO 2011/041441 | 4/2011 |
| WO | WO-2012003470 A2 | 1/2012 |
| WO | WO-2012145539 A1 | 10/2012 |
| WO | WO-2013019805 A1 | 2/2013 |
| WO | WO-2014039682 A1 | 3/2014 |
| WO | WO-2015042269 A1 | 3/2015 |
| WO | WO-2016077451 A1 | 5/2016 |

OTHER PUBLICATIONS

Argarana et al., "Molecular cloning and nucleotide sequences of the streptavidin gene," Nucl. Acids Res. 14(4):1871-1882 (1986).
Baker, et al. "Identification and Removal of Immunogenicity in Therapeutic Proteins." Current Opinion in Drug Discovery and Development, vol. 10, No. 2, Jan. 1, 2007, pp. 219-227.
Bernebeu et al., "Novel biochemical pathways of endoglin in vascular cell physiology," J. Cell Biochem. 102(6):1375-1388 (2007).
Bird et al., "Single-chain antigen-binding proteins," Science 242:423-426 (1988).
Blood et al., "Tumor interactions with the vasculature: angiogenesis and tumor metastasis," Biochim. Biophys. Acta 1032:89-118 (1990).
Bockhorn, et al. "Differential Vascular and Transcriptional Responses to Anti-Vascular Endothelial Growth Factor Antibody in Orthotopic Human Pancreatic Cancer Xenografts." Clinical Cancer Research: An Official Journal of the American Association for Cancer Research, vol. 9, No. 11, Sep. 15, 2003, pp. 4221-4226.
Bonnet & Walsh, "Osteoarthritis, angiogenesis and inflammation," Rheumotol. 44:7-16 (2005).
Brooks et al., "Insulin-like Growth Factor Receptor Coordinates With Integrin at)/35 to Promote Tumor Cell Dissemination In Vivo," J. Clin. Invest. 99:1390-1398 (1997).
Burrows, et al. Up-regulation of endoglin on vascular endothelial cells in human solid tumors: implications for diagnosis and therapy. Clin Cancer Res. Dec. 1995;1(12):1623-34.
Carillo and Lipman, "The Multiple Sequence Alignment Problem in Biology," SIAM J. Appl. Math 48(5):907-1082 (1988).
Chad and Chamow, "Therapeutic antibody expression technology," Curr Opin Biotechnol. Apr. 2001;12(2):188-94.
Chidlow et al., "Pathogenic angiogenesis in IBD and experimental colitis: new ideas and therapeutic avenues," Am. J. Physiol. Gastrointest. Liver Physiol. 293:5-18 (2007).
Chothia, et al. Canonical structures for the hypervariable regions of immunoglobulins. J Mol Biol. 1987 196(4):901-17.
Clackson et al., "Making antibody fragments using phage display libraries," Nature 352:624-628 (1991).
D'Amato et al. Thalidomide is an inhibitor of angiogenesis. PNAS 91:4082-4085 (1994).
Davis, et al."Regional effects of an antivascular endothelial growth factor receptor monoclonal antibody on receptor phosphorylation and apoptosis in human 253J B-V bladder cancer xenografts." Cancer Research, vol. 64, No. 13, Jul. 1, 2004, pp. 4601-4610.
Derbalian et al., "Fluorescein labeling of fab while preserving single thiol," Anal. Biochem. 173:59-63 (1988).
Devereux et al., "A comprehensive set of sequence analysis programs for the VAX," Nucl. Acids Res. 12(1):387-395 (1984).
Dobeli et al., "Recombinant Fusion Proteins for the Industrial Production of Disulfide Bridge Containing Peptides: Purification, Oxidation without Concatamer Formation, and Selective Cleavage," Protein Expression and Purification 12(3):404-414 (1998).
Duff, et al. CD105 is important for angiogenesis: evidence and potential applications. FASEB J. Jun. 2003;17(9):984-92.
Edge, "Total synthesis of a human leukocyte interferon gene," Nature 292:756-762 (1981).
Fix et al., "Oral controlled release technology for peptides: status and future prospects," Pharm Res. 13:1760-1764 (1996).
Francis, et al. PEGylation of cytokines and other therapeutic proteins and peptides: the importance of biological optimisation of coupling techniques. Int J Hematol. Jul. 1998;68(1):1-18.

(56) References Cited

OTHER PUBLICATIONS

Furstenberger et al., "Insulin-like growth factors and cancer," Lancet Oncol. 3:298-302 (2002).
Gao, et al., Cross linked polyacrylamide coating for capillary isoelectric focusing. Anal Chem 2004, 76(24), 7179-7186.
Ghetie et al., "Immunotoxins in the therapy of cancer: from bench to clinic," Pharmacol. Ther. 63:209-234 (1994).
Gigli, et al. The stoichiometric measurement of the serum inhibition of the first component of complement by the inhibition of immune hemolysis. J Immunol. Jun. 1968;100(6):1154-64.
Gilles et al., "Stability of water-soluble carbodiimides in aqueous solution," Anal. Biochem. 184(2):244-248 (1990).
Glazer et al., "Emerging Techniques: Phycofluor probes," Trends Biochem. Sci. 9:423-427 (1984).
Gougos and Letarte, "Identification of a human endothelial cell antigen with monoclonal antibody 44G4 produced against a pre-B leukemic cell line," J. Immunol. 141:1925-1933 (1988).
Gougos and Letarte, "Primary Structure of Endoglin, an RGD-containing Glycoprotein of Human Endothelial Cells," J. Biol. Chem. 265:8361-8364 (1990.
Green, "A spectrophotometric assay for avidin and biotin based on binding of dyes by avidin," Biochem J. 94:23c-24c (1965).
Green, "Avidin" in Advances in Protein Chemistry, Academic Press, New York 39:85-133 (1975).
Green, "The use of bifunctional biotinyl compounds to determine the arrangement of subunits in avidin," Biochem J. 125:781-791 (1971).
Greenberg et al., "Characteristics of the Effector Cells Mediating Cytotoxicity Against Antibody-Coated Target Cells," Immunol. 21:719 (1975).
Hardy et al., "Demonstration of B-cell maturation in X-linked immunodeficient mice by simultaneous three-colour immunofluorescence," Nature 306:270-272 (1983).
Hardy et al., "Murine B Cell Differentiation Lineages," J. Exp. Med. 159:1169-1188 (1984).
Haruta and Seon, "Distinct human leukemia-associated cell surface glycoprotein GP160 defined by monoclonal antibody SN6," PNAS 83:7898-7902 (1986).
Haywood, et al. Inflammation and angiogenesis in osteoarthritis. Arthritis & Rheumatism. 2003; 48(8): 2173-2177.
Heeley, "Mutations flanking the polyglutamine repeat in the modultory domain of rat glucocorticoid receptor lead to an increase in affinity for hormone," Endocr. Res. 28:217-229 (2002).
Henikoff et al., "Amino acid substitution matrices from protein blocks," PNAS USA 89:10915-10919 (1992).
Holliger et al., "Diabodies: Small bivalent and bispecific antibody fragments," PNAS USA 90:6444-6448 (1993).
Houck, et al. The vascular endothelial growth factor family: identification of a fourth molecular species and characterization of alternative splicing of RNA. Mol Endocrinol. Dec. 1991;5(12):1806-14.
Huston et al., "Protein engineering of antibody binding sites: Recovery of specific activity in an anti-digoxin single-chain Fv analogue produced in *Escherichia coli*," PNAS USA 85:5879-5883 (1988).
International seach report and written opinion dated Nov. 23, 2010 for PCT/US2010/045651.
International preliminary report on patentability dated Apr. 14, 2011 for PCT/US2009/059086.
International search report and written opinion dated Aug. 18, 2010 for PCT/US2009/059086.
International preliminary report on patentability dated Apr. 3, 2012 for PCT/US2010/050759.
International search report and written opinion dated Feb. 23, 2011 for PCT/US2010/050759.
International preliminary report on patentability dated Mar. 19, 2015 for PCT/US2013/058265.
International Search Report dated Oct. 14, 2013 for PCT/US2013/058265.
Written Opinion dated Oct. 14, 2013 for PCT/US2013/058265.

Jay, "Chemical Synthesis of a Biologically Active Gene for Human Immune Interferon-y," J. Biol. Chem. 259:6311-6317 (1984).
Jeong, et al., Avimers hold their own. Nat Biotechnol. Dec. 2005;23(12):1493-4.
Jones and Segal, "Antibody-Dependent Cell Mediated Cytolysis (ADCC) with Antibody-Coated Effectors: New Methods for Enhancing Antibody Binding and Cytolysis," J. Immunol. 125:926-933 (1980).
Jones et al., "Replacing the complementarity-determining regions in a human antibody with those from a mouse," Nature 321:522-525 (1986).
Jones et al., Analysis of polypeptides and proteins. Adv. Drug Delivery Rev. 10: 29-90 (1993).
Journal of Clinical Oncology,2009 ASCO Annual Meeting Proceedings(Post-Meeting Edition)., May 20, 2009, vol. 27, No. 15S, 3518.
Kabat et al., Sequences of Proteins in Immunological Interest, 5th ed., Public Health Service, National Institute of Health, Bethesda MD 1991, pp. 647-669.
Kim et al., "Three-dimensional in vitro tissue culture models of breast cancer—a review," Breast Cancer Research Treatment 85(3):281-291 (2004).
Koch and Distler, "Vaculopathy and disordered angiogenesis in selected rheumatic diseases: rheumatoid arthritis and systemic sclerosis," Arthritis Res. and Ther. 9(Supp.2):1-9 (2007).
Kohler and Milstein, "Continuous cultures of fused cells secreting antibody of predefined specificity," Nature 256:495-497 (1975).
Kroll et al., "A Multifunctional Prokaryotic Protein Expression System: Overproduction, Affinity Purification, and Selective Detection," DNA Cell Biol. 12:441-453 (1993).
Kronick et al., "Immunoassay Techniques with Fluorescent Phycobiliprotein Conjugates," Clin. Chem. 29:1582-1586 (1983).
Kronick et al., "The use of phycobiliproteins as fluorescent labels in immunoassay," J. Immunol Meth. 92:1-13 (1986).
Lahn et al., "Aerosolized Anti-T-Cell-Receptor Antibodies Are Effective against Airway Inflammation and Hyperreactivity," Int. Arch. Allergy Immunol. 134:49-55 (2004).
Lanier et al, "Human Lymphocyte Subpopulations Identified by Using Three-Color Immunofluorescence and Flow Cytometry Analysis: Correlation of Leu-2, Leu-3, Leu¬7, Leu-8, and Leu-11 Cell Surface Antigen Expression," J. Immunol 132:151-156 (1984).
Leatherbarrow et al., "Effector functions of a monoclonal aglycosylated mouse IgG2a: binding and activation of complement component Cl and interaction with human monocyte Fc receptor," Mol. Immunol. 22(4):407-415 (1985).
Leung, et al. Vascular endothelial growth factor is a secreted angiogenic mitogen. Science. Dec. 8, 1989;246(4935):1306-9.
Liljeblad, et al. Analysis of agalacto-IgG in rheumatoid arthritis using surface plasmon resonance. Glycoconj J. May 2000;17(5):323-9.
Lowe et al., Aggregation, stability and formulation of human antibody therapeutics, Advances I Protein Chemistry and Structural Biology, 84:41-61, 2011.
Mack, et al., A systematic study in CIEF: Defining and optimizing experimental parameters critical to method reproducibility and robustness. Electrophoresis 2009, 30 (23), 4049-4058.
MacKay et al., "Effect on Natural Killer and Antibody-Dependent Cellular Cytotoxicity of Adjuvant Cytotoxic .Chemotherapy Including Melphalan in Breast Cancer," Cancer Immunol. Immunother. 16:98-100 (1983).
MacLennan, "Competition for Receptors for Immunoglobulin on Cytotoxic Lymphocytes," Clin. Exp. Immunol. 10:275 (1972).
Maio et al., "Is it the primetime for endoglin (CD105) in the clinical setting?" Cardiovascular Research 69(4):781-783 (2006).
Marks et al., "By-Passing Immunization Human Antibodies from V-gene Libraries Displayed on Phage," J. Mol. Biol. 222:581-597 (1991).
Matsuno, et al. "Induction of Lasting Complete Regression of Preformed Distinct Solid Tumors by Targeting the Tumor Vasculature Using Two New Anti-Endoglin Monoclonal Antibodies." Clinical Cancer Research, vol. 5, No. 2, Feb. 1, 1999m pp. 371-382.

(56) References Cited

OTHER PUBLICATIONS

Montesano et al., "In Vitro Rapid Organization of Endothelial Cells into Capillary-like Networks Is Promoted by Collagen Matrices," J. Cell Biol. 97:1648-1652 (1983).
Muraoka, et al. Structural requirements for IgM assembly and cytolytic activity. Effects of mutations in the oligosaccharide acceptor site at Asn402. J Immunol. Jan. 15, 1989;142(2):695-701.
Muyldermans et al., "Sequence and structure of Vh domain from naturally occurring camel heavy chain immunoglobulins lacking light chains," Protein Engineering 7(9):1129-1135 (1994).
Nakajima et al., "Mechanism of amide formation by carbodiimide for bioconjugation in aqueous media," Bioconjugate Chem. 6(1):123-130 (1995).
Nambiar, et al. Total synthesis and cloning of a gene coding for the ribonuclease S protein. Science. Mar. 23, 1984;223(4642):1299-301.
Nilsson et al., "p-Tolueneslfonyl chloride as an activating agent of agarose for the preparation of immobilized affinity ligands and proteins," Eur. J. Biochem. 112:397-402 (1980).
Nolan-Stevaux et al., Endoglin requirement for BMP9 signaling in endothelial cells reveals new mechanism of action for selective anti-endoglin antibodies. PLOS One, 7(12): e50920. doi:10.1371/journal.pone.0050920.
Noren et al., "A general method for site-specific incorporation of unnatural amino acids into proteins," Science 244:182-188 (1989).
Osbourn et al., "Directed selection of MIP-Ia neutralizing CCR5 antibodies from a phage display human antibody library," Nat. Biotech. 16:778-781 (1998).
Pahler et al., "Characterization and Crystallization of Core Streptavidin," J. Biol. Chem. 262:13933-13937 (1987).
Parks et al., "Three-Color Immunofluorescence Analysis of Mouse B-Lymphocyte Subpopulations," Cytometry 5:159-168 (1984).
Perry, et al. "New Approaches to Prediction of Immune Responses to Therapeutic Proteins during Preclinical Development." Drugs in R & D, vol. 9, No. 6, Jan. 1, 2008, pp. 386-396.
Pinals et al., "Preliminary criteria for clinical remission in rheumatoid arthritis," Arthritis Rheum. 24:1308 (1981).
Pluckthun, "Antibodies from *Escherichia coli*," in Handbook of Experimental Pharmacology;The Pharmacology of Monoclonal Antibodies; vol. 113, pp. 269-315 (1994), Rosenburg and Moore eds., Springer-Verlag, New York.
Pluckthun, "Antibody engineering: advances from the use of *Escherichia coli* expression systems," Biotech. 9:545-551 (1991).
Presta, "Antibody engineering," Curr. Op. Struct. Biol. 2:593-596 (1992).
Presta, et al. Humanization of an anti-vascular endothelial growth factor monoclonal antibody for the therapy of solid tumors and other disorders. Cancer Res. Oct. 15, 1997;57(20):4593-9.
Raff, "High-level production of recombinant immunoglobulins in mammalian cells," Curr. Op. Biotech. 4:573-576 (1993).
Reichmann et al., "Reshaping human antibodies for therapy," Nature 332:323-327 (1988).
Reiter et al., "Engineering antibody Fv fragments for cancer detection and therapy: Bisulfide-stabilized Fv fragments," Nature Biotech. 14:1239-1245 (1996).
Rosen et al., "Early Evidence of Tolerability and Clinical activity from a Phase 1 Study OFTRC105 (Anti-CD105 Antibody) in Patients with Advanced Refractory Cancer." 2009 ASCO Annual Meeting.
Rosen, et al. Early evidence of tolerability and clinical activity from a phase 1 study of TRC105 (anti-CD105 antibody) in patients with advanced refractory cancer, EORTC-NCI-AACR symposium on molecular targets and cancer therapeutics, Geneva, Switzerland, Oct. 21-24, 2008, EJC supplements. 2008; 6(12): 126: poster 400.
Roy-Chaudhury et al., "Endoglin, a transforming growth factor-beta-binding protein, is upregulated in chronic progressive renal disease," Exp. Nephrol. 5:55-60 (1997).
Rudikoff, et al. Single amino acid substitution altering antigen-binding specificity. Proc Natl Acad Sci U S A. Mar. 1982;79(6):1979-83.
Salesi, et al. Clinical experience with bevacizumab in colorectal cancer. Anticancer Research, 2005; 25: 3619-3623.
Samanen, et al. Chemical approaches to improve the oral bioavailability of peptidergic molecules. J Pharm Pharmacol. Feb. 1996;48(2):119-35.
Schnaper, et al. Type IV collagenase(s) and TIMPs modulate endothelial cell morphogenesis in vitro. J Cell Physiol. Aug. 1993;156(2):235-46.
Sehgal et al., "A Method for the High Efficiency of Water-Soluble Carbodiimide-Mediated Amidation," Anal. Biochem. 218(1):87-91 (1994).
She et al., "Synergy between anti-endoglin (CD205) monoclonal antibodies and TGF-/3 in suppression of growth of human endothelial cells," Int. J. Cancer 108:251-257 (2004).
Shiozaki et al., "Antiangiogenic chimeric anti-endoglin(CD105) antibody: pharmacokinetics and immunogenicity in nonhuman primates and effects of doxorubicin," Cancer Immunology, Immunotherapy 55(2):140-150 (2005).
Silverman et al., "Corrigendum: Multivalent avimer proteins evolved by exon shuffling of a family of human receptor domains," Nat. Biotech. 24(2):220 (2006).
Silverman et al., "Multivalent avimer proteins evolved by exon shuffling of a family of human receptor domains," Nat. Biotech. 23:1493-1494 (2005).
Sjolander and Urbaniczky, "Integrated Fluid Handling System for Biomolecular Interaction Analysis," Anal. Chem. 63:2338-2345 (1991).
Sox, et al. Attachment of carbohydrate to the variable region of myeloma immunoglobulin light chains. Proc Natl Acad Sci U S A. Jul. 1970;66(3):975-82.
Stahle, et al., Multivariate data analysis and experimental design in biomedical research. Prog. Med. Chem. 1988, 25:291-338.
Stefansson et al , "Inhibition of Angiogenesis in Vivo by Plasminogen Activator Inhibitor-1," J. Biol. Chem. 276(11):8135-8141 (2001).
Su, et al. PTEN and phosphatidylinositol 3'-kinase inhibitors up-regulate p53 and block tumor-induced angiogenesis: evidence for an effect on the tumor and endothelial compartment. Cancer Res. Jul. 1, 2003;63(13):3585-92.
Szabo et al., "Surface plasmon resonance and its use in biomolecular interaction analysis (BIA)," Curr. Op. Struct. Biol. 5:699-705 (1995).
Szajani et al, "Effects of carbodiimide structure on the immobilization of enzymes," Appl. Biochem. Biotech. 30(2):225-231 (1991).
Tao et al., "Studies of aglycosylated chimeric mouse-human IgG. Role of carbohydrate in the structure and effector functions mediated by the human IgG constant region," J. Immunol. 143:2595-2601 (1989).
Taylor et al., "Selective Removal of a Heavy-Chain Glycosylation Sites Causes Immunoglobulin A Degradation and Reduced Secretion," Mol. Cell. Biol. 8:4197-4203 (1988).
Tracon Pharmaceuticals. Tracon pharmaceuticals announces dosing of initial three cancer patients in a Phase 1 clinical trial with TRC105, a human chimeric antibody. Company News. Jan. 8, 2008. www.traconpharma.com/content/pr_01_9_08.html.
Trill et al., "Production of monoclonal antibodies in COS and CHO cells," Curr. Op. Biotech. 6:553-560 (1995).
Tsujie et al., "Effective anti-angiogenic therapy of established tumors in mice by naked anti-human endoglin (CD105) antibody: Differences in growth rate and therapeutic response between tumors growing at different sites," Int. J. Oncology 29:1087-1094 (2006).
U.S. Appl. No. 12/570,918 Office action dated Mar. 28, 2012.
U.S. Appl. No. 12/570,918 Office action dated Oct. 17, 2012.
U.S. Appl. No. 12/751,907 Office action dated Sep. 30, 2011.
U.S. Appl. No. 13/485,702 Notice of Allowance dated Sep. 3, 2013.
U.S. Appl. No. 13/390,896 Office action dated Nov. 21, 2014.
U.S. Appl. No. 14/054,446 Restriction Requirement dated Mar. 12, 2015.
Uneda et al., "Anti-endoglin monoclonal antibodies are effective for suppressing metastasis and the primary tumors by targeting tumor vasculature," Intl. J. Cancer 125:1446-1453 (2009).
Varner et al., "Review: The Integrin au133: Angiogenesis and Apoptosis," Cell Adh. Commun. 3:367-374 (1995).
Volpert et al., "Idl regulates angiogenesis through transcriptional repression of thrombospondin-1," Cancer Cell 2(6):473-483 (2002).

(56) References Cited

OTHER PUBLICATIONS

Ward et al., "Binding activities of a repertoire of single immunoglobulin variable domains secreted from *Escherichia coli*," Nature 341:544-546 (1989).
Weidner et al., "Tumor Angiogenesis: A New Significant and Independent Prognostic Indicator in Early-Stage Breast Carcinoma," J. Natl. Cancer Inst. 84:1875-1887 (1992).
Williams, "Dissection of the extracellular human interferon gamma receptor into two immunoglobulin-like domains," Biochem. 34:1787-1797 (1995).
Wold, et al., PLS-regression: a basic tool of chemometrics. Chemom. Intell. Lab Syst. 2001, 58: 109-130.
Yan et al., "Human/Severe Combined Immunodeficient Mouse Chimeras," J. Clin. Invest. 91:986-996 (1993).
Zent et al., "Angiogenesis in Diabetic Nephropathy," Seminars in Nephrology 27(2):161-171 (2007).
U.S. Appl. No. 13/390,896 Office Action dated Jun. 16, 2015.
U.S. Appl. No. 14/054,446 Office Action dated Jun. 12, 2015.
Liu et al., Effects of the combination of TRC105 and bevacizumab on endothelial cell biology. Invest New Drugs, DOI 10.1007/s10637-014-0129-y.
Liu et al., Endoglin is dispensable for Vasculogenesis, but required for vascular endothelial growth factor-induced angiogenesis. PLOS/One, 9(1):e86273 (2014).
Uneda et al., Anti-endoglin monoclonal antibodies are effective for suppressing metastasis and the primary tumors by targeting tumor vasculature. Int. J. Cancer, 125(6):1446-1453 (2009).
Exinger et al., Multitargeted antifolate (Pemetrexed): A comprehensive review of its mechanisms of action, recent results and future prospects. Cancer Therapy, 1:315-322 (2003).
Kelland et al., Telomere targeting agents—clinical development candidates, European Journal of Cancer, Supplements, 4(12):140-141 (2006).
Ma et al., A Phase II trial of a combination of pemetrexed and gemcitabine in patients with metastatic breast cancer: an NCCTG study. Annals of Oncology, 17(2):226-231 (2006).
Mirsalis, et al., Preclinical toxicity studies of Methoxyamine (MX) and Terozolamide (TMZ). Proceedings of the American Association Cancer Res., vol. 45, 2 pages (2004).
U.S. Appl. No. 14/838,006 Office Action dated May 20, 2016.
Vogelzang et al., Phase III study of pemetrexed in combination with cisplatin versus cisplatin alone in patients with malignant pleural mesothelioma. Journal of Clinical Oncology, 21(14): 2636-2644 (2003).
Yan et al., Methoxyamine potentiates iododeoxyuridine-induced radiosensitization by altering cell cycle kinetics and enhancing senescence. Mol. Cancer Therapy, 5(4): 893-902 (2006).
PCT Patent Application No. PCT/US2010/045651 International Preliminary Report on Patentability dated Feb. 21, 2012.
U.S. Appl. No. 13/390,896 Office Action dated Nov. 3, 2016.
U.S. Appl. No. 14/838,006 Notice of Allowance dated Aug. 29, 2016.
Du et al., Crystal structure of chimeric antibody C2H7 Fab in complex with a CD20 peptide. Molecular Immunology, 45:2861-2868, 2008.
Ferrara et al., Discovery and development of Bevacizumab, an anti-VEGF antibody for treating cancer. Nature Reviews, Drug Discovery, 3:391-400, 2004.
U.S. Appl. No. 15/337,113 Restriction Requirement dated Jan. 13, 2017.
Bussolati et al., Identification of a tumor-initiating stem cell population in human renal carcinomas. FASEB Journal, 22:3696-3705, 2008.
European Patent Application No. 17194562.9 extended European Search Report dated Nov. 8, 2017.
Liu et al., Effects of the combination of TRC105 and bevacizumab on endothelial cell biology. Invest New Drugs, 9 pages, published online Jul. 5, 2014.
Wood et al., PTK787/ZK 222584, A novel and potent inhibitor of vascular endothelial growth factor receptor tyrosine kinases, impairs vascular endothelial growth factor-induced responses and tumor growth after oral administration. Cancer Research, AACR—American Association for Cancer Research, US, 60(8):2178-2189, 2000.
Akagi, A. et al., Expression of Type XVI collagen in human skin fibroblasts: Enhanced expression in fibrotic skin diseases. J. Invest. Dermatol., 113:246-250, 1999.
Al-Lazikani et al, Standard conformations for the canonical structures of immunoglobulins. J. Mol Biology, 273(4):927-948, 1997.
Appleton, I., et al., Short Communication: Apoptosis, necrosis, and proliferation. Possible implications in the etiology of keloids. Am. J. Pathol., 149(5):1441-1447, 1996.
Castonguay et al., Soluble endoglin specifically binds bone morphogenetic proteins 9 and 10 via its orphan domain, inhibits blood vessel formation, and suppresses tumor growth. Journal of Biological Chemistry, 286(34):30034-30046, 2011.
Chothia et al., Structural repertoire of the human VH segments J.Mol.Biol. 227:799-817, 1992.
Flaherty et al., Steroids in idiopathic pulmonary fibrosis: A prospective assessment of adverse reactions, response to therapy, and survival. Am. J. Med., 110:278-282, 2001.
Ge and Butcher, Cloning and expression of a cDNA encoding mouse endoglin, an endothelial cell TGF-β ligand. 138(1-2):201-206, 1994.
Girogescu, Non-invasive Biochemical Markers of Liver Fibrosis, J. Gastrointestin. Liver Dis., 15(2): 149-159, 2006.
International preliminary report on patentability dated Apr. 14, 2011 for PCT/UUS2009/059086.
Kapur et al., Reduced endoglin activity limits cardiac fibrosis and improves survival in heart failure Circulation, 125:2728-2738, 2012.
Kapur et al., Reducing endoglin activity limits calcineurin and TRPC-6 expression and improves survival in a mouse model of right ventricular pressure overload. Journal of the American Heart Association, 3:e000965, 17 pages, 2014, downloaded from the internet: http://jaha.ahajournals.org/.
Lasky and Brody, Interstitial fibrosis and growth factors. Environ. Health Perspect., 108 Suppl 4:751-762, 2000.
Li and Friedman, Liver fibrogenesis and the role of hepatic stellate cells: New insights and prospects for therapy. Gastroenterol. Hepatol. 14:618-633, 1999.
Liu et al., Modulation of circulating protein biomarkers following TRC105 (anti-endoglin antibody) treatment in patients with advanced cancer. Cancer Medicine, published by John Wiley & Sons, 2014, 12 pages.
Martin and Thornton, Structural families in loops of homologous proteins: automatic classification, modelling and application to antibodies. J.Mol.Biol., 263(5):800-815, 1996.
Martinez, Hampton et al., Mortality in idiopathic pulmonary fibrosis (IPF): Predictors prior to high dose corticosteroid therapy. Am. J. Respir. Crit. Care Med., 149:A878, 1994.
Morris et al., Endoglin promotes TGF-beta/Smad1 signaling in scleroderma fibroblasts. Journal of Cellular Physiology, 226(12):3340-3348, 2011. (Abstract only).
PCT/US2015/060136 International Preliminary Report on Patentability dated May 26, 2017.
PCT/US2015/060136 International Search Report and Written Opinion dated Feb. 3, 2016.
Ryu et al., Idiopathis pulmonary fibrosis: Current concepts. Mayo Clin. Proc., 73:1085-1101, 1998.
Sanyal et al., Endpoints and clinical trial design for nonalcoholic steatohepatitis. Hepatology, 54(1):344-353, 2011.
Schena, F. and Gesualdo, L., Pathogenic Mechanisms of Diabetic Nephropathy, J. Am. Soc. Nephrol., 16:S30-33, 2005.
Tomlinson et al., The Structural repertoire of the human VK domain. The EMBO Journal, 14(18):4628-4638, 1995.
Travis et al., Idiopathic nonspecific interstitial pneumonia: Prognostic significance of cellular and fibrosing patterns. Survival comparison with usual interstitial pneumonia and desquamative interstitial pneumonia. Am. J. Surg. Path., 24(1):19-33, 2000.
U.S. Appl. No. 13/390,896 Office Action dated Aug. 23, 2017.
U.S. Appl. No. 15/337,113 Office Action dated Jul. 12, 2017.

(56) References Cited

OTHER PUBLICATIONS

Wang et al., A Monoclonal antibody detects heterogeneity in vascular endothelium of tomours and normal tissues. Int. J. Cancer 54:363-370, 1993.
Whaley-Connell and Sower, Chronic Kidney Disease and the Cardiometabolic Syndrome, J. Clin. Hypert., 8(8):546-48, 2006.
U.S. Appl. No. 15/520,020 Office Action dated Jun. 22, 2018.

\* cited by examiner

FIG. 1

A.  TRC105 V$_L$: CDRs are underlined

QIVLSQSPAILSASPGEKVTMTC<u>RASSSVSYMH</u>WYQQKPGSSPKPWIY<u>ATSNLAS</u>GVPVRFSGSGS
GTSYSLTISRVEAEDAATYYC<u>QQWSSNPLT</u>FGAGTKLELK (SEQ ID NO: 1)

B.  TRC105 C$_L$:

RTVAAPSVFIFPPSDEQLKSGTASVVCLLNNFYPREAKVQWKVDNALQSGNSQESVTEQDSKDSTY
SLSSTLTLSKADYEKHKVYACEVTHQGLSSPVTKSFNRGEC (SEQ ID NO: 2)

C.  TRC105 V$_H$: CDRs are underlined

EVKLEESGGGLVQPGGSMKLSCAASGFTFS<u>DAWMD</u>WVRQSPEKGLEWVA<u>EIRSKASNHATYYAESV
KG</u>RFTISRDDSKSSVYLQMNSLRAEDTGIYYCTR<u>WRRFFDS</u>WGQGTTLTVSS          (SEQ ID
NO: 3)

D.  TRC105 Cγ1

ASTKGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPELLGGPSVFLFPPKPKD
TLMISRTPEVTCVVVDVSHEDPEVKFNWYVDGVEVHNAKTKPREEQYNSTYRVVSVLTVLHQDWLN
GKEYKCKVSNKALPAPIEKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVMHEALHNHYTQKSLSLSPGK
(SEQ ID NO: 4)

| | | | |
|---|---|---|---|
| E. | VL CDR1: | RASSSVSYMH | (SEQ ID NO: 5) |
| F. | VL CDR2: | ATSNLAS | (SEQ ID NO: 6) |
| G. | VL CDR3: | QQWSSNPLT | (SEQ ID NO: 7) |
| H. | VH CDR1: | DAWMD | (SEQ ID NO: 8) |
| I. | VH CDR2: | EIRSKASNHATYYAESVKG | (SEQ ID NO: 9) |
| J. | VH CDR3: | WRRFFDS | (SEQ ID NO: 10) |

Model of Regulation of Angiogenesis by CD105 (Endoglin)

ANTIBODY FORMULATIONS AND USES THEREOF

CROSS-REFERENCE

This application is a § 371 national stage application of International PCT Application No. PCT/US13/058265, which claims the benefit of U.S. Provisional Application No. 61/697,111, filed Sep. 5, 2012, each of which application is incorporated herein by reference in its entirety.

This application is related to the following patent applications: US Publication No. US 2010-0098692 A1; U.S. Pat. No. 8,221,753; U.S. application Ser. No. 13/485,702; and U.S. application Ser. No. 13/390,896, which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Sep. 4, 2013, is named 35882-714.601_SL.txt and is 22,121 bytes in size.

BACKGROUND OF THE INVENTION

Cancer is the second leading cause of human death next to coronary disease. Worldwide, millions of people die from cancer every year. In the United States alone, cancer causes the death of well over a half-million people each year, with some 1.4 million new cases diagnosed per year. While deaths from heart disease have been declining significantly, those resulting from cancer generally are on the rise. In many countries, cancer is already the leading cause of death.

Moreover, even for those cancer patients that initially survive their primary cancers, common experience has shown that their lives are dramatically altered. Many cancer patients experience strong anxieties driven by the awareness of the potential for recurrence or treatment failure. Many cancer patients experience significant physical debilitations following treatment.

Generally speaking, the fundamental problem in the management of the deadliest cancers is the lack of effective and non-toxic systemic therapies. Cancer is a complex disease characterized by genetic mutations that lead to uncontrolled cell growth. Cancerous cells are present in all organisms and under normal circumstances their excessive growth is tightly regulated by various physiological factors.

Angiogenesis is the physiological process by which new blood vessels develop from pre-existing vessels. Angiogenesis has been suggested to play a role in both normal and pathological processes. For example, angiogenic processes are involved in the development of the vascular systems of animal organs and tissues.

In certain pathological conditions, angiogenesis is stimulated as a means to provide adequate blood and nutrient supply to the cells within affected tissue. Many of these pathological conditions involve aberrant cell proliferation and/or regulation. Solid cancers and exudative macular degeneration depend upon the recruitment of a new blood supply for continued growth as well as metastasis.

SUMMARY OF THE INVENTION

Provided herein are new formulations of anti-CD105 antibodies, pre-filled syringes containing the formulations, and the use of such formulations for treating angiogenesis-related disorders. The present application provides formulations that may be used for intravenous or intraocular administration of, for example, treatment of cancers associated with CD105 and ophthalmologic conditions.

In one aspect, provided herein is a formulation comprising from about 1 mg/ml to about 150 mg/ml of an anti-CD105 antibody, or antigen-binding fragment thereof, up to about 100 mM buffering agent, up to about 1 M polyol, and a pH of about 4.0 to about 7.5.

In one aspect, the formulation is stable following preparation, which can be tested according to conventional means. With respect to stability of the formulation over time, at least 95% of the anti-CD105 antibody, or antigen-binding fragment thereof, may be present as a monomer following storage at about 2 to 8° C. for at least about 12 months as measured by size exclusion chromatography (SEC). In some embodiments, the buffering agent of such formulations is histidine or phosphate buffered saline. With respect to the stability of the formulation over time, at least 90% of the anti-CD105 antibody, or antigen-binding fragment thereof, may be present as a monomer following storage at about 25° C. for at least about 6 months as measured by size exclusion chromatography (SEC). In some embodiments, the buffering agent of such formulations is acetate.

Further, the anti-CD105 antibody, or antigen-binding fragment thereof, may display from about 50 to about 150% binding by a CD105 ELISA binding assay after storage at about 2 to 8° C. for at least about 12 months.

The average isoelectric point (pI) of the anti-CD105 antibody may be from about 8.7 to about 9.2 after storage at 2 to 8° C. for at least about 12 months, as measured by, for example, capillary electrophoresis-isoelectric focusing.

One would understand that the anti-CD105 antibody, or antigen-binding fragment thereof, may be stable for at least about 12 months, at least about 18 months, at least about 24 months, at least about 30 months, at least about 36 months, or more.

A formulation may contain at least 95% of the anti-CD105 antibody present as monomer as measured by SEC following freezing and thawing cycles of the formulation. Alternatively, or in addition, a formulation may contain at least 95% of the anti-CD105 antibody present as monomer as measured by SEC when subjected to agitation stress.

The anti-CD105 antibody, or antigen-binding fragment thereof, may comprise any sequence that of CDRs that are capable of binding to CD105. In one non-limiting embodiment, the anti-CD105 antibody comprises a light chain variable region ($V_L$) having an amino acid sequence set forth as SEQ ID NO: 1; a light chain constant region ($C_L$) having an amino acid sequence set forth as SEQ ID NO: 2; a heavy chain variable region ($V_H$) having an amino acid sequence set forth as SEQ ID NO: 3; and a constant region (Fc) having an amino acid sequence set forth as SEQ ID NO: 4 (See, e.g., FIG. 1).

In another non-limiting embodiment, the anti-CD105 antibody comprises a $V_L$ CDR1 having an amino acid sequence set forth as SEQ ID NO: 5; a $V_L$ CDR2 having an amino acid sequence set forth as SEQ ID NO: 6; a $V_L$ CDR3 having an amino acid sequence set forth as SEQ ID NO: 7; a $V_H$ CDR1 having an amino acid sequence set forth as SEQ ID NO: 8; a $V_H$ CDR2 having an amino acid sequence set forth as SEQ ID NO: 9; and a $V_H$ CDR3 having an amino acid sequence set forth as SEQ ID NO: 10.

An isolated humanized, de-immunized anti-CD105 antibody can comprise a heavy chain variable region having the amino acid sequence set forth as SEQ ID NO: 11 and a light chain variable region having the amino acid sequence set forth as SEQ ID NO: 12. Other non-limiting examples of humanized-deimmunized heavy chains include, but are not limited to, SEQ ID NOS: 13, 14, 15 and 16. Other non-limiting examples of humanized-deimmunized light chains include, but are not limited to, SEQ ID NOS: 17, 18, 19, 20, 21, 22, and 23. The sequences are provided below in Example 17.

The formulation may contain from about 1 mg/ml to about 150 mg/ml of an anti-CD105 antibody, or antigen-binding fragment thereof, or any value therein including, but not limited to, about 2 mg/ml, about 5 mg/ml, about 7.5 mg/ml, about 10 mg/ml, 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, about 75 mg/ml, about 80 mg/ml, about 85 mg/ml, about 90 mg/ml, about 95 mg/ml, about 100 mg/ml, about 105 mg/ml, about 110 mg/ml, about 115 mg/ml, about 120 mg/ml, about 125 mg/ml, about 130 mg/ml, about 135 mg/ml, about 140 mg/ml, about 145 mg/ml, about 150 mg/ml, or more.

In one embodiment, the formulation comprises about 25 mg/ml of the anti-CD105 antibody or, antigen-binding fragment thereof.

In another embodiment, the formulation comprises about 50 mg/ml of the anti-CD105 antibody or, antigen-binding fragment thereof.

In yet another embodiment, the formulation comprises about 100 mg/ml of the anti-CD105 antibody or, antigen-binding fragment thereof.

Formulations as described herein may contain a buffering agent such as, for example, histidine, acetate, citrate or phosphate. In one embodiment, the formulation comprises about 5 mM, about 7.5 mM, about 10 mM, about 12.5 mM, about 15 mM, about 17.5 mM, 20 mM, about 22.5 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, or about 100 mM histidine, acetate, citrate or phosphate.

Formulations may be prepared for any type of administration known for antibodies including, but not limited to, intravitreal and intravenous administration.

Formulations provided herein may further include an acceptable carrier or excipient including any carrier or excipient that is a pharmaceutically acceptable carrier or excipient and which is acceptable for administration to a patient.

In one embodiment, a formulation provided herein is isotonic. By "isotonic" is meant that the formulation of interest has essentially the same osmotic pressure as human blood. Isotonic formulations will generally have an osmotic pressure from about 250 to 350 milliosmolar (mOsm). Isotonicity can be measured using a vapor pressure or ice-freezing type osmometer, for example. In another embodiment, a formulation provided herein is hypertonic. An "isotonic" formulation is one which has essentially the same osmotic pressure as human blood. Correspondingly, the term "hypertonic" is used to describe a formulation with an osmotic pressure above that of human blood.

A formulation provided herein may contain a polyol in an amount of less than 1 M. For example, polyol may be present in the formulation in an amount of about 50 mM, about 75 mM, about 100 mM, about 150 mM, about 200 mM, about 225 mM, about 240 mM, about 250 mM, about 300 mM, about 350 mM, about 400 mM, about 450 mM, about 500 mM, about 550 mM, about 600 mM, about 650 mM, about 700 mM, about 750 mM, about 800 mM, about 850 mM, about 900 mM, about 950 mM, about 1 M, or any integer therein. In one embodiment, the formulation is made isotonic with a salt in a concentration of from about 100 mM to about 175 mM. For example, the formulation containing polyol in an amount of less than 300 mM is made isotonic with a salt in a concentration of about 130 mM.

In one aspect, a polyol to be used in the formulations provided herein may be a sugar such as, for example, a non-reducing sugar. Representative examples of non-reducing sugars include, but are not limited to, trehalose and sucrose. For example, a formulation may comprise from about 200 mM to about 300 mM trehalose or sucrose. In one embodiment, a formulation may comprise about 240 mM trehalose or sucrose.

Alternatively, the sugar may be sorbitol in an amount (concentration) of from about 200 mM to about 300 mM. In one embodiment, a formulation may comprise about 240 mM sorbitol.

Further non-limiting examples of a formulation provided herein is any one of formulations 1-39 of Table 1.

A formulation provided herein may have a pH of about 4.0 to about 7.5. In one embodiment, a formulation provided herein may have a pH of about 4.5, about 5.0, about 5.5, about 6.0, about 6.5, or about 7.0.

In one embodiment, formulations provided herein do not contain a surfactant. Optionally, in some cases, a surfactant can be included in the formulations. Non-limiting examples of surfactants include polysorbate 20, polysorbate 80 and Pluronic® F68.

Also provided herein is a pre-filled syringe suitable for intravenous or intravitreal administration comprising a formulation described herein. Such pre-filled syringes may be packaged and labeled for use for treatment of an angiogenesis-related condition such as any of the conditions described herein. Packages may further include directions for storage and administration. Provided herein is a package containing one or more pre-filled syringes suitable for intravenous or intravitreal administration comprising the formulation of any of the preceding claims.

One embodiment of the present application contemplates the use of any of the compositions described herein to formulate a medicament for treating a disorder described herein. Medicaments can be formulated based on the physical characteristics of the patient/subject needing treatment, and can be formulated in single or multiple formulations. Medicaments can be packaged in a suitable package with appropriate labels for the distribution to hospitals and clinics wherein the label is for the indication of treating a disorder as described herein in a subject. Medicaments can be packaged as a single or multiple units. Instructions for the dosage and administration of the compositions described herein can be included with the packages.

Provided herein is a method of treating an angiogenesis-related disease in a patient (subject) in need thereof, comprising administering to said patient a formulation described herein. Such formulations may be administered to the patient intravitreally or intravenously.

An angiogenesis-related disease described herein may be, for example, a cancer or a metastasis. In one embodiment, the cancer is a solid tumor. Cancers to be treated include, for example, an epithelial based tumor. Non-limiting examples of cancers to be treated with such formulations include, but are not limited to, a lung cancer, a gynecologic malignancy, a melanoma, a breast cancer, a pancreatic cancer, an ovarian cancer, a uterine cancer, a colorectal cancer, a prostate cancer, a kidney cancer, a head cancer, a pancreatic cancer, a liver cancer (hepatocellular cancer), a uterine cancer, a neck cancer, a kidney cancer (renal cell cancer), a sarcoma, a myeloma, and a lymphoma. Formulations for treatment of a cancer or a metastasis may be administered to the patient intravenously.

Alternatively, an angiogenesis-related disease described herein may be, for example, is an ophthalmologic condition. Ophthalmologic conditions include, but are not limited to, age-related macular degeneration, diabetic retinopathy, macular edema, and/or choroidal neovascularization. Age related macular degeneration (AMD) may be wet AMD or dry AMD. Formulations for treatment of an ophthalmologic condition may be administered to the patient intravitreally.

In such methods, the formulation may be administered to a patient one or more times. For example, the formulation may be administered once per day, once per week, once per month, once bi-monthly, once every two months, once every three months, once every four months, once every 5 months, or once every 6 months. Treatment schedules may be increased or decreased as needed depending upon the response of the patient to the treatment.

In one aspect, a formulation is administered until one or more signs or symptoms of the angiogenesis-related disease are reduced.

With respect to ophthalmologic conditions, the one or more signs or symptoms may include, but not be limited to, shrinking blood vessels, inhibiting endothelial cell proliferation associated with ocular disease, clearing signs or symptoms of bleeding, treating cloudy vision, providing stasis of vision loss, improving vision, improving visual acuity, reducing macular edema and/or preventing leakage of blood vessels.

With respect to cancers or metastases, treatment may result in improvement of the patient's condition and treatment can be assessed by determining if one or more of the following factors has occurred: decreased cell proliferation, decreased numbers of cells, increased apoptosis, or decreased survival of at least a portion of the cells comprising the cell proliferative disorder.

Treatment may result in partial or total elimination of a tumor or metastases and/or prolongation of survival of the patient.

In one embodiment, one or more signs or symptoms are reduced in severity or duration by about 2%, about 5%, about 10%, about 15%, about 20%, about 25%, about 30%, about 35%, about 40%, about 45%, about 50%, about 55%, about 60%, about 65%, about 70%, about 75%, about 80%, about 90%, about 95%, or about 100% following administration of one or more doses of the formulation to the patient.

In another embodiment, one or more signs or symptoms are reduced in severity or duration by about 2-fold, about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 90-fold, about 95-fold, about 100-fold, or more, following administration of one or more doses of the formulation to the patient.

Provided herein is a method of treating an ophthalmologic condition in a patient in need thereof, comprising administering to said patient a formulation described herein, whereby one or more signs or symptoms of said ophthalmologic condition are ameliorated by the treatment. Administration of the formulation may be intravitreal administration.

Also provided herein is a method of preventing or treating a cancer or metastasis in a subject in need thereof, comprising administering to said patient a formulation described herein, whereby one or more signs or symptoms of said cancer or metastasis are ameliorated. Administration of the formulation may be intravenous administration.

In the methods provided herein, a subject to be treated can be a human or a non-human subject. Formulations provided herein can be administered once or multiple times depending on the health of the patient, the progression of the disease or condition, and the efficacy of the treatment. Adjustments to therapy and treatments can be made throughout the course of treatment (e.g., the dosage of an antibody in a composition).

Provided herein is a method of monitoring the efficacy of one or more of any of the methods provided herein. Levels of soluble CD105 have been correlated with survival in cancer patients and can be monitored prior to and during therapy. Levels of soluble CD105 can, therefore, be one indication that a therapeutic regimen is effective in treating the patient. Treatments described herein may include one or more additional treatments.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the embodiments are set forth with particularity in the appended claims. A better understanding of the features and advantages of the present embodiments may be obtained by reference to the following detailed description that sets forth illustrative embodiments, in which the principles of the embodiments are utilized, and the accompanying drawings of which:

FIGS. 1A-J provide exemplary amino acid sequences of an anti-CD105 antibody (TRC105) described herein. FIG. 1A is a representative variable light (VL) chain of an anti-CD105 antibody (SEQ ID NO: 1); FIG. 1B is a representative constant light chain (CL) of an anti-CD105 antibody (SEQ ID NO: 2); FIG. 1C is a representative variable heavy (VH) chain of an anti-CD105 antibody (SEQ ID NO: 3); and FIG. 1D is a representative constant gamma-1 heavy chain of an anti-CD105 antibody (SEQ ID NO: 4). FIGS. 1E-G represent CDRs 1, 2 and 3 of the VL, respectively. FIGS. 1H-J represent CDRs 1, 2 and 3 of the VH, respectively.

DETAILED DESCRIPTION OF THE INVENTION

Figure 2:
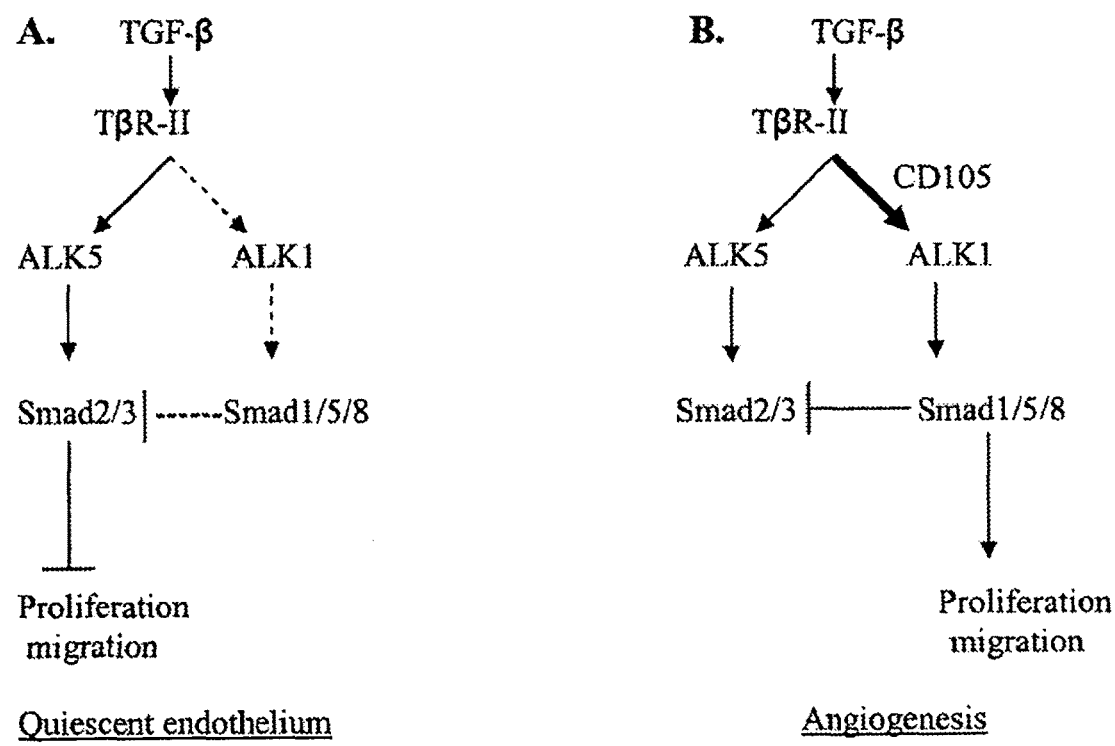
FIG. 2 provides diagram of the TGF-β/ALK5 signaling pathway. The TGF-β/ALK5 pathway (A) leads to inhibition of cell proliferation. The TGF-β/ALK1 pathway (B) induces endothelial cell proliferation and requires CD105 (endoglin) for ALK1 signaling. The dotted lines indicate inactive or blocked pathways. The bolded arrow indicates stimulation of a signaling pathway.

It is to be understood that the terminology used herein is for the purpose of describing particular embodiments only, and is not intended to be limiting. Further, it is understood that a number of methods and materials similar or equivalent to those described herein can be used in the practice of the present inventions.

In accordance with the present application, there may be employed conventional cellular biology, molecular biology, microbiology, and recombinant DNA techniques as explained fully in the art.

As used in this specification and the appended claims, the singular forms "a", "an", and "the" include plural references unless the context clearly dictates otherwise. Thus for example, references to "a method" include one or more methods, and/or steps of the type described herein and/or which will become apparent to those persons skilled in the art upon reading this disclosure.

Anti-CD105 antibodies may be used to treat or prevent various forms of angiogenesis-related disorders. Described herein are methods of treating or various forms of cancer, solid tumors, and metastases and the like via the administration of the formulations described herein.

Antibody Terminology

As used herein, the term "antibody" refers to an immunoglobulin (Ig) whether natural or partly or wholly synthetically produced. The term also covers any polypeptide or protein having a binding domain which is, or is homologous to, an antigen-binding domain. The term further includes "antigen-binding fragments" and other interchangeable terms for similar binding fragments such as described below.

Native antibodies and native immunoglobulins are usually heterotetrameric glycoproteins of about 150,000 Daltons, composed of two identical light (L) chains and two identical heavy (H) chains. Each light chain is typically linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ("$V_H$" or "VH") followed by a number of constant domains ("$C_H$" or "CH"). Each light chain has a variable domain at one end ("$V_L$" or "VL") and a constant domain ("$C_L$" or "CL") at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The terms "synthetic polynucleotide," "synthetic gene" or "synthetic polypeptide," as used herein, mean that the corresponding polynucleotide sequence or portion thereof, or amino acid sequence or portion thereof, is derived, from a sequence that has been designed, or synthesized de novo, or modified, compared to an equivalent naturally-occurring sequence. Synthetic polynucleotides (antibodies or antigen binding fragments) or synthetic genes can be prepared by methods known in the art, including but not limited to, the chemical synthesis of nucleic acid or amino acid sequences. Synthetic genes are typically different from naturally-occurring genes, either at the amino acid, or polynucleotide level, (or both) and are typically located within the context of synthetic expression control sequences. Synthetic gene polynucleotide sequences, may not necessarily encode proteins with different amino acids, compared to the natural gene; for example, they can also encompass synthetic polynucleotide sequences that incorporate different codons but which encode the same amino acid (i.e., the nucleotide changes represent silent mutations at the amino acid level).

With respect to antibodies, the term "variable domain" refers to the variable domains of antibodies that are used in the binding and specificity of each particular antibody for its particular antigen. However, the variability is not evenly distributed throughout the variable domains of antibodies. Rather, it is concentrated in three segments called hypervariable regions (also known as CDRs) in both the light chain and the heavy chain variable domains. More highly conserved portions of variable domains are called the "framework regions" or "FRs." The variable domains of unmodified heavy and light chains each contain four FRs (FR1, FR2, FR3 and FR4), largely adopting a β-sheet configuration interspersed with three CDRs which form loops connecting and, in some cases, part of the n-sheet structure. The CDRs in each chain are held together in close proximity by the FRs and, with the CDRs from the other chain, contribute to the formation of the antigen-binding site of antibodies (see Kabat et al., Sequences of Proteins of Immunological Interest, 5th Ed. Public Health Service, National Institutes of Health, Bethesda, Md. (1991), pages 647-669).

The terms "hypervariable region" and "CDR" when used herein, refer to the amino acid residues of an antibody which are responsible for antigen-binding. The CDRs comprise amino acid residues from three sequence regions which bind in a complementary manner to an antigen and are known as CDR1, CDR2, and CDR3 for each of the $V_H$ and $V_L$ chains. In the light chain variable domain, the CDRs typically correspond to approximately residues 24-34 (CDRL1), 50-56 (CDRL2) and 89-97 (CDRL3), and in the heavy chain variable domain the CDRs typically correspond to approximately residues 31-35 (CDRH1), 50-65 (CDRH2) and 95-102 (CDRH3) according to Kabat et al., Sequences of Proteins of Immunological Interest, 5th Ed. Public Health Service, National Institutes of Health, Bethesda, Md. (1991)). It is understood that the CDRs of different antibodies may contain insertions, thus the amino acid numbering may differ. The Kabat numbering system accounts for such insertions with a numbering scheme that utilizes letters attached to specific residues (e.g., 27A, 27B, 27C, 27D, 27E, and 27F of CDRL1 in the light chain) to reflect any insertions in the numberings between different antibodies. Alternatively, in the light chain variable domain, the CDRs typically correspond to approximately residues 26-32 (CDRL1), 50-52 (CDRL2) and 91-96 (CDRL3), and in the heavy chain variable domain, the CDRs typically correspond to approximately residues 26-32 (CDRH1), 53-55 (CDRH2) and 96-101 (CDRH3) according to Chothia and Lesk, J. Mol. Biol., 196: 901-917 (1987)).

As used herein, "framework region" or "FR" refers to framework amino acid residues that form a part of the antigen binding pocket or groove. In some embodiments, the framework residues form a loop that is a part of the antigen binding pocket or groove and the amino acids residues in the loop may or may not contact the antigen. Framework regions generally comprise the regions between the CDRs. In the light chain variable domain, the FRs typically correspond to approximately residues 0-23 (FRL1), 35-49 (FRL2), 57-88 (FRL3), and 98-109 and in the heavy chain variable domain the FRs typically correspond to approximately residues 0-30 (FRH1), 36-49 (FRH2), 66-94 (FRH3), and 103-133 according to Kabat et al., Sequences of Proteins of Immunological Interest, 5th Ed. Public Health Service, National Institutes of Health, Bethesda, Md. (1991)). As discussed above with the Kabat numbering for the light chain, the heavy chain too accounts for insertions in a similar manner (e.g., 35A, 35B of CDRH1 in the heavy chain). Alternatively, in the light chain variable domain, the FRs typically correspond to approximately residues 0-25 (FRL1), 33-49 (FRL2) 53-90 (FRL3), and 97-109 (FRL4), and in the heavy chain variable domain, the FRs typically correspond to approximately residues 0-25 (FRH1), 33-52 (FRH2), 56-95 (FRH3), and 102-113 (FRH4) according to Chothia and Lesk, *J. Mol. Biol.*, 196: 901-917 (1987)).

Constant domains (Fc) of antibodies are not involved directly in binding an antibody to an antigen but, rather, exhibit various effector functions, such as participation of the antibody in antibody-dependent cellular toxicity via interactions with, for example, Fc receptors (FcR). Fc domains can also increase bioavailability of an antibody in circulation following administration to a patient. Substitution of a murine Fc domain with a human Fc domain can also reduce side HAMA reactions.

Depending on the amino acid sequence of the constant domain of their heavy chains, immunoglobulins can be assigned to different classes. There are five major classes of immunoglobulins: IgA, IgD, IgE, IgG, and IgM, and several of these can be further divided into subclasses (isotypes), e.g., IgG1, IgG2, IgG3, IgG4, IgA1, and IgA2. The heavy-chain constant domains (Fc) that correspond to the different classes of immunoglobulins are called $\alpha$, $\delta$, $\epsilon$, $\gamma$, and $\mu$ respectively. The subunit structures and three-dimensional configurations of different classes of immunoglobulins are well known.

The "light chains" of antibodies from any vertebrate species can be assigned to one of two clearly distinct types, called kappa or ("$\kappa$") and lambda or ("$\lambda$"), based on the amino acid sequences of their constant domains.

The terms "antigen-binding portion of an antibody," "antigen-binding fragment," "antigen-binding domain," "antibody fragment" or a "functional fragment of an antibody" are used interchangeably herein to refer to one or more fragments of an antibody that retain the ability to specifically bind to an antigen. Non-limiting examples of antibody fragments included within such terms include, but are not limited to, (i) a Fab fragment, a monovalent fragment consisting of the $V_L$, $V_H$, $C_L$ and $C_{H1}$ domains; (ii) a F(ab')$_2$ fragment, a bivalent fragment containing two Fab fragments linked by a disulfide bridge at the hinge region; (iii) a Fd fragment consisting of the $V_H$ and $C_{H1}$ domains; (iv) a Fv fragment containing the $V_L$ and $V_H$ domains of a single arm of an antibody, (v) a dAb fragment (Ward et al., 1989) *Nature* 341:544 546), which containing a $V_H$ domain; and (vi) an isolated CDR. Additionally included in this definition are "one-half" antibodies comprising a single heavy chain and a single light chain. Other forms of single chain antibodies, such as diabodies are also encompassed herein.

"F(ab')$_2$" and "Fab'" moieties can be produced by treating an Ig with a protease such as pepsin and papain, and include antibody fragments generated by digesting immunoglobulin near the disulfide bonds existing between the hinge regions in each of the two heavy chains. For example, papain cleaves IgG upstream of the disulfide bonds existing between the hinge regions in each of the two heavy chains to generate two homologous antibody fragments in which an light chain composed of $V_L$ and $C_L$ (light chain constant region), and a heavy chain fragment composed of $V_H$ and $C_{H\gamma1}$ ($\gamma$1) region in the constant region of the heavy chain) are connected at their C terminal regions through a disulfide bond. Each of these two homologous antibody fragments is called Fab'. Pepsin also cleaves IgG downstream of the disulfide bonds existing between the hinge regions in each of the two heavy chains to generate an antibody fragment slightly larger than the fragment in which the two above-mentioned Fab' are connected at the hinge region. This antibody fragment is called F(ab')$_2$.

The Fab fragment also contains the constant domain of the light chain and the first constant domain ($C_H1$) of the heavy chain. Fab' fragments differ from Fab fragments by the addition of a few residues at the carboxyl terminus of the heavy chain $C_H1$ domain including one or more cysteine(s) from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Fv" refers to an antibody fragment which contains a complete antigen-recognition and antigen-binding site. This region consists of a dimer of one heavy chain and one light chain variable domain in tight, non-covalent or covalent association (disulfide linked Fvs have been described in the art, Reiter et al. (1996) Nature Biotechnology 14:1239-1245). It is in this configuration that the three CDRs of each variable domain interact to define an antigen-binding site on the surface of the $V_H$-$V_L$ dimer. Collectively, a combination of one or more of the CDRs from each of the $V_H$ and $V_L$ chains confer antigen-binding specificity to the antibody. For example, it would be understood that, for example, the CDRH3 and CDRL3 could be sufficient to confer antigen-binding specificity to an antibody when transferred to $V_H$ and $V_L$ chains of a recipient antibody or antigen-binding fragment thereof and this combination of CDRs can be tested for binding, affinity, etc. using any of the techniques described herein. Even a single variable domain (or half of an Fv comprising only three CDRs specific for an antigen) has the ability to recognize and bind antigen, although likely at a lower affinity than when combined with a second variable domain. Furthermore, although the two domains of a Fv fragment ($V_L$ and $V_H$), are coded for by separate genes, they can be joined using recombinant methods by a synthetic linker that enables them to be made as a single protein chain in which the $V_L$ and $V_H$ regions pair to form monovalent molecules (known as single chain Fv (scFv); Bird et al. (1988) *Science* 242:423-426; Huston et al. (1988) *Proc. Natl. Acad. Sci. USA* 85:5879-5883; and Osbourn et al. (1998) *Nat. Biotechnol.* 16:778). Such scFvs are also intended to be encompassed within the term "antigen-binding portion" of an antibody. Any $V_H$ and $V_L$ sequences of specific scFv can be linked to an Fc region cDNA or genomic sequences, in order to generate expression vectors encoding complete Ig (e.g., IgG) molecules or other isotypes. $V_H$ and $V_L$ can also be used in the generation of Fab, Fv or other fragments of Igs using either protein chemistry or recombinant DNA technology.

"Single-chain Fv" or "sFv" antibody fragments comprise the $V_H$ and $V_L$ domains of an antibody, wherein these domains are present in a single polypeptide chain. In some embodiments, the Fv polypeptide further comprises a polypeptide linker between the $V_H$ and $V_L$ domains which enables the sFv to form the desired structure for antigen binding. For a review of sFvs, see, e.g., Pluckthun in The Pharmacology of Monoclonal Antibodies, Vol. 113, Rosenburg and Moore eds. Springer-Verlag, New York, pp. 269-315 (1994).

The term "AVIMER™" refers to a class of therapeutic proteins of human origin, which are unrelated to antibodies and antibody fragments, and are composed of several modular and reusable binding domains, referred to as A-domains (also referred to as class A module, complement type repeat, or LDL-receptor class A domain). They were developed from human extracellular receptor domains by in vitro exon shuffling and phage display (Silverman et al., 2005, *Nat. Biotechnol.* 23:1493-1494; Silverman et al., 2006, *Nat. Biotechnol.* 24:220). The resulting proteins can contain multiple independent binding domains that can exhibit improved affinity (in some cases, sub-nanomolar) and specificity compared with single-epitope binding proteins. See, for example, U.S. Patent Application Publ. Nos. 2005/0221384, 2005/0164301, 2005/0053973 and 2005/0089932, 2005/0048512, and 2004/0175756, each of which is hereby incorporated by reference herein in its entirety.

Each of the known 217 human A-domains comprises ~35 amino acids (~4 kDa); and these domains are separated by linkers that average five amino acids in length. Native A-domains fold quickly and efficiently to a uniform, stable structure mediated primarily by calcium binding and disulfide formation. A conserved scaffold motif of only 12 amino acids is required for this common structure. The end result is a single protein chain containing multiple domains, each of which represents a separate function. Each domain of the proteins binds independently and the energetic contributions of each domain are additive. These proteins were called "AVIMERs™" from avidity multimers.

The term "diabodies" refers to small antibody fragments with two antigen-binding sites, which fragments comprise a heavy chain variable domain (VH) connected to a light chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA* 90:6444 6448 (1993).

Antigen-binding polypeptides also include heavy chain dimers such as, for example, antibodies from camelids and sharks. Camelid and shark antibodies comprise a homodimeric pair of two chains of V-like and C-like domains (neither has a light chain). Since the $V_H$ region of a heavy chain dimer IgG in a camelid does not have to make hydrophobic interactions with a light chain, the region in the heavy chain that normally contacts a light chain is changed to hydrophilic amino acid residues in a camelid. $V_H$ domains of heavy-chain dimer IgGs are called $V_{HH}$ domains. Shark Ig-NARs comprise a homodimer of one variable domain (termed a V-NAR domain) and five C-like constant domains (C-NAR domains). In camelids, the diversity of antibody repertoire is determined by the CDRs 1, 2, and 3 in the $V_H$ or $V_{HH}$ regions. The CDR3 in the camel $V_{HH}$ region is characterized by its relatively long length, averaging 16 amino acids (Muyldermans et al., 1994, Protein Engineering 7(9): 1129). This is in Contrast to CDR3 Regions of antibodies of many other species. For example, the CDR3 of mouse $V_H$ has an average of 9 amino acids. Libraries of camelid-derived antibody variable regions, which maintain the in vivo diversity of the variable regions of a camelid, can be made by, for example, the methods disclosed in U.S. Patent Application Ser. No. 20050037421.

"Chimeric" forms of non-human (e.g., murine) antibodies include chimeric antibodies which contain minimal sequence derived from a non-human Ig. For the most part, chimeric antibodies are murine antibodies in which at least a portion of an immunoglobulin constant region (Fc), typically that of a human immunoglobulin are inserted in place of the murine Fc. For details, see Jones et al., *Nature* 321: 522-525 (1986); Reichmann et al., *Nature* 332: 323-329 (1988); and Presta, *Curr. Op. Struct. Biol.,* 2: 593-596 (1992).

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations, which can include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, monoclonal antibodies can be made by the hybridoma method first described by Kohler et al., *Nature* 256:495 (1975), or can be made by recombinant DNA methods (see, e.g., U.S. Pat. No. 4,816,567). In certain embodiments, the monoclonal antibodies can be isolated from phage antibody libraries using the techniques described in Clackson et al., *Nature* 352:624-628 (1991) and Marks et al., *J. Mol. Biol.* 222:581-597 (1991), for example.

Antibodies can be isolated and purified from the culture supernatant or ascites mentioned above by saturated ammonium sulfate precipitation, euglobulin precipitation method, caproic acid method, caprylic acid method, ion exchange chromatography (DEAE or DE52), or affinity chromatography using anti-Ig column or a protein A, G or L column such as described in more detail below.

When constructing an immunoglobulin molecule, variable regions or portions thereof may be fused to, connected to, or otherwise joined to one or more constant regions or portions thereof to produce any of the antibodies described herein. This may be accomplished in a variety of ways known in the art, including but not limited to, molecular cloning techniques or direct synthesis of the nucleic acids encoding the molecules As used herein, "immunoreactive" refers to binding agents, antibodies or fragments thereof that are specific to a sequence of amino acid residues ("binding site" or "epitope"), yet if are cross-reactive to other peptides/proteins, are not toxic at the levels at which they are formulated for administration to human use. The term "binding" refers to a direct association between two molecules, due to, for example, covalent, electrostatic, hydrophobic, and ionic and/or hydrogen-bond interactions under physiological conditions, and including interactions such as salt bridges and water bridges and any other conventional binding means. The term "preferentially binds" means that the binding agent binds to the binding site with greater affinity than it binds unrelated amino acid sequences. Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater than the affinity of the binding agent for unrelated amino acid sequences. The terms "immunoreactive" and "preferentially binds" are used interchangeably herein.

As used herein, the term "affinity" refers to the equilibrium constant for the reversible binding of two agents and is expressed as Kd. Affinity of a binding protein to a ligand such as affinity of an antibody for an epitope can be, for example, from about 100 nanomolar (nM) to about 0.1 nM, from about 100 nM to about 1 picomolar (pM), or from about 100 nM to about 1 femtomolar (fM). As used herein, the term "avidity" refers to the resistance of a complex of two or more agents to dissociation after dilution. Apparent affinities can be determined by methods such as an enzyme linked immunosorbent assay (ELISA) or any other technique familiar to one of skill in the art. Avidities can be determined by methods such as a Scatchard analysis or any other technique familiar to one of skill in the art.

"Epitope" refers to that portion of an antigen or other macromolecule capable of forming a binding interaction with the variable region binding pocket of an antibody. Such binding interactions can be manifested as an intermolecular contact with one or more amino acid residues of one or more CDRs. Antigen binding can involve, for example, a CDR3 or a CDR3 pair or, in some cases, interactions of up to all six CDRs of the $V_H$ and $V_L$ chains. An epitope can be a linear peptide sequence (i.e., "continuous") or can be composed of noncontiguous amino acid sequences (i.e., "conformational" or "discontinuous"). An antibody can recognize one or more amino acid sequences; therefore an epitope can define more than one distinct amino acid sequence. Epitopes recognized by antibodies can be determined by peptide mapping and sequence analysis techniques well known to one of skill in the art. Binding interactions are manifested as intermolecular contacts with one or more amino acid residues of a CDR. TRC105 is a murine antibody which is the same amino acid sequence as murine antibody described as Y4-2F1 or SN6j in U.S. Pat. Nos. 5,928,641; 6,200,566; 6,190,660; and 7,097,836. Epitopes recognized by Y4-2F1 and SN6j, and thus TRC105, have been previously identified.

The term "specific" refers to a situation in which an antibody will not show any significant binding to molecules other than the antigen containing the epitope recognized by the antibody. The term is also applicable where, for example, an antigen binding domain is specific for a particular epitope which is carried by a number of antigens, in which case the antibody will be able to bind to the various antigens carrying the epitope. The terms "preferentially binds" or "specifically binds" mean that the antibodies bind to an epitope with greater affinity than it binds unrelated amino acid sequences, and, if cross-reactive to other polypeptides containing the epitope, are not toxic at the levels at which they are formulated for administration to human use. In one aspect, such affinity is at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater than the affinity of the antibody for unrelated amino acid sequences. The terms "immunoreactive," "binds," "preferentially binds" and "specifically binds" are used interchangeably herein. The term "binding" refers to a direct association between two molecules, due to, for example, covalent, electrostatic, hydrophobic, and ionic and/or hydrogen-bond interactions under physiological conditions, and includes interactions such as salt bridges and water bridges, as well as any other conventional means of binding.

"Isolated" (used interchangeably with "substantially pure") when applied to polypeptides means a polypeptide or a portion thereof which, by virtue of its origin or manipulation: (i) is present in a host cell as the expression product of a portion of an expression vector; or (ii) is linked to a protein or other chemical moiety other than that to which it is linked in nature; or (iii) does not occur in nature, for example, a protein that is chemically manipulated by appending, or adding at least one hydrophobic moiety to the protein so that the protein is in a form not found in nature. By "isolated" it is further meant a protein that is: (i) synthesized chemically; or (ii) expressed in a host cell and purified away from associated and contaminating proteins. The term generally means a polypeptide that has been separated from other proteins and nucleic acids with which it naturally occurs. Typically, the polypeptide is also separated from substances such as antibodies or gel matrices (polyacrylamide) which are used to purify it.

Angiogenesis Terminology

As used herein, the terms "angiogenesis inhibitory," "angiogenesis inhibiting" or "anti-angiogenic" include inhibition of vasculogenesis, and are intended to mean affecting a decrease in the extent, amount, or rate of neovascularization. Effecting a decrease in the extent, amount, or rate of endothelial cell proliferation or migration in the tissue is a specific example of inhibiting angiogenesis.

The term "angiogenesis inhibitory composition" refers to a composition which inhibits angiogenesis-mediated processes such as endothelial cell migration, proliferation, tube formation and subsequently leading to the inhibition of the generation of new blood vessels from existing ones, and consequently affects angiogenesis-dependent conditions.

As used herein, the term "angiogenesis-dependent condition" is intended to mean a condition where the process of angiogenesis or vasculogenesis sustains or augments a pathological condition or beneficially influences normal physiological processes. Therefore, treatment of an angiogenesis-dependent condition in which angiogenesis sustains a pathological condition could result in mitigation of disease, while treatment of an angiogenesis-dependent condition in which angiogenesis beneficially influences normal physiological processes could result in, e.g., enhancement of a normal process.

Angiogenesis is the formation of new blood vessels from pre-existing capillaries or post-capillary venules. Vasculogenesis results from the formation of new blood vessels arising from angioblasts which are endothelial cell precursors. Both processes result in new blood vessel formation and are included in the meaning of the term angiogenesis-dependent conditions. The term "angiogenesis" as used herein is intended to include de novo formation of vessels such as that arising from vasculogenesis as well as those arising from branching and sprouting of existing vessels, capillaries and venules. Angiogenesis can also be inclusive of induction of ALK1 signaling and related Smad 1/5/8 phosphorylation and/or signaling. CD105 is also known to be involved in the ALK1 signaling pathway and is thus also included within the meaning of angiogenesis.

Tumor-initiating $CD105^+$ cell populations have been found in human renal carcinomas. The $CD105^+$ cells presented the characteristic of tumor stem cells previously described for cancer stem cells present in other tumor types. The CD105+ cells observed were clonogenic, expressed stem cell markers and lacked differentiative markers, could differentiate in vitro into epithelial and endothelial cell types and could generate in vivo serially transplantable tumors. The tumors, despite being derived from clones expressing mesenchymal markers, are epithelial carcinomas as the tumor of origin and are characterized by the maintenance of a $CD105^+$ tumorigenic population and by the presence of a non-tumorigenic differentiated CD105– population.

"Inducing a host immune response" means that a patient experiences alleviation or reduction of signs or symptoms of illness, and specifically includes, without limitation, prolongation of survival.

As used herein, the terms "proliferative disorder" and "proliferative condition" mean any pathological or non-pathological physiological condition characterized by aberrant or undesirable proliferation. The terms "cell proliferative disorder" and "cell proliferative condition" mean any pathological or non-pathological physiological condition characterized by aberrant or undesirable cell proliferation, as well as including conditions characterized by undesirable or unwanted cell proliferation or cell survival (e.g., due to deficient apoptosis), conditions characterized by deficient or aberrant or deficient apoptosis, as well as conditions characterized by aberrant or undesirable or unwanted cell survival. The term "differentiative disorder" means any pathological or non-pathological physiological condition characterized by aberrant or deficient differentiation.

Proliferative or differentiative disorders amenable to treatment include diseases conditions, benign and neoplastic, characterized by abnormal or undesirable cell numbers, cell growth or cell survival. Such disorders or conditions may therefore constitute a disease state and include all types of cancerous growths or oncogenic processes, metastatic tissues or malignantly transformed cells, tissues, or organs.

Cells comprising the proliferative or differentiative disorder may be aggregated in a cell mass or be dispersed. A "non-solid tumor" refers to neoplasias of the hematopoietic system, such as lymphomas, myelomas and leukemias, or neoplasias that are diffuse in nature, as they do not typically form a solid mass. Particular examples of leukemias include for example, acute and chronic lymphoblastic, myeloblastic and multiple myeloma.

The term "solid tumor" refers to neoplasias or metastases that typically aggregate together and form a mass. Such disorders include neoplasms or cancers, which can affect virtually any cell or tissue type, e.g., carcinoma, sarcoma, melanoma, metastatic disorders or hematopoietic neoplastic disorders. A metastatic tumor can arise from a multitude of primary tumor types, including but not limited to breast, lung, thyroid, head and neck, brain, lymphoid, gastrointestinal (mouth, esophagus, stomach, small intestine, colon, rectum), genito-urinary tract (uterus, ovary, cervix, bladder, testicle, penis, prostate), kidney, pancreas, liver, bone, muscle, skin, etc.

Carcinomas refer to malignancies of epithelial or endocrine tissue, and include respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from the cervix, lung, prostate, breast, head and neck, colon, liver and ovary. The term also includes carcinosarcomas, e.g., which include malignant tumors composed of carcinomatous and sarcomatous tissues. Adenocarcinoma includes a carcinoma of a glandular tissue, or in which the tumor forms a gland like structure.

A cancerous tissue to be treated is, for example, an endothelial tissue or transformed cell expressing an abnormal level of CD105. As used herein, the term "transformed cells" refers to cells that have spontaneously converted to a state of unrestrained growth, i.e., they have acquired the ability to grow through an indefinite number of divisions in culture. Transformed cells may be characterized by such terms as neoplastic, anaplastic and/or hyperplastic, with respect to their loss of growth control. For purposes of this invention, the terms "transformed phenotype of malignant mammalian cells" and "transformed phenotype" are intended to encompass, but not be limited to, any of the following phenotypic traits associated with cellular transformation of mammalian cells: immortalization, morphological or growth transformation, and tumorigenicity, as detected by prolonged growth in cell culture, growth in semi-solid media, or tumorigenic growth in immuno-incompetent or syngeneic animals.

The term "tumor cell antigen" is defined herein as an antigen that is present in higher quantities on a tumor cell or in body fluids than unrelated tumor cells, normal cells, or in normal body fluid. The antigen presence may be tested by any number of assays known to those skilled in the art and include without limitation negative and/or positive selection with antibodies, such as an ELISA assay, a radioimmunoassay, or by Western Blot.

The terms "apoptosis" or "programmed cell death," refers to the physiological process by which unwanted or useless cells are eliminated during development and other normal biological processes. Apoptosis is a mode of cell death that occurs under normal physiological conditions and the cell is an active participant in its own demise ("cellular suicide"). It is most often found during normal cell turnover and tissue homeostasis, embryogenesis, induction and maintenance of immune tolerance, development of the nervous system and endocrine-dependent tissue atrophy. Cells undergoing apoptosis show characteristic morphological and biochemical features. These features include chromatin aggregation, nuclear and cytoplasmic condensation, partition of cytoplasm and nucleus into membrane bound vesicles (apoptotic bodies), which contain ribosomes, morphologically intact mitochondria and nuclear material. In vivo, these apoptotic bodies are rapidly recognized and phagocytized by macrophages, dendritic cells or adjacent epithelial cells. Due to this efficient mechanism for the removal of apoptotic cells in vivo no inflammatory response is elicited. In vitro, the apoptotic bodies as well as the remaining cell fragments ultimately swell and finally lyse. This terminal phase of in vitro cell death has been termed "secondary necrosis." Apoptosis can be measured by methods known to those skilled in the art like DNA fragmentation, exposure of Annexin V, activation of caspases, release of cytochrome c, etc. A cell that has been induced to die is termed herein as an "apoptotic cell."

"Apoptosis inducing agent" is defined herein to induce apoptosis/programmed cell death, and include, for example, anti-CD105 antibodies, anti-VEGF antibodies, irradiation, chemotherapeutic agents or receptor ligation agents, wherein cells, for example, tumor cells or endothelial cells are induced to undergo programmed cell death. Exemplary apoptosis inducing agents are described in more detail below.

Apoptosis can be tested using a standard Annexin V Apoptosis Assay: NIH:OVCAR-3 cells are grown in 6-well plates (NUNC) and irradiated or treated with an antagonist (or in combination with another anti-cancer drug) for 4-48 hours, washed and stained with Annex in V-FITC (BD-Pharmingen) for 1 hour. Cells are analyzed by flow cytometry (Becton-Dickinson, CellQuest), counterstained with Propidium Iodide and analyzed again in the flow cytometer.

Methods of Making and Expressing Antibodies

Chimeric immunoglobulins have been constructed by means of generic engineering. Most chimeric immunoglobulins that have been previously described have comprised a VH and VL from a mouse monoclonal antibody and a CL and Fc of a human antibody. Fc regions can be used from any of the isotypes described herein. As described herein, chimeric can also include criteria by which a limited number of amino acids in the framework of the light chain variable region and/or the heavy chain variable chain are modified in order to increase the affinity of an antibody.

Chimeric antibodies generally have several potential advantages over mouse antibodies for use in human therapy. Because the effector portion of an antibody is human, it is believed to interact better with the other parts of the human immune system (e.g., destroy the target cells more efficiently by complement-dependent cytotoxicity (CDC) or antibody-dependent cellular cytotoxicity (ADCC)). Additionally, the human immune system should not recognize the constant region of the chimeric antibody as foreign, and therefore the antibody response against such an injected antibody should, typically, be less than against a totally foreign mouse antibody. Finally, mouse antibodies are known to have a half-life in the human circulation that is much shorter than the half-life of human antibodies. Chimeric antibodies can, presumably, have a half-life more similar to naturally-occurring human antibodies, allowing smaller and less frequent doses to be given.

When increased affinity of an antibody is desired, residues within the CDRs of an antibody may be additionally substituted with other amino acids. Typically, no more than four amino acid residues in a CDR are changed, and most typically no more than two residues in the CDR will be changed, except for heavy chain CDR2, where as many as 10 residues may be changed. Changes in affinity can be measured by conventional methods such as those described herein (e.g., Biacore).

Antibodies can be constructed and produced using conventional techniques known in the art. In addition, recombinantly prepared antibodies can often be produced in large quantities, particularly when utilizing high level expression vectors.

For veterinary uses, an antibody can be synthesized for administration to a non-human (e.g., a primate, a cow, a horse, a pig, etc.) by using a non-human Fc.

Art-recognized techniques such as those provided and incorporated herein, can be used to modify nucleotides encoding amino acid sequences using recombinant techniques in restriction endonuclease sites.

For expression, an expression system is one which utilizes the GS system (Lonza) using a glutamine synthetase gene as the selectable marker. Briefly, a transfection is performed in CHO cells by electroporation (250V) using the GS system (Lonza) using the glutamine synthetase gene as the selectable marker. Wild type CHO cells are grown in DMEM (Sigma) containing 10% dialyzed Fetal Calf Serum (FCS) with 2 mM glutamine. $6 \times 10^7$ CHO cells are transfected with 300 µg of linearized DNA by electroporation. After electroporation the cells are resuspended in DMEM with glutamine and plated out into 36×96-well plates (50 µl/well), and incubated at 37° C. in 5% $CO_2$. The following day, 150 µl/well of selective medium (DMEM without glutamine) is added. After approximately 3 weeks the colonies are screened by ELISA (see below) using an irrelevant antibody as a negative control. All colonies producing >20 µg/ml are expanded into 24-well plates and then into duplicate T25 flasks.

For high level production, a widely used mammalian expression system is one which utilizes the gene amplification procedure offered by dehydrofolate reductase deficient ("dhfr-") Chinese hamster ovary cells. The system is based upon the dehydrofolate reductase "dhfr" gene, which encodes the DHFR enzyme, which catalyzes conversion of dehydrofolate to tetrahydrofolate. In order to achieve high production, dhfr-CHO cells are transfected with an expression vector containing a functional DHFR gene, together with a gene that encodes a desired protein. In this case, the desired protein is recombinant antibody heavy chain and/or light chain.

By increasing the amount of the competitive DHFR inhibitor methotrexate (MTX), the recombinant cells develop resistance by amplifying the dhfr gene. In standard cases, the amplification unit employed is much larger than the size of the dhfr gene, and as a result the antibody heavy chain is co-amplified.

When large scale production of the protein, such as the antibody chain, is desired, both the expression level and the stability of the cells being employed are taken into account. In long term culture, recombinant CHO cell populations lose homogeneity with respect to their specific antibody productivity during amplification, even though they derive from a single, parental clone.

The present application provides an isolated polynucleotide (nucleic acid) encoding an antibody or portion thereof as described herein, vectors containing such polynucleotides, and host cells and expression systems for transcribing and translating such polynucleotides into polypeptides.

The present application also provides constructs in the form of plasmids, vectors, transcription or expression cassettes which comprise at least one polynucleotide as above.

The present application also provides a recombinant host cell which comprises one or more constructs as above. A nucleic acid encoding any antibody described herein forms an aspect of the present application, as does a method of production of the antibody, which method comprises expression from encoding nucleic acid therefrom. Expression can conveniently be achieved by culturing under appropriate conditions recombinant host cells containing the nucleic acid. Following production by expression, an antibody or a portion thereof can be isolated and/or purified using any suitable technique, then used as appropriate.

Specific antibodies (or portions thereof) encoding nucleic acid molecules and vectors containing same described herein can be provided isolated and/or purified, e.g., from their natural environment, in substantially pure or homogeneous form. In the case of nucleic acid, free or substantially free of nucleic acid or genes origin other than the sequence encoding a polypeptide with the required function. Nucleic acid sequences can comprise DNA or RNA and can be wholly or partially synthetic. Methods of purification are well known in the art.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include, but are not limited to, Chinese hamster ovary cells, HeLa cells, baby hamster kidney cells, NS0 mouse myeloma cells and many others.

A wide variety of unicellular host cells are also useful in expressing the DNA sequences. These hosts include well-known eukaryotic and prokaryotic hosts, such as strains of *E. coli, Pseudomonas, Bacillus, Streptomyces*, fungi such as yeasts, and animal cells, such as CHO, YB/20, NS0, SP2/0, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

The expression of antibodies or portions thereof in prokaryotic cells such as *E. coli* is well established in the art. For a review, see for example Plückthun, A. *Bio/Technology* 9: 545-551 (1991).

Expression in eukaryotic cells in culture is also available to those skilled in the art as an option for production of the antibodies described herein, see for recent reviews, for example Raff, M. E. (1993) Curr. Opinion Biotech. 4: 573-576; Trill J. J. et al. (1995) Curr. Opinion Biotech 6: 553-560, each of which is which is incorporated herein by reference in its entirety.

Suitable vectors can be chosen or constructed, containing appropriate regulatory sequences, including promoter sequences, terminator sequences, polyadenylation sequences, enhancer sequences, marker genes and other sequences as appropriate. Vectors can be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. eds., John Wiley & Sons, 1992. The methods disclosures of Sambrook et al. and Ausubel et al. are incorporated herein by reference in their entirety and are well known in the art.

Thus, a further aspect provides a host cell containing nucleic acid as disclosed herein. A still further aspect provides a method comprising introducing such nucleic acid into a host cell. The introduction can employ any available technique. For eukaryotic cells, suitable techniques can include, for example, calcium phosphate transfection, DEAE Dextran, electroporation, liposome-mediated transfection and transduction using retrovirus or other virus, e.g., vaccinia or, for insect cells, baculovirus. For bacterial cells, suitable techniques can include, for example, calcium chloride transformation, electroporation and transfection using bacteriophage.

The introduction can be followed by causing or allowing expression from the nucleic acid, e.g. by culturing host cells under conditions for expression of the gene.

In one embodiment, the nucleic acid is integrated into the genome (e.g., chromosome) of the host cell. Integration can be promoted by inclusion of sequences which promote recombination with the genome, in accordance with standard techniques. Ig enhances can be initialized as needed to maximize expression.

The present application also provides a method which comprises using a construct as stated above in an expression system in order to express the antibodies (or portions thereof) as above.

The present application also relates to isolated nucleic acids, such as recombinant DNA molecules or cloned genes, or degenerate variants thereof, mutants, analogs, or fragments thereof, which encode an antibody that binds CD105.

In a further embodiment, the full DNA sequence of the recombinant DNA molecule or cloned gene of an antibody or portion thereof described herein can be operatively linked to an expression control sequence which can be introduced into an appropriate host. The application accordingly extends to unicellular hosts transformed with the cloned gene or recombinant DNA molecule comprising a DNA sequence encoding the $V_H$, $V_L$, $C_L$ and/or Fc, of the antibody.

Another feature is the expression of the DNA sequences disclosed herein. As is well known in the art, DNA sequences can be expressed by operatively linking them to an expression control sequence in an appropriate expression vector and employing that expression vector to transform an appropriate unicellular host.

Such operative linking of a DNA sequence to an expression control sequence, of course, includes, if not already part of the DNA sequence, the provision of an initiation codon, ATG, in the correct reading frame upstream of the DNA sequence.

Polynucleotides and vectors can be provided in an isolated and/or a purified form (e.g., free or substantially free of polynucleotides of origin other than the polynucleotide encoding a polypeptide with the required function). As used herein, "substantially pure," and "substantially free" refer to a solution or suspension containing less than, for example, about 20% or less extraneous material, about 10% or less extraneous material, about 5% or less extraneous material, about 4% or less extraneous material, about 3% or less extraneous material, about 2% or less extraneous material, or about 1% or less extraneous material.

A wide variety of host/expression vector combinations can be employed in expressing the DNA sequences of this invention. Useful expression vectors, for example, can consist of segments of chromosomal, non-chromosomal and synthetic DNA sequences. Suitable vectors include, but are not limited to, derivatives of SV40 and known bacterial plasmids, e.g., E. coli plasmids col El, Pcr1, Pbr322, Pmb9 and their derivatives, plasmids such as RP4; phage DNAs, e.g., the numerous derivatives of phage λ, e.g., NM989, and other phage DNA, e.g., M13 and filamentous single stranded phage DNA; yeast plasmids such as the 2u plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Also provided herein is a recombinant host cell which comprises one or more polynucleotide constructs. A polynucleotide encoding an antibody as provided herein forms an aspect of the present application, as does a method of production of the antibody which method comprises expression from one or more polynucleotides. Expression can be achieved, for example, by culturing under appropriate conditions recombinant host cells containing the polynucleotide. An antibody can then be isolated and/or purified using any suitable technique, and used as appropriate.

Any of a wide variety of expression control sequences—sequences that control the expression of a DNA sequence operatively linked to it—can be used in these vectors to express the DNA sequences. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast alpha-mating factors, and other sequences known to control the expression of genes of prokaryotic or eukaryotic cells or their viruses, and various combinations thereof.

It will be understood that not all vectors, expression control sequences and hosts will function equally well to express the DNA sequences. Neither will all hosts function equally well with the same expression system. However, one skilled in the art will be able to select the proper vectors, expression control sequences, and hosts without undue experimentation to accomplish the desired expression without departing from the scope of this application. For example, in selecting a vector, the host must be considered because the vector must function in it. The vector's copy number, the ability to control that copy number, and the expression of any other proteins encoded by the vector, such as antibiotic markers, will also be considered. One of ordinary skill in the art can select the proper vectors, expression control sequences, and hosts to accomplish the desired expression without departing from the scope of this application. For example, in selecting a vector, the host is considered because the vector functions in it. The vector's copy number, the ability to control that copy number, and the expression of any other proteins encoded by the vector, such as antibiotic markers, can also be considered.

The present application also provides constructs in the form of plasmids, vectors, transcription or expression cassettes as described elsewhere herein which comprise at least one polynucleotide as above. Suitable vectors can be chosen or constructed, containing appropriate regulatory sequences, including promoter sequences, terminator sequences, polyadenylation sequences, enhancer sequences, selectable markers and other sequences as appropriate. Vectors can be plasmids, viral e.g., phage, phagemid, etc., as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. eds., John Wiley & Sons, 1992. The methods and disclosures of Sambrook et al. and Ausubel et al. are incorporated herein by reference.

In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products.

A further aspect provides a host cell containing one or more polynucleotides as disclosed herein. Yet a further aspect provides a method of introducing such one or more polynucleotides into a host cell, any available technique. For eukaryotic cells, suitable techniques can include, for example, calcium phosphate transfection, DEAE Dextran, electroporation, liposome-mediated transfection and transduction using retrovirus or other virus (e.g., vaccinia) or, for insect cells, baculovirus. For bacterial cells, suitable techniques can include, for example calcium chloride transformation, electroporation and transfection using bacteriophages.

The introduction can be followed by causing or allowing expression from the one or more polynucleotides, e.g. by culturing host cells under conditions for expression of one or more polypeptides from one or more polynucleotides. Inducible systems can be used and expression induced by addition of an activator.

In one embodiment, the polynucleotides can be integrated into the genome (e.g., chromosome) of the host cell. Integration can be promoted by inclusion of sequences which promote recombination with the genome, in accordance with standard techniques. In another embodiment, the nucleic acid is maintained on an episomal vector in the host cell.

Methods are provided herein which include using a construct as stated above in an expression system in order to express a specific polypeptide.

Considering these and other factors, a person skilled in the art will be able to construct a variety of vector/expression control sequence/host combinations that will express the DNA sequences on fermentation or in large scale animal culture.

A polynucleotide encoding an antibody or a portion thereof can be prepared recombinantly/synthetically in addition to, or rather than, cloned. The polynucleotide can be designed with the appropriate codons. In general, one will select preferred codons for an intended host if the sequence will be used for expression. The complete polynucleotide can be assembled from overlapping oligonucleotides prepared by standard methods and assembled into a complete coding sequence. See, e.g., Edge, Nature, 292:756 (1981); Nambair et al., Science, 223:1299 (1984); Jay et al., J. Biol. Chem., 259:6311 (1984).

Simultaneous incorporation of the antibody (or portion thereof)—encoding nucleic acids and the selected amino acid position changes can be accomplished by a variety of methods known to those skilled in the art, including for example, recombinant and chemical synthesis.

Anti-CD105 Antibodies

Endoglin (CD105) is expressed on the cell surface as a 180 kDa homodimeric transmembrane protein. The external domain binds TGF-β1 and -3 isoforms with high affinity (50 nM), and the transmembrane and the intracellular domains of CD105 share a 71% sequence similarity with betaglycan. The human CD105 gene is located on chromosome 9q34, identified using fluorescence in situ hybridization, and the coding region contains 14 exons, and two different isoforms (L and S) of CD105 with capacity to bind TGF-β have been characterized. The L-CD105 consists of 633 amino acid residues with 47 amino acid residues in the cytoplasmic tail as opposed to the S-CD105, which consists of 600 amino acid residues with a 14 amino acid cytoplasmic tail. However, L-CD105 is the predominant form. CD105 is constitutively phosphorylated in endothelial cells, mainly on serine and threonine residues, and this phosphorylation is due to the constitutively active TGF-β RII within the cell. TGF-β binding to CD105 results in down-regulation of phosphorylation, similar to effects seen with protein kinase C inhibitors. The human CD105 amino acid sequence contains the tripeptide arginine-glycine-aspartic acid (RGD) located in an exposed region of the extracellular domain. The RGD peptide is a key recognition structure found on ECM proteins such as fibronectin, vitronectin, von Willebrand factor (vWF), type I collagen, and fibrinogen and is recognized by cell surface integrins. Integrin adhesion has been implicated in hemostasis, thrombosis, angiogenesis and inflammation, processes in which the endothelium plays a critical role. (Duff et al., FASEB J., 17:984-992 (2003)).

CD105 is a member of the TGF-β receptor family that is expressed by proliferating endothelial cells. Normal levels of CD105 are needed for endothelial cell proliferation. CD105 expression is increased by cellular hypoxia through the production of hypoxia-inducible factor-1-α (HIF-1-α) and protects hypoxic cells from apoptosis. Several functions of CD105 are associated with TGF-β signaling. TGF-β signals through heterodimeric receptors consisting of serine kinases, receptor I (RI), and receptor II (RII). Binding of TGF-β to the external domains of the receptor unmasks the cytoplasmic RII kinase activity that phosphorylates the TGF-β RI, which can then interact with downstream signalers such as the Smad proteins. CD105 forms part of the TGF-β receptor complex but it can exist independently on the cell surface. In many cells in vitro, CD105 suppresses TGF-β signaling.

CD105 also binds other growth factors such as activin A and bone morphogenic proteins (BMP)-10, -9, -7 and -2. Binding of TGF-β or other growth factor ligands to CD105 requires the presence of at least the receptor RII, and it cannot bind ligands by itself. CD105 association with receptors does not alter their affinity for the ligand itself. Upon association, the cytoplasmic domain of CD105 is phosphorylated by TGF-β RI and TGF-β RII; then TGF-β RI, but not TGF-β RII, kinase dissociates from the receptor complex.

CD105 expression inhibits phosphorylation levels of TGF-β RII but increases that of TGF-β RI, resulting in increased phosphorylation of Smad 2 but not Smad 3. Since Smad 2 can interact with a variety of transcription factors, co-activators, and suppressors, phosphorylated Smad 2 may act as an integrator of multiple signals to modulate gene transcription. Thus, CD105 modulates TGF-β functions via interaction with TGF-β RI and TGF-β RII and modifies the phosphorylation of downstream Smad proteins.

CD105 acts to modulate signaling of multiple kinase receptor complexes of the TGF-β superfamily, including TGF-β receptors (TGF-βR), activin receptor-like kinases (ALK) and activin receptors. In the absence of CD105, activation of TGF-β receptors results in phosphorylation of SMAD proteins (SMAD 2 and 3) that inhibit endothelial cell growth. However, activation of CD105 by TGF-β modulates SMAD protein phosphorylation (including the phosphorylation of SMAD 1, 5 and 8). The end result is release of the growth inhibitory effects of TGF-β receptor activation on endothelial cells (see FIG. 2). Not surprisingly, prevention of CD105 activation by anti-CD105 antibody or antisense oligonucleotide acts synergistically with TGF-β to suppress endothelial cell growth.

The CD105 promoter is 2.6 kb in length but does not contain TATA or CAAT transcription initiation boxes. However, it has two GC-rich regions, consensus motifs for Sp1, ets, GATA, AP-2, NGF-β, and Mad, as well as TGF-β response elements. Nonetheless, CD105 has a relatively restricted cellular distribution. The basal level of transcription appears to require an ets site at position −68 and the Sp1 sites, but the relative restriction of expression, for example, to endothelial cells, appears to involve multiple regulatory regions, in particular, one at −1294 to −932 and another very close to the transcription initiation site. CD105 is up-regulated by TGF-β, and this has been shown to require a Sp1 site at −37 to −29, also involving one or more juxta-posed upstream SBE sites binding Smads 3 and/or 4 (which are activated by TGF-β signaling). Hypoxia is a common feature of ischemic tissues and tumors, and is a potent stimulator for CD105 gene expression in vascular endothelial cells (ECs). Such an effect is potentiated in combination with TGF-β1. The up-regulated CD105 can exert a self-protective role in ECs under hypoxic stress.

Vascular EC are the major source of CD105. Other cell types including vascular smooth muscle cells, fibroblasts, macrophages, leukemic cells of pre-B and myelomonocytic origin, and erythroid precursors express CD105 to a lesser extent.

CD105 is involved in angiogenesis. Antisense experiments have demonstrated that suppression of CD105 expression in HUVEC results in marked inhibition of in vitro angiogenesis in combination with TGF-β1, indicating that CD105 is a proangiogenic component in the endothelial cells. Further evidence of the important role of CD105 in angiogenesis comes from CD105 knockout mice. The CD105 null mice exhibit multiple vascular and cardiac defects leading to death at an early embryonic stage. Severe vascular impairments observed in CD105 null mice indicate that CD105 is required for the formation of mature blood vessels in the extraembryonic vasculature, further confirming the direct role of CD105 in angiogenesis.

CD105, also known as, inter alfa, endoglin or edg-1, is a type I homodimeric membrane glycoprotein which is expressed at high levels in proliferating vascular endothelial cells. Thus, CD105 is primarily a proliferation-associated marker for endothelial cells undergoing active angiogenesis. However, there may be limited expression of CD105 by the vascular endothelium of normal tissues. Human CD105 is known to specifically bind transforming growth factor-β (TGF-β), and the deduced amino acid sequence of CD105 has strong homology to β-glycan, a type of TGF-β receptor.

CD105 has been targeted in antibody-based methods of reducing tumor vasculature, as CD105 is a proliferation-associated antigen on endothelial and leukemia cells. Its expression is up-regulated in tumor-associated vascular endothelium, and CD105 is essential for angiogenesis. Angiogenesis includes the formation of new capillary blood vessels leading to neovascularization as well as the maintenance of the existing vasculature. It is a complex process which includes a series of sequential steps including endothelial cell-mediated degradation of vascular basement membrane and interstitial matrices, migration of endothelial cells, proliferation of endothelial cells, and formation of capillary loops by endothelial cells.

CD105 can be found on cells that comprise and support existing vasculature as well as cells that are promoting the growth of, and become part of, new vasculature. These antibodies can bind CD105 and thereby inhibit angiogenesis, inhibit the existing vasculature or the maintenance of the existing vasculature, and/or inhibit small vessel dilation. In addition to their use for purification of CD105, these antibodies are useful for purification, detection and diagnostic purposes as well as therapeutic purposes. The antibodies provided herein can be used for the formulation of medicaments for the treatment a variety of conditions and diseases, methods to treat said conditions and diseases and methods of detection or diagnosis. As used herein, angiogenesis is inclusive of the growth and/or development of new blood vessels (also referred to as neovascularization), dilation of the small vessels, excessive or prolonged vascular growth, and maintenance of the existing vasculature. Angiogenic conditions and diseases refer to those diseases and conditions related to, caused by, or associated with angiogenesis. Non-limiting examples of such diseases include, for example, various forms of cancer (primary tumors and metastases). Murine monoclonal antibodies (mAbs) have been raised against CD105 which modulate CD105 activity and thereby inhibit angiogenesis and/or inhibit vasodilation of small blood vessels. These murine antibodies are described in U.S. Pat. Nos. 5,928,641, 6,200,566, 6,190,660, and 7,097,836, each of which is hereby incorporated in their entirety. Additionally, the ex vivo and in vivo efficiency of a number of these antibodies has been demonstrated; monoclonal antibodies that bind CD105 are of interest as CD105 modulating compounds. Therapeutic use of murine antibodies is not feasible, however, as administration of the murine antibodies has a number of limitations, including immunogenicity in, for example, the form of human anti-mouse antibodies (HAMA).

Several anti-CD105 antibodies, in particular anti-CD105 monoclonal antibodies ("mAb"), have been described. MAb SN6 is an antibody generated from immunization of mice with glycoprotein mixtures of cell membranes of human leukemia cells (Haruta and Seon, 1986, *Proc. Natl. Acad. Sci.* 83:7898-7902). SN6 is a murine mAb that recognizes human CD105. MAb 44G4 is an antibody generated from immunization of mice with whole cell suspensions of human pre-B leukemia cells (Gougos and Letarte, 1988, *J. Immunol.* 141:1925-1933; 1990, *J. Biol. Chem.* 265:8361-8364). 44G4 is also a murine mAb that recognizes human CD105. MAb MJ7/18 is an antibody generated from immunization of rats with inflamed mouse skins (Ge and Butcher, 1994, supra). MJ7/18 is also a mAb that recognizes murine CD105. mAb Tec-11 is an antibody generated from immunization of mice with human umbilical vein endothelial cells (Burrows et al., 1995, *Clin. Cancer Res.* 1:1623-1634). Tec-11 is a murine mAb with reactivity restricted to human CD105. Chimeric antibodies that bind CD105 are described herein that exhibit reduced immunogenicity while maintaining and/or improving their specificity. Additionally, to address problems associated with murine antibodies, chimeric antibodies that bind CD105 and decrease and/or inhibit angiogenesis are described herein that exhibit reduced immunogenicity while maintaining and/or improving their specificity. These anti-CD105 antibodies are useful for the diagnosis and treatment of various conditions and diseases as well as for purification and detection of CD105. Antibodies against CD105 represent an important area for the development of therapies for the treatment of a variety of diseases and conditions which involve, are influenced by, or affected by angiogenesis.

Provided herein are antibodies thereof that bind to CD105. Also provided are antibodies, (or antigen-binding fragments) thereof that bind CD105 and inhibit (partially or fully) or manage/treat (partially or fully) angiogenesis/neovascularization, dilation of small vessels, inhibition of cell proliferation or inhibition or tumor growth. Similarly, inhibition of CD105 function (e.g., signaling, binding, activation, and the like) is also included within the meaning of inhibiting or binding CD105. In yet another embodiment, an antibody inhibits angiogenesis by binding to CD105. The application also provides cell lines which can be used to produce the antibodies, methods for producing the cell lines, methods for expressing antibodies and purifying the same.

One can recognize that the antibodies that specifically bind CD105 generated using the methods described herein can be tested using the assays provided herein or known in the art for the ability to bind to CD105 using conventional methods including, but not limited to, ELISA. Affinity of antibodies described herein can also be determined using conventional methods including, but not limited to, Biacore or surface plasmon resonance.

Provided herein are antibodies that bind CD105. Also provided herein are antibodies that bind CD105 and inhibit angiogenesis.

Provided herein is an antibody comprising a light chain variable region having an amino acid sequence set forth as SEQ ID NO: 1, a light chain constant region having an amino acid sequence set forth as SEQ ID NO: 2, a heavy chain variable region having an amino acid sequence set forth as SEQ ID NO: 3 and a gamma 1 (γ1) constant region (Fc) having an amino acid sequence set forth as SEQ ID NO: 4. set forth as SEQ ID NO: 3; and a constant region (Fc) having an amino acid sequence set forth as SEQ ID NO: 4.

In another non-limiting embodiment, the anti-CD105 antibody comprises a $V_L$ CDR1 having an amino acid sequence set forth as SEQ ID NO: 5; a $V_L$ CDR2 having an amino acid sequence set forth as SEQ ID NO: 6; a $V_L$ CDR3 having an amino acid sequence set forth as SEQ ID NO: 7; a VH CDR1 having an amino acid sequence set forth as SEQ ID NO: 8; a $V_H$ CDR2 having an amino acid sequence set forth as SEQ ID NO: 9; and a $V_H$ CDR3 having an amino acid sequence set forth as SEQ ID NO: 10.

In another non-limiting embodiment, an isolated humanized, de-immunized anti-CD105 antibody can comprise a heavy chain variable region having the amino acid sequence set forth as SEQ ID NO: 11 and a light chain variable region having the amino acid sequence set forth as SEQ ID NO: 12. Other non-limiting examples of humanized-deimmunized heavy chains include, but are not limited to, SEQ ID NOS: 13, 14, 15 and 16. Other non-limiting examples of humanized-deimmunized light chains include, but are not limited to, SEQ ID NOS: 17, 18, 19, 20, 21, 22, and 23. The sequences are provided below in Example 17.

In another aspect, the present application provides an antibody capable of competing with an anti-CD105 antibody described herein under conditions in which at least 5% of an antibody having the $V_H$ and $V_L$ sequences of the antibody is blocked from binding to CDI 05 by competition with such an antibody in an ELISA assay.

Provided herein are neutralizing antibodies that bind to CD105 and modulate the activity of CD105. The neutralizing antibody can for example, inhibit angiogenesis by binding to CD105.

Antibodies described herein are useful in detection or diagnostic applications as described in more detail below. Antibodies described herein are useful for binding to CD105, which, in turn, can inhibit angiogenesis as described herein.

Antibodies described herein can further comprise a therapeutic moiety for use in therapeutic applications.

Antibodies described herein can also be used as immunoconjugates. As used herein, for purposes of the specification and claims, immunoconjugates refer to conjugates comprised of the anti-CD105 antibodies or fragments thereof according to the present invention and at least one therapeutic label. Therapeutic labels include antitumor agents and angiogenesis-inhibitors. Such antitumor agents are known in the art and include, but not limited to, toxins, drugs, enzymes, cytokines, radionuclides, photodynamic agents, and angiogenesis inhibitors. Toxins include, but are not limited to, ricin A chain, mutant *Pseudomonas* exotoxins, diphtheria toxoid, streptonigrin, boamycin, saporin, gelonin, and pokeweed antiviral protein. Drugs include daunorubicin, methotrexate, and calicheamicins. Radionuclides include radiometals. Cytokines include, but are not limited to, transforming growth factor (TGF)-β, interleukins, interferons, and tumor necrosis factors. Photodynamic agents include, but are not limited to, porphyrins and their derivatives. Additional therapeutic labels will be known in the art and are also contemplated herein. The methods for complexing the anti-CD105 mAbs or a fragment thereof with at least one antitumor agent are well known to those skilled in the art (i.e., antibody conjugates as reviewed by Ghetie et al., 1994, *Pharmacol. Ther.* 63:209-34). Such methods may utilize one of several available heterobifunctional reagents used for coupling or linking molecules. Additional radionuclides are further described herein along with additional methods for linking molecules, such as therapeutic and diagnostic labels.

Antibodies can be modified using techniques known in the art for various purposes such as, for example, by addition of polyethylene glycol (PEG). PEG modification (PEGylation) can lead to one or more of improved circulation time, improved solubility, improved resistance to proteolysis, reduced antigenicity and immunogenicity, improved bioavailability, reduced toxicity, improved stability, and easier formulation (for a review see, Francis et al., International Journal of Hematology 68:1-18, 1998).

Fc portions of antibodies can be modified to increase half-life of the in circulation in blood when administered to a patient. Modifications can be determined using conventional means in the art such as, for example, described in U.S. Pat. No. 7,217,798, which is hereby incorporated by reference in its entirety.

Other methods of improving the half-life of antibody-based fusion proteins in circulation are also known such as, for example, described in U.S. Pat. Nos. 7,091,321 and 6,737,056, each of which is hereby incorporated by reference. Additionally, antibodies may be produced or expressed so that they do not contain fucose on their complex N-glycoside-linked sugar chains. The removal of the fucose from the complex N-glycoside-linked sugar chains is known to increase effector functions of the antibodies and antigen-binding fragments, including but not limited to, antibody dependent cell-mediated cytotoxicity (ADCC) and complement dependent cytotoxicity (CDC). Similarly, antibodies that can bind CD105 can be attached at their C-terminal end to all or part of an immunoglobulin heavy chain derived from any antibody isotype, e.g., IgG, IgA, IgE, IgD and IgM and any of the isotype sub-classes, particularly IgG1, IgG2b, lgG2a, lgG3 and IgG4.

Additionally, the antibodies described herein can also be modified so that they are able to cross the blood-brain barrier. Such modification of the antibodies described herein allows for the treatment of brain diseases such as glioblastoma multiforme (GBM). Exemplary modifications to allow proteins such as antibodies to cross the blood-brain barrier are described in US Patent Publication 20070082380 which is hereby incorporated by reference in its entirety.

Glycosylation of immunoglobulins has been shown to have significant effects on their effector functions, structural stability, and rate of secretion from antibody-producing cells (Leatherbarrow et al., *Mol. Immunol.* 22:407 (1985)). The carbohydrate groups responsible for these properties are generally attached to the constant (C) regions of the antibodies. For example, glycosylation of IgG at asparagine 297 in the $C_H 2$ domain is required for full capacity of IgG to activate the classical pathway of complement-dependent cytolysis (Tao and Morrison, *J. Immunol.* 143:2595 (1989)). Glycosylation of IgM at asparagine 402 in the $C_H 3$ domain is necessary for proper assembly and cytolytic activity of the antibody (Muraoka and Shulman, *J. Immunol.* 142:695 (1989)). Removal of glycosylation sites as positions 162 and 419 in the $C_H 1$ and $C_H 3$ domains of an IgA antibody led to intracellular degradation and at least 90% inhibition of secretion (Taylor and Wall, *Mol. Cell. Biol.* 8:4197 (1988)). Additionally, antibodies may be produced or expressed so that they do not contain fucose on their complex N-glycoside-linked sugar chains. The removal of the fucose from the complex N-glycoside-linked sugar chains is known to increase effector functions of the antibodies and antigen-binding fragments, including but not limited to, antibody dependent cell-mediated cytotoxicity (ADCC) and complement dependent cytotoxicity (CDC). These "defucosylated" antibodies may be produced through a variety of systems utilizing molecular cloning techniques known in the art, including but not limited to, transgenic animals, transgenic plants, or cell-lines that have been genetically engineered so that they no longer contain the enzymes and biochemical pathways necessary for the inclusion of a fucose in the complex N-glycoside-linked sugar chains (also known as fucosyltransferase knock-out animals, plants, or cells). Non-limiting examples of cells that can be engineered to be fucosyltransferase knock-out cells include CHO cells, SP2/0 cells, NS0 cells, and YB2/0 cells.

Glycosylation of immunoglobulins in the variable (V) region has also been observed. Sox and Hood reported that about 20% of human antibodies are glycosylated in the V region (*Proc. Natl. Acad. Sci. USA* 66:975 (1970)). Glycosylation of the V domain is believed to arise from fortuitous occurrences of the N-linked glycosylation signal Asn-Xaa-Ser/Thr in the V region sequence and has not been recognized in the art as playing a role in immunoglobulin function.

Glycosylation at a variable domain framework residue can alter the binding interaction of the antibody with antigen. The present invention includes criteria by which a limited number of amino acids in the framework or CDRs of an immunoglobulin chain are chosen to be mutated (e.g., by substitution, deletion, or addition of residues) in order to increase the affinity of an antibody.

Affinity for binding an antigen can, generally, be modulated by introducing one or more mutations into the V region framework, typically in areas adjacent to one or more CDRs and/or in one or more framework regions. Typically, such mutations involve the introduction of conservative amino acid substitutions that either destroy or create the glycosylation site sequences but do not substantially affect the hydropathic structural properties of the polypeptide. Typically, mutations that introduce a proline residue are avoided. Glycosylation of antibodies is further described in U.S. Pat. No. 6,350,861, which is incorporated by reference herein with respect to glycosylation.

Antibodies can be formulated for short-term delivery or extended (long term) delivery.

Antibodies that bind to CD105 can also be used for purification of CD105 and/or to detect CD105 levels in a sample or patient to detect or diagnose a disease or disorder associated with CD105 as described in more detail below.

Antibodies which bind CD105 generated using such methods can be tested for one or more of their binding affinity, avidity, and neutralizing capabilities. Useful antibodies can be used to administer a patient to prevent, inhibit, manage or treat a condition disease or disorder associated with angiogenesis.

Antibodies can be evaluated for one or more of binding affinity, association rates, disassociation rates and avidity. In one aspect, antibodies can be evaluated for their ability to neutralize the activity of CD105 or VEGF. Measurement binding affinity, association rates, disassociation rates and avidity can be accomplished using art-recognized assays including, but not limited to, an enzyme-linked-immunosorbent assay (ELISA), Scatchard Analysis, BIACORE analysis (Surface Plasmon Resonance), etc., as well as other assays commonly used and known to those of ordinary skill in the art.

Measurement of binding of antibodies to CD105 and/or the ability of the antibodies, for example, to inhibit angiogenesis, can be determined using, for example, an enzyme-linked-immunosorbent assay (ELISA), a competitive binding assay, an ELISPOT assay, or any other useful assay known in the art. These assays are commonly used and well-known to those of ordinary skill in the art.

In one non-limiting embodiment, an ELISA assay can be used to measure the binding capability of specific antibodies that bind to CD105.

Assays, such as an ELISA, also can be used to identify antibodies thereof which exhibit increased specificity for CD105 in comparison to other antibodies thereof. Assays, such as an ELISA, also can be used to identify antibodies thereof with bind to epitopes across one or more polypeptides and across one or more species of CD105 or VEGF. The specificity assay can be conducted by running parallel ELISAs in which a test antibody is screened concurrently in separate assay chambers for the ability to bind one or more epitopes on different species of the polypeptide containing the CD105 epitopes to identify antibodies thereof that bind to CD105. Another technique for measuring apparent binding affinity familiar to those of skill in the art is a surface plasmon resonance technique (analyzed on a BIACORE 2000 system) (Liljeblad, et al., *Glyco. J.* 2000, 17:323-329). Standard measurements and traditional binding assays are described by Heeley, R. P., *Endocr. Res.* 2002, 28:217-229.

Antibodies that specifically bind to CD105 can also be assayed for their ability to treat various diseases and conditions associated with angiogenesis in connection with various forms of cancer (e.g., primary tumors, recurring tumors, and metastases). Any suitable assay known to one of skill in the art can be used to monitor such effects. Several such techniques are described herein. In one example, the antibodies described herein are assayed for their ability to bind CD105. In another example, affinity constants for the antibodies described herein are determined by surface plasmon resonance (SPR). In yet another example, the antibodies described herein are assayed for their effect on the inhibition of angiogenesis.

Formulations

Formulations provided herein may include, in addition to active ingredient (anti-CD105 antibodies, or antibody fragments thereof), a pharmaceutically acceptable excipient, carrier, buffer, stabilizer, surfactant or other materials well known to those in the art. Such materials should be non-toxic and should not interfere with the efficacy of the active ingredient(s). The precise nature of the carrier or other material will depend on the route of administration.

Provided herein are new formulations of anti-CD105 antibodies, pre-filled syringes containing the formulations, and the use of such formulations useful for treating angiogenesis-related disorders. The present application provides formulations that may be used for intravenous or intraocular administration of, for example, treatment of cancers associated with CD105 and ophthalmologic conditions. Binding, affinity, avidity and activity of an antibody, or antigen-binding fragment thereof, to CD105 described herein can be assessed using art recognized methods including, but not limited to, assays described supra and below in the Examples.

In one aspect, provided herein is a formulation comprising from about 1 mg/ml to about 150 mg/ml of an anti-CD105 antibody, or antigen-binding fragment thereof, up to about 100 mM buffering agent, up to about 1 M polyol, and a pH of about 4.0 to about 7.5.

In one aspect, the formulation is stable following preparation, which can be tested according to conventional means. Safe handling and administration of formulations comprising proteins represent significant challenges to pharmaceutical formulators. Proteins possess unique chemical and physical properties that present stability problems: a variety of degradation pathways exist for proteins, implicating both chemical and physical instability. Chemical instability includes deamination, aggregation, clipping of the peptide backbone, and oxidation of methionine residues. Physical instability encompasses many phenomena, including, for example, aggregation.

A "stable" formulation is one in which the protein therein essentially retains its physical stability and/or chemical stability and/or biological activity upon storage. Various analytical techniques for measuring protein stability are available in the art and are reviewed in Peptide and Protein Drug Delivery, 247-301, Vincent Lee Ed., Marcel Dekker, Inc., New York, N.Y., Pubs. (1991) and Jones, A. *Adv. Drug Delivery Rev.* 10: 29-90 (1993), for example. Stability can be measured at a selected temperature for a selected time period. Preferably, the formulation is stable at room temperature (about 30° C.) or at 40° C. for at least 1 month and/or stable at about 2-8° C. for at least 1 year, or at least 2 years. Furthermore, the formulation may be stable following freezing (to, e.g., −80° C.) and thawing of the formulation.

A protein "retains its physical stability" in a pharmaceutical formulation if it shows no signs of aggregation, precipitation and/or denaturation upon visual examination of color and/or clarity, or as measured by UV light scattering or by size exclusion chromatography (SEC). Methods for determining such measurements are known in the art and are described in more detail below.

A protein "retains its chemical stability" in a formulation, if the chemical stability at a given time is such that the protein is considered to still retain its biological activity as defined below. Chemical stability can be assessed by detecting and quantifying chemically altered forms of the protein. Chemical alteration may involve size modification (e.g., clipping) which can be evaluated using size exclusion chromatography, SDS-PAGE and/or matrix-assisted laser desorption ionization/time-of-flight mass spectrometry (MALDI/TOF MS), for example. Other types of chemical alteration include charge alteration (e.g., occurring as a result of deamidation) which can be evaluated by ion-exchange chromatography or capillary electrophoresis-isoelectric focusing (cIEF), for example.

An antibody "retains its biological activity" in a formulation, if the biological activity of the antibody at a given time is, for example, within about 50 to 150% (within the errors of the assay) of a biological activity exhibited at the time the formulation was prepared as determined in an antigen binding assay, for example. Other "biological activity" assays for antibodies are elaborated below.

With respect to stability of the formulation over time, at least 95% of the anti CD105 antibody, or antigen-binding fragment thereof, may be present as a monomer following storage at about 2 to 8° C. for at least about 12 months as measured by size exclusion chromatography (SEC). Further art-recognized methods for assessing stability including, but not limited to, those described in the Examples are also contemplated herein.

Further, the anti-CD105 antibody, or antigen-binding fragment thereof, may display about 50 to 150% binding by a CD105 ELISA binding assay after storage at about 2 to 8° C. for at least about 12 months.

The average isoelectric point (pI) of the anti CD105 antibody may be from about 8.8 to about 9.2 after storage at 2 to 8° C. for at least about 12 months, as measured by, for example, capillary electrophoresis-isoelectric focusing.

One would understand that the anti CD105 antibody, or antigen-binding fragment thereof, may be stable for at least about 12 months, at least about 18 months, at least about 24 months, at least about 30 months, at least about 36 months, or more.

A formulation may contain at least 95% of the anti CD105 antibody present as monomer as measured by SEC following freezing and thawing cycles of the formulation. Alternatively, or in addition, a formulation may contain at least 95% of the anti CD105 antibody present as monomer as measured by SEC when subjected to agitation stress.

The anti CD105 antibody, or antigen-binding fragment thereof, may comprise any sequence that of CDRs that are capable of binding to CD105. In one non-limiting embodiment, the anti-CD105 antibody is TRC105, which comprises a light chain variable region (VL) having an amino acid sequence set forth as SEQ ID NO: 1; a light chain constant region (CL) having an amino acid sequence set forth as SEQ ID NO: 2; a heavy chain variable region (VH) having an amino acid sequence set forth as SEQ ID NO: 3; and a constant region (Fc) having an amino acid sequence set forth as SEQ ID NO: 4.

In another non-limiting embodiment, the anti-CD105 antibody comprises a VL CDR1 having an amino acid sequence set forth as SEQ ID NO: 5; a VL CDR2 having an amino acid sequence set forth as SEQ ID NO: 6; a VL CDR3 having an amino acid sequence set forth as SEQ ID NO: 7; a VH CDR1 having an amino acid sequence set forth as SEQ ID NO: 8; a VH CDR2 having an amino acid sequence set forth as SEQ ID NO: 9; and a VH CDR3 having an amino acid sequence set forth as SEQ ID NO: 10.

The formulation may contain from about 1 mg/ml to about 150 mg/ml of an anti-CD105 antibody, or antigen-binding fragment thereof, or any value therein including, but not limited to, about 2 mg/ml, about 5 mg/ml, about 7.5 mg/ml, about 10 mg/ml, 20 mg/ml, about 25 mg/ml, about 30 mg/ml, about 35 mg/ml, about 40 mg/ml, about 45 mg/ml, about 50 mg/ml, about 55 mg/ml, about 60 mg/ml, about 65 mg/ml, about 70 mg/ml, about 75 mg/ml, about 80 mg/ml, about 85 mg/ml, about 90 mg/ml, about 95 mg/ml, about 100 mg/ml, about 105 mg/ml, about 110 mg/ml, about 115 mg/ml, about 120 mg/ml, about 125 mg/ml, about 130 mg/ml, about 135 mg/ml, about 140 mg/ml, about 145 mg/ml, about 150 mg/ml, or more, or any integer therebetween. As used herein, when referring to antibody concentrations, the term "about" means±2% of the indicated value.

In one embodiment, the formulation comprises about 25 mg/ml of the anti-CD105 antibody or, antigen-binding fragment thereof. In another embodiment, the formulation comprises about 50 mg/ml of the anti-CD105 antibody or, antigen-binding fragment thereof. In yet another embodiment, the formulation comprises about 100 mg/ml of the anti-CD105 antibody or, antigen-binding fragment thereof.

Formulations as described herein may contain a buffering agent such as, for example, histidine, acetate, citrate or phosphate. Buffering agents may be included in an amount of about 5 mM to about 100 mM. In one embodiment, the formulation comprises about 5 mM, about 7.5 mM, about 10 mM, about 12.5 mM, about 15 mM, about 17.5 mM, 20 mM, about 22.5 mM, about 25 mM, about 30 mM, about 35 mM, about 40 mM, about 45 mM, about 50 mM, about 55 mM, about 60 mM, about 65 mM, about 70 mM, about 75 mM, about 80 mM, about 85 mM, about 90 mM, about 95 mM, about 100 mM, or any integer therein histidine, acetate, citrate or phosphate. As used herein, when referring to buffer concentrations, the term "about" means±2% of the indicated value.

Formulations may be prepared for any type of administration known for antibodies including, but not limited to, intravitreal and intravenous administration.

Formulations provided herein may further include an acceptable carrier or excipient including any carrier or excipient that is a pharmaceutically acceptable carrier or excipient and which is acceptable for administration to a patient.

In one embodiment, a formulation provided herein is isotonic. Representative isotonic formulations include, but are not limited to, those that are from about 250 to about 350 milliosmolar. In another embodiment, a formulation provided herein is hypertonic. Representative hypertonic formulations include, but are not limited to, those that are from about 351 to about 1000 milliosmolar.

Polyols may be added to a formulation described herein in an amount of up to about 1 M. For example, the formulation may comprise polyol in an amount of about 50 mM, about 75 mM, about 100 mM, about 150 mM, about 200 mM, about 225 mM, about 240 mM, about 250 mM, about 300 mM, about 350 mM, about 400 mM, about 450 mM, about 500 mM, about 550 mM, about 600 mM, about 650 mM, about 700 mM, about 750 mM, about 800 mM, about 850 mM, about 900 mM, about 950 mM, about 1 M, or any integer therein. In one embodiment, a formulation provided herein contains polyol in an amount of less than 300 mM and the formulation is made isotonic with a salt in a concentration of from about 100 mM to about 175 mM. For example, the formulation containing polyol in an amount of less than 300 mM is made isotonic with a salt in a concentration of about 130 mM. As used herein, when referring to polyol concentrations, the term "about" means±2% of the indicated value. In one aspect, a polyol to be used in the formulations provided herein may be a sugar such as, for example, a non-reducing sugar. Representative examples of non-reducing sugars include, but are not limited to, trehalose and sucrose. For example, a formulation may comprise from about 200 mM to about 300 mM trehalose or sucrose. In one embodiment, a formulation may comprise about 240 mM trehalose or sucrose. Alternatively, the sugar may be sorbitol in an amount (concentration) of from about 200 mM to about 300 mM. In one embodiment, a formulation may comprise about 240 mM sorbitol.

Further non-limiting examples of a formulation provided herein is any one of formulations 1-39 of Table 1.

TABLE 1

| Formulation No. | pH | phos (mM) | His (mM) | citrate (mM) | acetate (mM) | NaCl (mM) | trehalose (mM) | sorbitol | Protein mg/mL |
|---|---|---|---|---|---|---|---|---|---|
| F01 | 7 | 20 | 0 | 0 | 0 | 130 | 0 | 0 | 25 |
| F02 | 6 | 20 | 0 | 0 | 0 | 130 | 0 | 0 | 25 |
| F03 | 6 | 0 | 20 | 0 | 0 | 130 | 0 | 0 | 25 |
| F04 | 5 | 0 | 20 | 0 | 0 | 130 | 0 | 0 | 25 |
| F05 | 6 | 0 | 0 | 20 | 0 | 130 | 0 | 0 | 25 |
| F06 | 5 | 0 | 0 | 20 | 0 | 130 | 0 | 0 | 25 |
| F07 | 4 | 0 | 0 | 0 | 20 | 130 | 0 | 0 | 25 |
| F08 | 5 | 0 | 0 | 0 | 20 | 130 | 0 | 0 | 25 |
| F09 | 5 | 0 | 20 | 0 | 0 | 0 | 240 | 0 | 25 |

TABLE 1-continued

| Formulation No. | pH | phos (mM) | His (mM) | citrate (mM) | acetate (mM) | NaCl (mM) | trehalose (mM) | sorbitol | Protein mg/mL |
|---|---|---|---|---|---|---|---|---|---|
| F10 | 5 | 0 | 0 | 20 | 0 | 0 | 240 | 0 | 25 |
| F11 | 5 | 0 | 0 | 0 | 20 | 0 | 240 | 0 | 25 |
| F12 | 6 | 10 | 0 | 0 | 0 | 0 | 240 | 0 | 25 |
| F13 | 6 | 0 | 10 | 0 | 0 | 0 | 240 | 0 | 25 |
| F14 | 6 | 10 | 0 | 0 | 0 | 80 | 120 | 0 | 25 |
| F15 | 6 | 0 | 10 | 0 | 0 | 80 | 120 | 0 | 25 |
| F16 | 7 | 20 | 0 | 0 | 0 | 130 | 0 | 0 | 25 |
| F17 | 6 | 20 | 0 | 0 | 0 | 130 | 0 | 0 | 25 |
| F18 | 6 | 0 | 20 | 0 | 0 | 130 | 0 | 0 | 25 |
| F19 | 5 | 0 | 20 | 0 | 0 | 130 | 0 | 0 | 25 |
| F20 | 6 | 0 | 0 | 20 | 0 | 130 | 0 | 0 | 25 |
| F21 | 5 | 0 | 0 | 20 | 0 | 130 | 0 | 0 | 25 |
| F22 | 4 | 0 | 0 | 0 | 20 | 130 | 0 | 0 | 25 |
| F23 | 5 | 0 | 0 | 0 | 20 | 130 | 0 | 0 | 25 |
| F24 | 5 | 0 | 20 | 0 | 0 | 0 | 240 | 0 | 25 |
| F25 | 5 | 0 | 0 | 20 | 0 | 0 | 240 | 0 | 25 |
| F26 | 5 | 0 | 0 | 0 | 20 | 0 | 240 | 0 | 25 |
| F27 | 6 | 10 | 0 | 0 | 0 | 0 | 240 | 0 | 25 |
| F28 | 6 | 0 | 10 | 0 | 0 | 0 | 240 | 0 | 50 |
| F29 | 6 | 10 | 0 | 0 | 0 | 80 | 120 | 0 | 50 |
| F30 | 6 | 0 | 10 | 0 | 0 | 80 | 120 | 0 | 50 |
| F31 | 7 | 17 | 0 | 0 | 0 | 145 | 0 | 0 | 5 |
| F32 | 7 | 17 | 0 | 0 | 0 | 145 | 0 | 0 | 7 |
| F33 | 5.5 | 0 | 20 | 0 | 0 | 0 | 240 | 0 | 25 |
| F34 | 5.5 | 0 | 20 | 0 | 0 | 0 | 0 | 240 | 25 |
| F35 | 4 | 0 | 0 | 0 | 20 | 0 | 0 | 240 | 25 |
| F36 | 5.5 | 0 | 20 | 0 | 0 | 0 | 240 | 0 | 50 |
| F37 | 4 | 0 | 0 | 0 | 20 | 0 | 240 | 0 | 50 |
| F38 | 5.5 | 0 | 20 | 0 | 0 | 0 | 240 | 0 | 100 |
| F39 | 4 | 0 | 0 | 0 | 20 | 0 | 240 | 0 | 100 | phos: phosphate buffered saline;
His: histidine

A formulation provided herein may have a pH of about 4.0 to about 7.5. In one embodiment, a formulation provided herein may have a pH of about 4.5, about 5.0, about 5.5, about 6.0, about 6.5, or about 7.0. As used herein, the term "about", when referring to pH, refers to a pH ±0.05, 0.1, or 0.2.

One would understand that formulations comprising an antibody or antigen-binding fragment, identified by the methods described herein can be prepared for storage by mixing the protein having the desired degree of purity with optional physiologically acceptable carriers, excipients and/or stabilizers in the form of aqueous solutions (Remington's Pharmaceutical Sciences 16th edition, Osol, A. Ed. (1980)).

Acceptable carriers are physiologically acceptable to the administered patient and retain the therapeutic properties of the compounds with/in which it is administered. Acceptable carriers and their formulations are and generally described in, for example, Remington' pharmaceutical Sciences (18th Edition, ed. A. Gennaro, Mack Publishing Co., Easton, Pa. 1990). One exemplary carrier is physiological saline. The phrase "pharmaceutically acceptable carrier" as used herein means an acceptable material, composition or vehicle, such as a liquid or solid filler, diluent, excipient, and/or solvent involved in carrying or transporting the subject compounds from the administration site of one organ, or portion of the body, to another organ, or portion of the body. Each carrier is acceptable in the sense of being compatible with the other ingredients of the formulation and not injurious to a subject to whom it is administered. Nor should an acceptable carrier alter the specific activity of the subject compounds.

In one aspect, provided herein are pharmaceutically acceptable or physiologically acceptable compositions including solvents (aqueous or non-aqueous), solutions, emulsions, dispersion media, coatings, isotonic and absorption promoting or delaying agents, compatible with administration. Compositions or formulations, therefore, refer to a composition suitable for therapeutic and/or diagnostic use in a subject. Compositions and formulations include an amount of a compound described herein and a pharmaceutically or physiologically acceptable carrier.

Compositions can be formulated to be compatible with a particular route of administration (i.e., systemic or local). Thus, compositions include carriers, diluents, or excipients suitable for administration by various routes.

Compositions can be administered, for example, by injection, including, but not limited to, subcutaneous, intravitreal, intradermal, intravenous, intra-arterial, intraperitoneal, or intramuscular injection. Isotonic agents, for example, sugars, polyalcohols such as manitol, sorbitol, and sodium chloride may be included in the composition. The resulting solutions can be packaged for use as is, or lyophilized; the lyophilized preparation can later be combined with a sterile solution prior to administration. For intravenous, injection, or injection at the site of affliction, the active ingredient can be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as needed. Sterile injectable solutions can be prepared by incorporating an active ingredient in the required amount in an appropriate solvent with one or a combination of ingredients enumerated above, as required, followed by filtered sterilization.

In one embodiment, a formulation described herein does not include surfactants. In another embodiment, a formulation described herein optionally includes a surfactant such as, for example, polysorbate 20 or 80, TWEEN®, PLURONIC® F68, or polyethylene glycol (PEG).

When the compositions are considered for use in medicaments or any of the methods provided herein, it is contemplated that the composition can be substantially free of pyrogens such that the composition will not cause an inflammatory reaction or an unsafe allergic reaction when administered to a human patient. Testing compositions for pyrogens and preparing compositions substantially free of pyrogens are well understood to one or ordinary skill of the art and can be accomplished using commercially available packages.

The phrase "pharmaceutically acceptable" refers to molecular entities and compositions that are physiologically tolerable and do not typically produce an allergic or similar untoward reaction, such as gastric upset, dizziness and the like, when administered to a subject.

The term "unit dose" when used in reference to a therapeutic composition refers to physically distinct units suitable as unitary dosage for subjects, each unit containing a predetermined quantity of active material calculated to produce the desired therapeutic effect in association with the required diluent; i.e., carrier, or vehicle.

The compositions can be administered in a manner compatible with the dosage formulation, and in a therapeutically effective amount. The quantity to be administered depends on the subject to be treated, capacity of the subject's immune system to utilize the active ingredient, and degree of binding capacity desired. Precise amounts of active ingredient required to be administered depend on the judgment of the practitioner and are peculiar to each individual. Suitable regimes for initial administration and booster shots are also variable, but are typified by an initial administration followed by repeated doses at one or more hour intervals by a subsequent injection or other administration. Alternatively, continuous intravenous infusions sufficient to maintain concentrations in the blood are contemplated.

One embodiment contemplates the use of the compositions described herein to make a medicament for treating a condition, disease or disorder described herein. Medicaments can be formulated based on the physical characteristics of the patient/subject needing treatment, and can be formulated in single or multiple formulations based on the stage of the condition, disease or disorder. Medicaments can be packaged in a suitable package with appropriate labels for the distribution to hospitals and clinics wherein the label is for the indication of treating a subject having a disease described herein. Medicaments can be packaged as a single or multiple units. Instructions for the dosage and administration of the compositions can be included with the packages as described below.

Also provided herein is a pre-filled syringe suitable for intravenous or intravitreal administration, comprising a formulation described herein. Such pre-filled syringes may be packaged and labeled for use for treatment of an angiogenesis-related condition such as any of the conditions described herein. Packages may further include directions for storage and administration. Provided herein is a package containing one or more pre-filled syringes suitable for intravenous or intravitreal administration comprising the formulation of any of the preceding claims. Also provided herein is the preparation of a medicament containing a formulation described herein for treatment of an angiogenesis-related condition such as any of the conditions described herein.

Methods of Treatment

Provided herein is a method of treating a subject (human or non-human) by administering to the subject a formulation of an antibody that preferentially binds to CD105. Provided herein are methods of preventing or treating one or more diseases or disorders associated with angiogenesis/neovascularization, excessive vascularization, tumor growth, tumor cell proliferation or small vessel dilation comprising administering a composition containing an anti-CD105 antibody, or antigen-binding fragment thereof, thereby preventing, treating, ameliorating, or lessening the disease or its severity.

An effective response of the present invention is achieved when the subject experiences stasis, or partial or total alleviation or reduction of signs or symptoms of illness, and specifically includes, without limitation, prolongation of survival. The expected progression-free survival times may be measured in months to years, depending on prognostic factors including the number of relapses, stage of disease, and other factors. Prolonging survival includes without limitation times of at least 1 month (mo), about at least 2 mos., about at least 3 mos., about at least 4 mos., about at least 6 mos., about at least 1 year (yr), about at least 2 years, about at least 3 years, about at least 4 years, about at least 5 years, etc., or any interval therein. Overall or progression-free survival can be also measured in months to years. Alternatively, an effective response may be that a subject's signs or symptoms or cancer burden remain static and do not worsen. Further indications of treatment of indications are described in more detail below.

Compositions of antibodies described herein can be used as non-therapeutic agents (e.g., as affinity purification agents). Generally, in one such embodiment, a protein of interest is immobilized on a solid phase such a Sephadex® resin or filter paper, using conventional methods known in the art. The immobilized protein is contacted with a sample containing the target of interest (or fragment thereof) to be purified, and thereafter the support is washed with a suitable solvent that will remove substantially all the material in the sample except the target protein, which is bound to the immobilized antibody. Finally, the support is washed with another suitable solvent, such as glycine buffer, pH 5.0, which will release the target protein. In addition to purification, compositions can be used for detection, diagnosis and therapy of diseases and disorders associated with CD105.

"Contacting" is defined herein as a means of bringing a formulation as provided herein in physical proximity with a cell, organ, tissue or fluid as described herein. Contacting encompasses systemic or local administration of any of the formulations provided herein and includes, without limitation, in vitro, in vivo and/or ex vivo procedures and methods. "Combining" and "contacting" are used interchangeably herein and are meant to be defined in the same way. For in vivo applications, contacting can occur, for example, via administration of a composition to a patient by any suitable means; compositions with pharmaceutically acceptable excipients and carriers have been described in more detail above.

As used herein, "prevention" refers to prophylaxis, prevention of onset of signs or symptoms, prevention of progression of a disease or disorder associated with angiogenesis or correlated with CD105 activity. In one non-limiting embodiment diagnosed with stage 1 cancer may be administered a formulation described herein, thereby preventing progression of the cancer to stage 2. In yet another embodiment, a patient that is asymptomatic, but tests positive for one or cancer biomarkers, may be administered a formulation described herein, thereby preventing progression of the cancer. As used herein, "inhibition," "treatment" and "treating" are used interchangeably and refer to, for example, stasis of signs or symptoms, prolongation of survival, partial or full amelioration of signs or symptoms, and partial or full eradication of a tumor or metastases.

A "subject" or "patient" (e.g., a mammal such as a human or a non-human animal such as a primate, rodent, cow, horse, pig, sheep, camel, llama, etc.) can be a mammal who exhibits one or more clinical manifestations and/or signs or symptoms of a disease or disorder described herein. In certain situations, a subject may be asymptomatic and yet still have clinical manifestations of the disease or disorder. An antibody can be conjugated to a therapeutic moiety or be a fusion protein containing a therapeutic moiety. An antibody can be conjugated to a detectable moiety or be a fusion protein containing a detectable moiety. In one embodiment, the antibody can be conjugated to both a therapeutic moiety and a detectable moiety. An antibody can be conjugated to, or recombinantly engineered with, an affinity tag (e.g., a purification tag). Affinity tags are conventional in the art.

Antibodies or thereof provided herein are such that they can be conjugated or linked to a therapeutic moiety or an imaging or a detectable moiety and/or an affinity tag. Methods for conjugating or linking polypeptides are well known in the art. Associations (binding) between compounds and labels include any means known in the art including, but not limited to, covalent and non-covalent interactions, chemical conjugation as well as recombinant techniques.

"Angiogenesis" is used herein to include all aspects of blood vessel maintenance and development. Thus, angiogenesis includes the formation of new capillary blood vessels (whether de novo or from preexisting vessels) leading to neovascularization as well as the maintenance and control of the existing vasculature and small blood vessels. Angiogenesis is a complex process which includes a series of sequential steps including endothelial cell-mediated degradation of vascular basement membrane and interstitial matrices, migration of endothelial cells, proliferation of endothelial cells, and formation of capillary loops by endothelial cells. Angiogenesis is inclusive of the growth and/or development of new blood vessels (also referred to as neovascularization), dilation of the small vessels, excessive or prolonged vascular growth, and maintenance of the existing vasculature.

The term "angiogenesis-associated disease" is used herein to mean certain pathological processes in humans where angiogenesis is abnormally prolonged. This further includes angiogenesis conditions and diseases, such as those diseases and conditions related to, caused by, or associated with angiogenesis. Non-limiting examples of such diseases include various forms of cancers and metastases, macular degeneration and CNV. The antibodies described herein can be used to treat an angiogenesis-associated disease by binding CD105 and inhibiting angiogenesis.

The term "anti-angiogenic therapy" is used herein to mean therapy targeted to cells and/or vasculature expressing CD105 (expressed at higher levels on proliferating vasculature as compared to quiescent vasculature); this further includes therapy that is directed against angiogenesis (i.e., the formation of new capillary blood vessels leading to neovascularization), therapy that is directed against existing vasculature and/or excessive vascularization or blood vessel growth, therapy directed towards the dilation of small vessels, and therapy directed to a disease or condition (e.g., vascular targeting therapy). Exemplary diseases or conditions contemplated within the invention include, but are not limited to, various forms of cancer and metastases.

Provided herein is a method of treating an angiogenesis-related disease in a patient (subject) in need thereof, comprising administering to said patient a formulation described herein. Such formulations may be administered to the patient intravitreally or intravenously.

An angiogenesis-related disease described herein may be, for example, a cancer or a metastasis. In one embodiment, the cancer is a solid tumor. Cancers to be treated include, for example, an epithelial based tumor. Non-limiting examples of cancers to be treated with such formulations include, but are not limited to, a lung cancer, a gynecologic malignancy, a melanoma, a breast cancer, a pancreatic cancer, an ovarian cancer, a uterine cancer, a colorectal cancer, a prostate cancer, a kidney cancer, a head cancer, a pancreatic cancer, a liver cancer (hepatocellular cancer), a uterine cancer, a neck cancer, a kidney cancer (renal cell cancer), a sarcoma, a myeloma, and a lymphoma. Formulations for treatment of a cancer or a metastasis may be administered to the patient intravenously.

Alternatively, an angiogenesis-related disease described herein may be, for example, is an ophthalmologic condition. Ophthalmologic conditions include, but are not limited to, age-related macular degeneration, diabetic retinopathy, macular edema and/or choroidal neovascularization. Age related macular degeneration (AMD) may be wet AMD or dry AMD. Formulations for treatment of an ophthalmologic condition may be administered to the patient intravitreally.

In such methods, the formulation may be administered to a patient one or more times. For example, the formulation may be administered once per day, once per week, once per month, once bi-monthly, once every two months, once every three months, once every four months, once every 5 months, or once every 6 months. Treatment schedules may be increased or decreased as needed depending upon the response of the patient to the treatment.

In one aspect, a formulation is administered until one or more signs or symptoms of the angiogenesis-related disease are reduced.

With respect to ophthalmologic conditions, the one or more signs or symptoms may include, but not be limited to, shrinking blood vessels, inhibiting endothelial cell proliferation associated with ocular disease, clearing of signs or symptoms of bleeding, treating cloudy vision, providing stasis of vision loss, improving vision, and/or preventing leakage of blood vessels.

With respect to cancers or metastases, treatment may result in improvement of the patient's condition and treatment can be assessed by determining if one or more of the following factors has occurred: decreased cell proliferation, decreased numbers of cells, increased apoptosis, or decreased survival of at least a portion of the cells comprising the cell proliferative disorder.

Treatment may result in partial or total elimination of a tumor or metastases and/or prolongation of survival of the patient.

In one embodiment, one or more signs or symptoms are reduced in severity or duration by about 2%, about 5%, about 10%, about 15%, about 20%, about 25%, about 30%, about 35%, about 40%, about 45%, about 50%, about 55%, about 60%, about 65%, about 70%, about 75%, about 80%, about 90%, about 95%, or about 100% following administration of one or more doses of the formulation to the patient.

In another embodiment, one or more signs or symptoms are reduced in severity or duration by about 2-fold, about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 90-fold, about 95-fold, about 100-fold, or more, following administration of one or more doses of the formulation to the patient.

Provided herein is a method of treating an ophthalmologic condition in a patient in need thereof, comprising administering to said patient a formulation described herein, whereby one or more signs or symptoms of said ophthalmologic condition are ameliorated by the treatment. Administration of the formulation may be intravitreal administration.

Also provided herein is a method of preventing or treating a cancer or metastasis in a subject in need thereof, comprising administering to said patient a formulation described herein, whereby one or more signs or symptoms of said cancer or metastasis are ameliorated. Administration of the formulation may be intravenous administration.

The terms "recurrence," "relapse" or "relapsed" refer to the return of a cancer or disease after clinical assessment of the disappearance of disease. A diagnosis of distant metastasis or local recurrence can be considered a relapse.

The term "maintenance therapy" refers to scheduled retreatment that is given to help maintain a previous treatment's effects. Maintenance therapy is often given to help keep cancer in remission or prolong a response to a specific therapy regardless of disease progression.

The term "progression-free survival" in oncology refers to the length of time during and after treatment that a cancer does not progress. Progression-free survival includes the amount of time patients have experienced a complete response or a partial response, as well as the amount of time patients have experienced stable disease.

In one aspect, provided herein is a method of preventing or treating a cancer or a metastasis in a subject by administering any of the compositions provided herein to a patient suffering from cancer or metastasis. Such a patient can be symptomatic or asymptomatic.

In some cases, administration of the composition prolongs life of the patient being treated, reduces tumor volume, eliminates a tumor, decreases cell proliferation, increases apoptosis of tumor cells, or a combination thereof.

If needed, the methods can further include surgical removal of the cancer and/or administration of an additional anti-cancer agent or treatment. Anti-cancer agents have been provided elsewhere herein.

In one aspect, signs or symptoms of the patient suffering from cancer are ameliorated. Amelioration can be manifested as, for example, reduction in pain, reduced tumor size, elimination of tumors, prevention of increases in tumor size or progression or of disease, prevention of formation of metastasis, or inhibition of metastatic growth, or a combination thereof.

In one aspect, administration of a formulation described herein reduces or eliminates the need for the patient to undergo surgery or treatment with one or more additional anti-cancer agents or treatments.

Compositions containing an anti-CD105 antibody can be administered sequentially or simultaneously with a composition containing an anti-VEGF antibody (or antigen-binding fragment thereof). Such administrations include, but are not limited to, administration within about 12 weeks of each other, within about 8 weeks of each other, within about 4 weeks of each other, within about 3 weeks of each other, within about 2 weeks of each other, within about a week of each other, within a day of each other, within about 12 hours of each other, within about 6 hours of each other, within about 3 hours of each other, within about 1 hour of each other, within about 30 minutes of each other, on the same day, at the same time, or a combination thereof. When multiple doses of the composition of the present invention and/or the combined therapeutic moiety are contemplated, it is understood that doses of each can be empirically determined using known doses and concentrations based on the age, height, weight, health and other physical characteristics of a subject using standards of commercially available products.

Formulations can be administered to a patient in a therapeutically effective amount that are effective for producing some desired therapeutic effect by inhibiting a disease or disorder at a reasonable benefit/risk ratio applicable to any medical treatment. For the administration of the present formulations to human patients, the formulations can be formulated by methodology known by one in the art. A therapeutically effective amount is an amount achieves at least partially a desired therapeutic or prophylactic effect in an organ or tissue. The amount of an anti-CD105 antibody or an anti-VEGF antibody necessary to bring about prevention and/or therapeutic treatment of a disease or disorder is not fixed per se. The amount of antibody administered may vary with the type of disease, extensiveness of the disease, and size of the mammal suffering from the disease or disorder. In one embodiment, two antibodies described herein are administered to a patient in combination as described above. Administration in combination can refer to administration in a single formulation or in separate formulations.

"Administering" is referred to herein as providing one or more formulations to a patient in a manner that results in the formulation being inside the patient's body. Such an administration can be by any route including, without limitation, locally, regionally or systemically by subcutaneous, intravitreal, intradermal, intravenous, intra-arterial, intraperitoneal, or intramuscular administration (e.g., injection).

Actual dosage levels of the active ingredients in the formulations can be varied so as to obtain an amount of the active ingredient that is effective to achieve the desired therapeutic response for a particular patient, formulation, and mode of administration, without being toxic to the patient. The selected dosage level will depend upon a variety of factors including the activity of the particular compound employed, the route of administration, the time of administration, the rate of excretion of the particular compound being employed, the duration of the treatment, other drugs, compounds and/or materials used in combination with the particular formulation employed, the age, sex, weight, condition, general health and prior medical history of the patient being treated, and like factors well known in the medical arts.

Additionally, the dose(s) of an antibody can be administered twice a week, weekly, every 2 weeks, every 3 weeks, every 4 weeks, every 6 weeks, every 8 weeks, every 12 weeks, every 24 weeks or any combination of weeks therein. Dosing cycles are also contemplated such as, for example, administering antibodies once or twice a week for 2, 3, 4, 5 or 6 weeks, followed by 1, 2, 3, 4, 5, or 6 weeks without therapy. Alternatively, depending upon the response of a subject to therapy, cycling time between treatments can be 1, 2, 3, 4, 5, 6, 7, 8, 9, 10, 11 or 12 months. Additional dosing cycles including, for example, different combinations of the doses and weekly cycles described herein are also contemplated within the invention.

A physician or veterinarian can readily determine and prescribe the effective amount (ED50) of the formulation required. For example, the physician or veterinarian could start doses of the compounds employed in the formulation at levels lower than that required in order to achieve the desired therapeutic effect and gradually increase the dosage until the desired effect is achieved. Alternatively, a dose can remain constant.

Formulations can be administered to a patient by any convenient route such as described above. Regardless of the route of administration selected, the compounds of the present invention, which can be used in a suitable hydrated form, and/or the formulations, are formulated into acceptable dosage forms such as described below or by other conventional methods known to those in the art.

Data obtained from cell culture assays and/or animal studies can be used in formulating a range of dosage for use in humans. The dosage may vary within this range depending upon the dosage form employed and the route of administration utilized. For any compound, a therapeutically effective dose can be estimated initially from cell culture assays. A dose can be formulated in animal models to achieve a circulating plasma concentration arrange that includes the $IC_{50}$ (i.e., the concentration of the test compound which achieves a half-maximal inhibition) as determined in cell culture. Levels in plasma can be measured, for example, by high performance liquid chromatography. Such information can be used to more accurately determine useful doses in humans. Formulations containing combinations of compounds can also be assessed using any of these methods.

In one embodiment, the invention contemplates inhibition of angiogenesis in a tissue. The extent of angiogenesis in a tissue and, therefore, the extent of inhibition achieved can be evaluated by a variety of methods, such as are described herein.

The unique specificity of the antibodies which recognize (e.g., preferentially bind) CD105 or VEGF and inhibits angiogenesis, provides diagnostic and therapeutic uses for diseases characterized by angiogenesis (neovascularization), small vessel dilation, excessive vascularization, tumor cell proliferation, and/or tumor growth. Antibodies can be administered to a subject suffering from various forms of cancer (primary tumors and metastases).

One would understand that, in addition to administration of the formulations described herein, it is contemplated herein that a subject can also be treated with one or more additional angiogenesis inhibitors.

The term "angiogenesis inhibitor" is used herein, for purposes of the specification and claims, to mean a compound or molecule including, but not limited to, peptides, proteins, enzymes, polysaccharides, oligonucleotides, DNA, RNA, recombinant vectors, and drugs which function to inhibit angiogenesis. Angiogenesis inhibitors are known in the art and all types are contemplated herein. Non-limiting examples of compounds and molecules include natural and synthetic biomolecules such as paclitaxel, O-(chloroacetyl-carbomyl) fumagillol ("TNP-470" or "AGM 1470"), thrombospondin-1, thrombospondin-2, angiostatin, human chondrocyte-derived inhibitor of angiogenesis ("hCHIAMP"), cartilage-derived angiogenic inhibitor, platelet factor-4, gro-beta, human interferon-inducible protein 10 ("IP 10"), interleukin 12, Ro 318220, tricyclodecan-9-yl xanthate ("D609"), irsogladine, 8,9-dihydroxy-7-methyl-benzo[b] quinolizinium bromide ("GPA 1734"), medroxyprogesterone, a combination of heparin and cortisone, glucosidase inhibitors, genistein, thalidomide, diamino-antraquinone, herbimycin, ursolic acid, and oleanolic acid. Non-limiting examples of antibodies include those directed towards molecules such as VEGF, VEGF receptor, or different epitopes of CD105. Additionally, small molecular inhibitors of VEGF receptor are known and contemplated herein. Non-limiting examples of VEGF receptor inhibitors include ranibizumab, aflibercept, sunitinib, sorafenib, axitinib, pegaptanib and pazopanib.

Multiple combinations of these VEGF receptor inhibitors can be administered with the formulations described herein. In one embodiment, combinations may result in the use of lower doses for the described antibodies or antigen binding. Such alterations in dosing may result from synergistic effects of the combinations of the antibodies.

Cancer

CD105 is associated with tumor angiogenesis and is strongly up-regulated in the endothelium of various tumor tissues compared with that in normal tissues. CD105 is up-regulated in a wide range of tumor endothelia. Additionally, there is stronger expression of CD105 in tumor endothelium than corresponding normal tissues. Thus, the inhibition of angiogenesis with anti-CD105 antibodies represents a treatment option for cancerous tumors. The formulations described herein can be used to treat cancerous tumors and metastases. The formulations can also be used in the formulations of medicaments for the treatment cancerous tumors and metastases.

VEGF represents one target for antitumor therapies because its expression is upregulated in a range of solid tumors. VEGF is a major regulator of angiogenesis, the growth of new vessels from pre-existing vessels. This process is fundamental to the growth of solid tumors, which rely on the formation of new blood vessels. Certain small molecule therapeutic agents are able to target vascular endothelial growth factor receptor ("VEGFR"); such targeting by small molecule therapeutics can result in anti-cancer effects. VEGF receptor-targeted agents indirectly block tumor growth, through the inhibition of new vessel formation. Inhibiting VEGF-induced angiogenesis can exert an anti-tumor or improved anti-tumor effect without significantly inhibiting VEGF stimulation of macrophages, osteoclasts or chondroclasts.

The term "tumor" is used herein to refer to a cancerous tissue expressing CD105 and/or VEGF (as compared to expression by normal tissue of the same type). Tumors can include solid tumors and semi-solid tumors. Non-limiting examples of tumors include human leukemias, including non-T-cell-type (non-T) acute lymphoblastic leukemia (ALL), myelo-monocytic leukemia; and human solid and semi-solid tumors, with its surrounding vasculature expressing CD105 at moderate to high levels (as compared to expression by normal tissue of the same type) including angiosarcoma, breast carcinoma, stomach cancer, colon carcinoma, Hodgkin's lymphoma, lymphoma, glioblastoma multiforme (GBM), lung carcinoma, melanoma, myeloma, lymphoma, osteosarcoma, ovarian carcinoma, parotid tumor, pharyngeal carcinoma, prostate carcinoma, hepatocellular carcinoma, renal carcinoma, and rectosigmoid carcinoma.

A cancerous tissue to be treated is, for example, an endothelial tissue expressing an abnormal level of CD105 and/or VEGF.

In the absence of neovascularization of tumor tissue, the tumor tissue does not obtain the required nutrients, slows in growth, ceases additional growth, regresses and ultimately becomes necrotic resulting in killing of the tumor. Provided herein are methods of inhibiting tumor neovascularization by inhibiting tumor angiogenesis. Similarly, provided herein are methods of inhibiting tumor growth.

The methods are also particularly effective against the formation of metastases because their formation requires vascularization of a primary tumor so that the metastatic cancer cells can exit the primary tumor and their establishment in a secondary site requires neovascularization to support growth of the metastases.

It will be appreciated that a "subject suffering from a cancer/metastasis" of the invention may express a mutant protein (tumor associated antigen) or a mutant gene and not yet be symptomatic for the disease. In one non-limiting example of colon cancer (which is associated with the mutant K-ras protein), a subject with a mutant K-ras protein in some cells of the colon is a subject to be treated even though that subject may not yet be symptomatic for colon cancer. "Signs or symptoms of illness" represent clinically recognized manifestations or indications of disease.

By "treating" a subject suffering from tumor or metastasis, it is meant that the subject's signs or symptoms are partially alleviated, totally alleviated, or remain static following treatment. A patient that has been treated can exhibit a partial or total alleviation of tumor load. This is intended to encompass prophylaxis, therapy and cure. In one non-limiting example, a subject suffering from a highly metastatic cancer (e.g., breast cancer) is treated where additional metastasis either do not occur, or are reduced in number as compared to a subject who does not receive treatment. In another non-limiting example, a subject is treated where the subject's solid cancer either becomes reduced in size or does not increase in size as compared to a subject who does not receive treatment. In yet another non-limiting example, the number of cancer cells in a treated subject either does not increase or is reduced as compared to the number of cancer cells in a subject who does not receive treatment. Improvement can also be defined, for example, as decreased cell proliferation, decreased numbers of cells, increased apoptosis, and/or increased survival of the subject being treated.

Treatment may result in partial or total elimination of a tumor or metastases and/or prolongation of survival of the patient.

In one embodiment, one or more signs or symptoms are reduced in severity or duration by about 2%, about 5%, about 10%, about 15%, about 20%, about 25%, about 30%, about 35%, about 40%, about 45%, about 50%, about 55%, about 60%, about 65%, about 70%, about 75%, about 80%, about 90%, about 95%, or about 100% following administration of one or more doses of the formulation to the patient.

In another embodiment, one or more signs or symptoms are reduced in severity or duration by about 2-fold, about 5-fold, about 10-fold, about 15-fold, about 20-fold, about 25-fold, about 30-fold, about 35-fold, about 40-fold, about 45-fold, about 50-fold, about 55-fold, about 60-fold, about 65-fold, about 70-fold, about 75-fold, about 80-fold, about 90-fold, about 95-fold, about 100-fold, or more, following administration of one or more doses of the formulation to the patient.

A tumor or cancer to be treated in the methods described herein includes, but is not limited to, a lung cancer, a gynecologic malignancy, a melanoma, a breast cancer, a brain cancer (e.g., glioblastoma multiforme, "GBM" or a glioma) a pancreatic cancer, an ovarian cancer, a uterine cancer, a colorectal cancer, a prostate cancer, a kidney cancer, a head cancer, a liver cancer (hepatocellular cancer), a neck cancer, a kidney cancer (renal cell cancer), an penile cancer, a stomach cancer, a thyroid cancer, a bladder cancer, a sarcoma, a carcinoma, a myeloma, and lymphoma. In one embodiment, a tumor to be treated is a solid or semi-solid tumor. In another embodiment, a tumor to be treated is a primary tumor. In another embodiment, a tumor to be treated is a metastatic tumor. In one embodiment, a tumor or cancer to be treated is of epithelial origin. In another embodiment, the cancer to be treated is myeloma. In another embodiment, the cancer to be treated is ovarian cancer. In another embodiment, the cancer to be treated is kidney/renal cancer. In yet another embodiment, the cancer to be treated is hepatocellular/liver cancer.

Compounds can be, as needed, administered in combination with one or more additional therapeutic treatments including, but not limited to, adriamycin, cyclophosphamide, paclitaxel, pemetrexed, temozolomide, oxaliplatin, cetuximab, panitumumab, sorafenib, sunitinib, gefitinib, erlotinib, 5-fluorouracil, irinotecan, topotecan, leucovorin, bortezumib, lenalidomide, thalidomide, capecitabine, docetaxel and many other conventional cancer therapies described herein. As used herein, "radiation" refers to, for example, microwaves, ultraviolet (UV), infrared (IR), or alpha-, beta- or gamma-radiation. Radiation can be "focused" or locally delivered using conventional techniques to target radiation to the site of one or more tumors without radiating the entire body. One would understand that the listing of therapeutic regimens listed below represents conventional therapies, but the present invention encompasses other known therapeutic regimens which are not specifically disclosed herein.

In one embodiment, the cancer is ovarian cancer and the one or more additional therapeutic treatments is surgery, chemotherapy (e.g., doxorubicin, doxorubicin HCl liposome, gemcitabine, and platinum-based chemotherapeutics such as cisplatin, carboplatin and oxaliplatin), melphalan, topoisomerase I inhibitors such as topotecan and irinotecan, taxane-based therapy, hormones, radiation therapy, whole body hypothermia, isoflavone derivatives, cytotoxic macrolides such as epothilones, angiogenesis inhibitors such as bevacizumab, signal transduction inhibitors such as trastuzumab, gene therapy, RNAi therapy, immunotherapy, monoclonal antibodies, phosphatidylinositol-like kinase inhibitors such as rapamycin, or any combination thereof. The combination therapy of the antibodies described herein with the ovarian cancer therapies may also provide for lower doses of either therapy, or both, due to a synergistic effect from the co-administration of the therapies.

In one embodiment, the cancer is renal/kidney cancer and the one or more additional therapeutic treatments is surgery, chemotherapy, pazopanib, interferon-alpha or IL-2. In yet another embodiment, the additional agent is a VEGF receptor inhibitor. Non-limiting examples of VEGF receptor inhibitors include those described above, aflibercept, sunitinib, sorafenib, axitinib, and pazopanib. The combination therapy of the antibodies described herein with the kidney cancer therapies may also provide for lower doses of either therapy, or both, due to a synergistic effect from the co-administration of the therapies.

In one embodiment, the cancer is myeloma and the one or more additional therapeutic treatments is surgery, radiotherapy, bortezomib, lenalidomide, or thalidomide. The dosages for any of these therapies are known in the art and can be adjusted with combination therapy accordingly.

In one embodiment, the cancer is prostate cancer and the one or more additional therapeutic treatments is surgery, radiotherapy (e.g., external beam or brachytherapy), hormonal deprivation (androgen suppression including with abiraterone), heat shock protein 90 (HSP90) inhibitors, chemotherapy (e.g., docetaxel, estramustine, platinum-based chemotherapy such as cisplatin, carboplatin, satraplatin and oxaliplatin), prednisone or prednisolone, cholesterol-lowering drugs such as statins, leutinizing hormone-releasing hormone (LHRH) agonists, RNAi therapy, dendritic cell-based therapies, whole tumor cells genetically modified to secrete granulocyte macrophage—colony stimulating factor (GM-CSF) (also known as GVAX), or any combination thereof. In yet another embodiment, the additional agent is a VEGF receptor inhibitor. Non-limiting examples of VEGF receptor inhibitors include aflibercept sunitinib, sorafenib, axitinib, and pazopanib.

In one embodiment, the cancer is lung cancer and the one or more additional therapeutic treatments is surgery, radiotherapy (e.g., thoracic radiotherapy, radiation therapy with charged particles, Uracil-tegafur and Platinum-based chemotherapy (e.g., cisplatin, carboplatin, oxaliplatin, etc.) and vinorebline, erlotinib, gefitinib, anti-epidermal growth factor receptor antibodies (e.g., cetuximab), small molecule inhibitors of tyrosine kinases, direct inhibitors of proteins involved in lung cancer cell proliferation, Aurora kinase inhibitors, laser-induced thermotherapy, RNAi therapy, whole tumor cells genetically modified to secrete granulocyte macrophage—colony stimulating factor (GM-CSF) (also known as GVAX), or any combination thereof. Additional therapeutic treatments include paclitaxel or pemetrexed. In yet another embodiment, the additional agent is a VEGF receptor inhibitor. Non-limiting examples of VEGF receptor inhibitors include aflibercept, sunitinib, sorafenib, axitinib, and pazopanib. The dosages for any of these therapies are known in the art and can be adjusted with combination therapy accordingly.

In one embodiment, the cancer is breast cancer and the one or more additional therapeutic treatments is surgery, monoclonal antibodies (e.g., Her-2 antibodies, herceptin), adjuvant chemotherapy such as single agent chemotherapy or combination chemotherapy (e.g., anthracycline- and taxane-based polychemotherapies), or target-specific trastuzumab with or without endocrine manipulation with or without PMRT, vinorelbine), adriamycin, cyclophosphamide, capecitabine, docetaxel, selective estrogen receptor modulators such as tamoxifen and raloxifene, allosteric estrogen receptor modulators such as trilostane, radiation (e.g., interstitial brachytherapy, Mammosite device, 3-dimensional conformal external radiation and intraoperative radiotherapy), Aromatase inhibitors that suppress total body synthesis (e.g., anastrozole, exemestane and letrozole), RNAi therapy, intravenous analogs of rapamycin that are immunosuppressive and anti-proliferative such as temsirolimus, or any combination thereof. A review of methods for conducting three-dimensional in vitro tissue culture models of breast cancer are described by Kim et al., Breast Cancer Research Treatment 85(3): 281-91 (2004). Other in vivo and in vitro models for testing cancers are known and can be used to test antibodies described herein. In yet another embodiment, the additional agent is a VEGF receptor inhibitor. Non-limiting examples of VEGF receptor inhibitors include aflibercept, sunitinib, sorafenib, axitinib, and pazopanib. The dosages for any of these therapies are known in the art and can be adjusted with combination therapy accordingly.

In one embodiment, the cancer is colon cancer and the one or more additional therapeutic treatments is surgery, radiation therapy, and chemotherapy (e.g., 5-fluorouracil, levamisole, leucovorin or semustine (methyl CCNU)), N-[2-(dimethylamino)ethyl]acridine-4-carboxamide and other related carboxamide anticancer drugs; non-topoisomerase II inhibitors, irinotecan, liposomal topotecan, taxane class of anticancer agents (e.g., paclitaxel or docetaxel), a compound of the xanthenone acetic acid class (e.g., 5,6-dimethylanthenone-4-acetic acid PMAA), laminarin, site-selective cyclic AMP Analogs (e.g., 8-chloroadenosine 3',5'-cyclic phosphate), pyranoindole inhibitors of Cox-2, carbazole inhibitors of Cox-2, tetrahydrocarbazole inhibitors of Cox-2, indene inhibitors of Cox-2, localized inhibitors of NSAIDS (e.g., anthranilic acids, aspirin (5-acetylsalicylic acid), azodisal sodium, carboheterocyclic acids, carprofen, chlorambucil, diclophenac, fenbufen, fenclofenac, fenoprofen, flufenamic acid, flurbiprofen, fluprofen, furosemide, gold sodium thiomalate, ibuprofen, indomethacin, indoprofen, ketoprofen, lonazolac, loxoprofen, meclofenamic acid, mefanamic acid, melphalan, naproxen, penicillamine, phenylacetic acids, proprionic acids, salicylic acids, salazosulfapyridine, sulindac, tolmetin, a pyrazolone butazone propazone, NSAID, meloxicam, oxicams, piroxicam, feldene, piroxicam beta cyclodextran, tenoxicam. etodolac, and oxaprozin), an inhibitor of HER-2/ncu, RNAi therapy, GM-CSF, monoclonal antibodies (e.g., anti-Her-2/neu antibodies, anti-CEA antibodies, A33 (FIB 8779), 100-210 (HB 11764) and 100-310 (HB 11028)), cetuximab, panitumumab, hormonal therapy, pyrimidineamines, camptothecin derivatives (e.g., CPT-11), folinic acid (FA), gemcitabine, Ara-C, platinum-based chemotherapeutics such as cisplatin, carboplatin and oxaliplatin, a cGMP-specific phosphodiesterase inhibitor, or any combination thereof. In one embodiment the additional therapeutic treatment is a combination of 5-fluorouracil, leucovorin and oxaliplatin (FOLFOX). In one embodiment, the additional therapeutic treatment is a combination of 5-fluorouracil, irinotecan and leucovorin (IFL). In one embodiment, the additional agent is cetuximab. In one embodiment, the additional agent is panitumumab. In yet another embodiment, the additional agent is a VEGF receptor inhibitor. Non-limiting examples of VEGF receptor inhibitors include aflibercept, sunitinib, sorafenib, axitinib, and pazopanib. The dosages for any of these therapies are known in the art and can be adjusted with combination therapy accordingly.

In one embodiment, the cancer is pancreatic cancer and the one or more additional therapeutic treatment is a combination of therapeutic treatments is surgery, radiation therapy, 5-fluorouracil and radiation therapy, systemic therapy, stenting, gemcitabine, gemcitabine and radiation therapy, cetuximab, erlotinib, chemoradiation, or any combination thereof. In yet another embodiment, the additional agent is a VEGF receptor inhibitor. Non-limiting examples of VEGF receptor inhibitors include afliberceipt, sunitinib, sorafenib, axitinib, and pazopanib.

Patients can be assessed with respect to signs or symptoms at one or more multiple time points including prior to, during, and after treatment regimens. Treatment can result in improving the subject's condition and can be assessed by determining if one or more of the following factors has occurred: decreased tumor size, decreased cell proliferation, decreased numbers of cells, decreased neovascularization, increased apoptosis, or decreased survival of at least a portion of the cells comprising the cell proliferative disorder. One or more of these occurrences may, in some cases, result in partial or total elimination of the cancer and/or prolongation of survival of the patient. Alternatively, for terminal stage cancers, treatment may result in stasis of disease, better quality of life and/or prolongation of survival.

When compositions are administered sequentially, a composition comprising an anti-CD105 antibody described herein can be, for example, administered prior to and/or after an anti-VEGF antibody (or antigen-binding fragment thereof).

When compositions are administered simultaneously, a composition containing an anti-CD105 antibody can be administered at the same site, or at a different site than a composition containing an anti-VEGF antibody.

In yet another embodiment, provided herein are compositions (medicaments) containing an anti-CD105 antibody and an anti-VEGF antibody (or antigen-binding fragment thereof), capable of inhibiting one or more of the biological activities of CD105 and VEGF, respectively, such as mitogenic activity, cell proliferation, tumor growth, neovascularization, or angiogenic activity.

One would understand that treatment regimens may include one or more administrations of each of the compositions described herein. A composition can be administered in a single dose or multiple doses. Administration of separate compositions may be by the same route or by different routes.

In one embodiment, a composition is administered every 1 to 3 weeks for 6 to 12 cycles or until tumor progression. The method can further include the step of administering a composition each of 1 to 12 weeks for up to 2 years. In another non-limiting example, the concurrent administration of an anti-CD105 antibody and an anti-VEGF antibody (or antigen-binding fragment thereof) occurs at week 1, followed by additional administration of the compositions at week 1, 2, 3 or 4, wherein the concurrent administration is repeated for 6 to 12 cycles or until tumor progression and followed by administration of the compositions each 1 to 12 weeks for up to 2 years.

In one non-limiting example of a method for treating cancer in a patient, the method includes surgical removal of the cancer and administration of an anti-CD105 antibody and an anti-VEGF antibody (or antigen-binding fragment thereof) at 1 to 3 weeks for 12 months or until tumor progression followed by concurrent administration of an anti-CD105 antibody and an anti-VEGF antibody (or antigen-binding fragment thereof) in a dose at 1 to 12 weeks. Additionally, the concurrent administration of an anti-CD105 antibody and an anti-VEGF antibody (or antigen-binding fragment thereof) can be repeated every 1 to 3 weeks for up to 6 cycles. Optionally, the method further includes administering an anti-CD105 antibody and an anti-VEGF antibody (or antigen-binding fragment thereof) each of one to twelve weeks for up to two years. It will be understood that treatment regimens can be combined with monitoring methods provided herein to determine if and when additional doses of an anti-CD105 antibody and an anti-VEGF antibody (or antigen-binding fragment thereof) need be administered.

Combination therapy may provide a synergistic and/or beneficial effect or may allow lower doses of a combination to provide a greater margin of safety. The invention encompasses treatment protocols that enhance the prophylactic or therapeutic effect of an anti-CD105 antibody and an anti-VEGF (or antigen-binding fragment thereof) for preventing, managing, treating or ablation of cancer or other diseases.

In one embodiment, an additional therapeutic treatment such as, for example, an angiogenesis inhibitor (as described herein) is administered to a subject. The composition containing such an additional therapeutic treatment can be administered in combination (either sequentially or simultaneously) with the other compositions described herein.

In one non-limiting method for treating cancer provided herein, an additional therapeutic treatment includes surgical removal of the cancer, irradiation, one or more chemotherapeutic agents, or a combination thereof, and concurrent administration of one or more compositions described herein. In one aspect, administration of a composition can be, for example, a 20 minute intravenous infusion.

Ocular Conditions Involving Angiogenesis

In one aspect, the present invention provides a method for treating diabetic retinopathy, macular degeneration, choroidal neovascularization, macular edema or neovascular glaucoma in a patient by administering to the patient a therapeutically effective amount one or more of the formulations provided herein.

Macular degeneration (AMD) is the loss of photoreceptors in the portion of the central retina, termed the macula, responsible for high-acuity vision. Degeneration of the macula is associated with abnormal deposition of extracellular matrix components and other debris in the membrane between the retinal pigment epithelium and the vascular choroid. This debris-like material is termed drusen. Drusen is observed with a funduscopic eye examination. Normal eyes may have maculas free of drusen, yet drusen may be abundant in the retinal periphery. The presence of soft drusen in the macula, in the absence of any loss of macular vision, is considered an early stage of AMD. Macular degeneration is characterized by choroidal neovascularization (CNV), the development of abnormal blood vessels beneath the retinal pigment epithelium (RPE) layer of the retina. These vessels break through the Bruch's membrane, disrupting the retinal pigmented epithelium, bleed, and eventually cause macular scarring which results in profound loss of central vision (disciform scarring).

Choroidal neovascularization (CNV) commonly occurs in macular degeneration in addition to other ocular disorders and is associated with proliferation of choroidal endothelial cells, overproduction of extracellular matrix, and formation of a fibrovascular subretinal membrane. Retinal pigment epithelium cell proliferation and production of angiogenic factors appears to effect choroidal neovascularization.

Diabetic retinopathy (DR) is an ocular disorder characterized by excessive angiogenesis that develops in diabetes due to thickening of capillary basement membranes, and lack of contact between pericytes and endothelial cells of the capillaries. Loss of pericytes increases leakage of the capillaries and leads to breakdown of the blood-retina barrier. Diabetic retinopathy is the result of microvascular retinal changes. Hyperglycemia-induced pericyte death and thickening of the basement membrane lead to incompetence of the vascular walls. These damages change the formation of the blood-retinal barrier and also make the retinal blood vessels become more permeable. Small blood vessels—such as those in the eye—are especially vulnerable to poor blood sugar (blood glucose) control. An over-accumulation of glucose and/or fructose damages the tiny blood vessels in the retina. Macular edema can also develop when the damaged blood vessels leak fluid and lipids onto the macula. These fluids make the macula swell, which blurs vision. This damage also results in a lack of oxygen at the retina.

As the disease progresses, the lack of oxygen in the retina stimulates angiogenesis along the retina and in the clear, gel-like vitreous humour that fills the inside of the eye. Without timely treatment, these new blood vessels can bleed, cloud vision, and destroy the retina. Fibrovascular proliferation can also cause tractional retinal detachment. The new blood vessels can also grow into the angle of the anterior chamber of the eye and cause neovascular glaucoma.

Proliferative vitreoretinopathy is associated with cellular proliferation of cellular and fibrotic membranes within the vitreous membranes and on the surfaces of the retina. Retinal pigment epithelium cell proliferation and migration is common with this ocular disorder. The membranes associated with proliferative vitreoretinopathy contain extracellular matrix components such as collagen types I, II, and IV and fibronectin, and become progressively fibrotic.

Age-related macular degeneration (AMD) and diabetic retinopathy are the two leading causes of blindness in the developed world. Aflibercept, ranibizumab, and pegaptanib have improved the treatment options available for AMD patients. Ranibizumab is a Fab, and alfibercept is a fusion protein. They both bind vascular endothelial growth factor (VEGF) and have demonstrated the most impressive results to date treating AMD; however, only a minority of treated patients experience a significant improvement in visual acuity. Anti-angiogenic therapy focused on a target other than VEGF may overcome some of the limitations associated with agents that target the VEGF pathway.

The anti-CD105 antibodies described herein can be used to treat or prevent macular degeneration, CNV, diabetic retinopathy, or proliferative vitreoretinopathy. Described herein are methods of treating or preventing macular degeneration, CNV, diabetic retinopathy, macular edema or proliferative vitreoretinopathy via the administration of the antibodies described herein. The anti-CD105 antibodies described herein can also shrink blood vessels, inhibit endothelial cell proliferation associated with ocular disease, clear signs or symptoms of bleeding, treat cloudy vision, provide stasis of vision loss, improving vision, and/or prevent leakage of blood vessels. The anti-CD105 antibodies described herein can also be used in medicaments for the treatment of macular degeneration, CNV, diabetic retinopathy, macular edema, or proliferative vitreoretinopathy.

Additionally, anti-CD105 antibodies described herein can also be used in combination with known therapies and/or compounds for the treatment of macular degeneration, CNV, diabetic retinopathy, macular edema, or proliferative vitreoretinopathy. Examples of such compounds include, but are not limited to, ranibizumab, aflibercept, and pcgaptanib. In addition to the modes of administration described herein, the anti-CD105 antibodies can be administered via intravitreal routes. Non-limiting examples of intravitreal modes of administration include intravitreal injection and the use of intravitreal implants.

Patients can be assessed for improvement and responsiveness to treatment. Treatment includes, but is not limited to, decreasing the macular edema, decreased areas of CNV, and increased visual acuity. Measurements of signs or symptoms are as known in the art and are further described in the examples below.

In accordance with the embodiments described herein, the formulations described herein can be administered alone or in combination with one or more additional active or inactive agents. When combinations are used, simultaneous or sequential administration of the anti-CD105 antibodies and the anti-VEGF antibodies (antigen-binding fragments thereof) can be used.

Functional Assays

Formulations described herein can be assessed in a variety of in vitro, in vivo and ex vivo assays. Any suitable assay known to one of skill in the art can be used to monitor such effects. Several such techniques are described herein.

Assaying for CD105 Signaling and Function

CD105 (endoglin) is a member of the TGF-β receptor family that is expressed by proliferating endothelial cells, and normal levels of CD105 are needed for endothelial cell proliferation. CD105 is strongly expressed in the angiogenic vasculature of solid tumors, is involved in angiogenesis/vascular development and is an ancillary transforming growth factor β (TGF-β) receptor. CD105 is a homodimeric cell membrane glycoprotein that is expressed on leukemia cells and endothelial cells. Two isoforms of CD105, L-endoglin (170 kDa) and S-endoglin (160 kDa), differing in the amino acid sequence of their cytoplasmic tails, have been characterized.

CD105 expression is increased by cellular hypoxia through the production of hypoxia-inducible factor-1-α (HIF-1-α) and protects hypoxic cells from apoptosis. CD105 acts to modulate signaling of multiple kinase receptor complexes of the TGF-β superfamily, including TGF-β receptors (TGF-βR), activin receptor-like kinases (ALK) and activin receptors. In the absence of CD105, activation of TGF-β receptors results in phosphorylation of SMAD proteins that inhibit endothelial cell growth. However, activation of CD105 by TGF-β modulates SMAD protein phosphorylation. The end result is release of the growth inhibitory effects of TGF-β receptor activation on endothelial cells.

Prevention of CD105 activation by an anti-CD105 antibody acts synergistically with TGF-β to suppress endothelial cell growth. TGF-β can stimulate two distinct type I receptor/SMAD signaling pathways with opposite effects in endothelial cells. The TGF-β/ALK5 signaling pathway (A) leads to inhibition of cell proliferation and migration, whereas the TGF-β/ALK1 pathway (B) induces endothelial cell proliferation and migration. CD105, an accessory TGF-β receptor, highly expressed during angiogenesis, is essential for ALK1 signaling. In the absence of CD105, TGF-β/ALK5 signaling is predominant and maintains quiescent endothelium. High CD105 expression stimulates the ALK1 pathway and indirectly inhibits ALK5 signaling, thus promoting the activation state of angiogenesis.

In one non-limiting embodiment, the antibodies can be assessed with respect to inhibiting angiogenesis and endothelial cell proliferation. Binding of anti-CD105 antibodies to HUVECs does not prevent subsequent binding of TGF-β to HUVECs. Thus, direct suppression of the endothelial cell growth by anti-CD105 antibodies represents one of the underlying mechanisms by which anti-angiogenic and tumor-suppressive effects are observed in vivo. In another embodiment, the antibodies can be assessed with respect to blocking angiogenesis by preventing Smad1/5/8 phosphorylation and/or signaling. CD105 participates in the promotion of angiogenesis through signaling of the TGF-β/ALK1, which in turn involves the decrease and/or blockage of the phosphorylation of Smad2/3 proteins. In yet another embodiment, the antibodies can be assessed with respect to blocking angiogenesis by enhancing Smad2/3 phosphorylation and/or signaling.

Methods and techniques to assay the blocking or inhibitory effect of the antibodies provided herein on the TGF-β/ALK1 signaling pathway and/or the phosphorylation of Smad1/5 include, but are not limited to, known molecular techniques. By way of example, western blotting with antibodies specific to any of the proteins in the TGF-β/ALK5 or TGF-β/ALK1 pathways can be used to determine the inhibitory and/or stimulatory effect of the anti-CD105 antibodies disclosed herein on the TGF-β/ALK5 or TGF-β/ALK1 pathways. Similarly, detection of mRNA or regulation of the mRNA for the proteins involved in the TGF-β/ALK5 or TGF-β/ALK1 pathways can be used to assay the inhibitory and/or stimulatory effect of the antibodies disclosed herein. Additional methods for the assaying cell signaling for the TGF-β/ALK5 or TGF-β/ALK1 pathways are known in the art and are contemplated herein.

Activity of the anti-CD105 antibodies disclosed herein can be assessed using art recognized assays by, for example, binding assays such ELISAs, competitive ELISAs, surface plasmon resonance, and effect on HUVEC cells as described in more detail below.

SCID/Nude Mice

One method for assaying tumor growth makes use of SCID mouse, as follows: sub-confluent human M21 melanoma cells are harvested, washed, and resuspended in sterile PBS ($20\times10^6$ per mL). SCID mice are injected subcutaneously with 100 μL of M21 human melanoma cell ($2\times10^6$) suspension. Three days after tumor cell injection, mice are either untreated or treated intravenously or intraperitoneally (for example, 100 μg/mouse) with one or more control or test formulations. The mice are treated daily for 24 days. Tumor size is measured with calipers and the volume estimated using the formula $V=(L\times W^2)/2$, where V is equal to the volume, L is equal to the length, and W is equal to the width.

One method for assaying tumor growth makes use of nude mouse, as follows: MDA-MB-435 tumor cells ($0.4\times10^6$ cells/mouse) in 50 μl PBS are orthotopically implanted in the mammary fat pad of female nude mice (five to six weeks old). When tumors reached a mean volume of approximately 50-80 mm³, mice are randomized (at least 10/group) and intravenous or intraperitoneal treatment with one or more antibodies at 1 μg (0.05 mg/kg) per dose, 10 μg (0.5 mg/kg), 100 μg (5 mg/kg) or 200 μg (10 mg/kg), or 100 μg control antibody in 100 μl PBS, or vehicle PBS 100 μl twice per week is initiated; in some studies, an untreated group can also be evaluated. Tumor size is measured with calipers and the volume estimated using the formula $V=(L\times W^2)/2$, where V is equal to the volume, L is equal to the length, and W is equal to the width.

BALB/c Syngeneic Mouse Models

Alternatively, BALB/c syngeneic mouse models can also be utilized to assess tumor growth and inhibition thereof by the antibodies or described herein as exemplified by, for example, Tsujie et al., *Int. J. Oncology*, 29: 1087-1094 (2006).

Mice

Another assay measures angiogenesis in a chimeric mouse:human mouse model and is referred to as the chimeric mouse assay. The assay has been described in detail by others, and further has been described herein to measure angiogenesis, neovascularization, and regression of tumor tissues. See Yan, et al. (1993) *J. Clin. Invest.* 91:986-996.

The chimeric mouse assay is a useful assay model for in vivo angiogenesis because the transplanted skin grafts closely resemble normal human skin histologically and neovascularization of whole tissue is occurring wherein actual human blood vessels are growing from the grafted human skin into the human tumor tissue on the surface of the grafted human skin. The origin of the neovascularization into the human graft can be demonstrated by immunohistochemical staining of the neovasculature with human-specific endothelial cell markers.

The chimeric mouse assay demonstrates regression of neovascularization based on both the amount and extent of regression of new vessel growth. Furthermore, it is easy to monitor effects on the growth of any tissue transplanted upon the grafted skin, such as a tumor tissue. Finally, the assay is useful because there is an internal control for toxicity in the assay system. The chimeric mouse is exposed to any test reagent, and therefore the health of the mouse is an indication of toxicity. Other animal models described herein and known in the art can also be utilized in the methods described herein.

Rabbit Eye Assay

Another measure of angiogenesis is an in vivo rabbit eye model and is referred to as the rabbit eye assay. The rabbit eye assay has been described in detail by others, and has been used to measure both angiogenesis and neovascularization in the presence of angiogenic inhibitors as exemplified by D'Amato et al. (1994) *Proc. Natl. Acad. Sci. USA*, 91(9): 4082-4085.

The rabbit eye assay is a recognized assay model for in vivo angiogenesis because the neovascularization process, exemplified by rabbit blood vessels growing from the rim of the cornea into the cornea, is easily visualized through the naturally transparent cornea of the eye. Additionally, both the extent and the amount of stimulation or inhibition of neovascularization or regression of neovascularization can easily be monitored over time.

Finally, the rabbit is exposed to any test reagent, and therefore the health of the rabbit is an indication of toxicity of the test reagent.

Briefly, chicken chorioallantoic membrane (CAM) assays are performed and the effects on the developing vasculature are recorded at 48 hours after implantation of a 0.5% carboxymethylcellulose pellet containing one or more control or test compounds. Corneal neovascularization is induced by an implanted pellet of poly(hydroxyethyl methacrylate) (Hydron; Interferon Sciences, New Brunswick, N.J.) containing 650 ng of the potent angiogenic protein basic fibroblast growth factor (bFGF) bound to sucralfate (sucrose aluminum sulfate; Bukh Meditec, Copenhagen). The addition of sucralfate to the pellet protects the bFGF from degradation and provides for its slow release, thus producing consistent aggressive angiogenesis that is more pronounced than that induced by bFGF/Hydron alone. Release of bFGF from pellets containing sucralfate/Hydron can be detected in vitro for up to 4 days after the pellets are formed compared to just 1 day for pellets with Hydron alone. Pellets are made by mixing 110 μl of saline containing 12 μg of recombinant bFGF (Takeda, Osaka) with 40 mg of sucralfate; this suspension is added to 80 μl of 12% (wt/vol) Hydron in ethanol. Aliquots (10 μl) of this mixture are then pipetted onto Teflon pegs and allowed to dry producing approximately 17 pellets.

A pellet is implanted into corneal micropockets of each eye of an anesthetized female New Zealand White rabbit, 2 mm from the limbus, followed by a single topical application of erythromycin ointment on the surface of the cornea. Histologic examination on consecutive days demonstrates progressive blood vessel growth into the cornea toward the pellet with only rare inflammatory cells seen. This angiogenic response is not altered by severe immune suppression with total body irradiation, and pellets with sucralfate alone do not induce angiogenesis. New vessels are primarily induced by the bFGF rather than by inflammation. The animals are fed daily from 2 days after implantation by gastric lavage with one or more compounds suspended in 0.5% carboxymethylcellulose or vehicle alone. Immunosuppressed animals receive total body radiation of 6 Gy for 6 minutes immediately prior to implantation of the pellets. This dose of radiation results in a marked leukocytopenia with >80% reduction in the leukocyte count by day 2 and >90% reduction by day 3, results that are consistent with previous reports.

Animals are examined with a slit lamp every other day in a masked manner by the same corneal specialist (M.S.L.).

The area of corneal neovascularization is determined by measuring with a reticule the vessel length (L) from the limbus and the number of clock hours (C) of limbus involved. A formula is used to determine the area of a circular band segment: $C/12 \times 3.1416 [r^2-(r-L)^2]$, where r=6 mm, the measured radius of the rabbit cornea. The uniform contiguous band of neovascularization adjacent to the pellet is measured, thus, the total inhibition of neovascularization can be assessed.

Mouse Matrigel Pug Angiogenesis Assays

To confirm the effects of a formulation on angiogenesis, a mouse Matrigel plug angiogenesis assay can be used. Various growth factors (e.g., IGF-1, bFGF or VEGF) (250 ng) and Heparin (0.0025 units per/mL) are mixed with growth factor reduced Matrigel as previously described (Montesano, et al., *J. Cell Biol.* 1983, 97:1648-1652; Stefansson, et al., *J. Biol. Chem.* 2000, 276:8135-8141). Formulations described herein or control antibodies can be included in the Matrigel preparations utilizing one or more dosage groups of animals. In control experiments, Matrigel is prepared in the absence of growth factors. Mice are injected subcutaneously with 0.5 mL of the Matrigel preparation and allowed to incubate for one week. Following the incubation period, the mice are sacrificed and the polymerized Matrigel plugs surgically removed. Angiogenesis within the Matrigel plugs is quantified by two established methods, including immunohistochemical analysis and hemoglobin content (Furstenberger, et al., *Lancet.* 2002, 3:298-302; Volpert, et al., *Cancer Cell* 2002, 2(6):473-83; and Su, et al., *Cancer Res.* 2003, 63:3585-3592). For immunohistochemical analysis, the Matrigel plugs are embedded in OCT, snap frozen and 4 μm sections prepared. Frozen sections are fixed in methanol/acetone (1:1). Frozen sections are stained with polyclonal antibody directed to CD31. Angiogenesis is quantified by microvascular density counts within 20 high powered (200×) microscopic fields.

Hemoglobin content can be quantified as described previously (Schnaper, et al., *J. Cell Physiol.* 1993, 256:235-246; Montesano, et al., *J. Cell Biol.* 1983, 97:1648-1652; Stefansson, et al., *J. Biol. Chem.* 2000, 276:8135-8141; and Gigli, et al., *J. Immunol.* 1986, 100:1154-1164). The Matrigel implants are snap frozen on dry ice and lyophilized overnight. The dried implants are resuspended in 0.4 mL of 1.0% saponin (Calbiochem) for one hour, and disrupted by vigorous pipetting. The preparations are centrifuged at 14,000×g for 15 minutes to remove any particulates. The concentration of hemoglobin in the supernatant is then determined directly by measuring the absorbency at 405 nm and compared to a standard concentration of purified hemoglobin.

Methods of Assaying Cell Migration

Assays for cell migration have been described in the literature, e.g., by Brooks, et al., *J. Clin. Invest* 1997, 99:1390-1398 and methods for measuring cell migration are known to those of skill in the art. In one method for measuring cell migration described herein, membranes from transwell migration chambers are coated with substrate (here, CD105 and/or VEGF), the transwells washed, and non-specific binding sites blocked with BSA. Tumor cells from sub-confluent cultures are harvested, washed, and resuspended in migration buffer in the presence or absence of assay antibodies. After the tumor cells are allowed to migrate to the underside of the coated transwell membranes, the cells remaining on the top-side of the membrane are removed and cells that migrate to the under-side are stained with crystal violet. Cell migration is then quantified by direct cell counts per microscopic field.

Methods of Assaying Cell Proliferation

Cell proliferation can be assayed by methods known to those of skill in the art. As described herein, sub-confluent human endothelial cells (HUVECs) can be resuspended in proliferation buffer containing low (5.0%) serum in the presence or absence of CM (25 μL) from ECV or ECVL cells, and endothelial cells allowed to proliferate for 24 hours. Proliferation can be quantified by measuring mitochondrial dehydrogenase activity using a commercially available WST-1 assay kit (Chemicon). Also, as described herein, proliferation can be quantified by measuring $^3$H incorporation using standard methods. (She et al., *Int. J. Cancer,* 108: 251-257 (2004)).

Other methods of assessing cell proliferation are known in the art and are contemplated herein. Further non-limiting examples are described in more detail in the examples.

Methods of Inducing CDC, ADCC and Opsonization

Various therapies have been directed to augmenting the body's natural immune response to transformed cells. Conventional effector methods include complement dependent cytolysis ("CDC"), antibody dependent cellular cytotoxicity ("ADCC") and phagocytosis (clearance by reticuloendothelial system after the target cell is coated with immunoglobulin). It is known that in the presence of antibodies, certain effector cells, such as lymphoid cells having surface bound receptors for the Fc regions of antibodies, mediate an antibody dependent cellular cytotoxicity ("ADCC") reaction against target cells. By means of ADCC, these effector cells exert cytolytic activity against such target cells.

Two types of ADCC reactions have been demonstrated in vitro. In classical ADCC reactions, effector cells attach to antibody-coated target cells and subsequently cause cytolysis of the target cells (A. H. Greenberg et al., "Characteristics Of The Effector Cells Mediating Cytotoxicity Against Antibody-Coated Target Cells," *Immunology,* 21, p. 719 (1975)). This attachment between effector and target cell results from the interaction of the Fc region of the antibody coating the target cell and the Fc receptor of the effector cell. One disadvantage of this type of ADCC reaction is that it may be hampered by circulating antigen-antibody complexes, often associated with various diseases, which compete with the target-cell bound antibody for the Fc receptors of the effector cells (I. C. M. MacLennan, "Competition For Receptors For Immunoglobulin On Cytotoxic Lymphocytes," *Clin. Exp. Immunol.,* 10, p. 275 (1972)). Due to this drawback of classical ADCC, a second type of ADCC reaction—antibody-directed ADCC—can be utilized. In antibody-directed ADCC, the target-specific antibody is first attached to the effector cell and the resulting complex is then "directed," via the antibody, to its specific antigen on the target cell surface. Advantageously, antibody-directed ADCC may not be affected by the presence of antigen-antibody complexes circulating in the host system. The interaction between antibodies and effector cells via Fc region/Fc receptor attachment is normally weak. And, in some instances, antibodies do not remain associated with effector cells for a period of time sufficient to permit lysis of target cells. In view of this potential problem, antibodies have been attached to the effector cells using pre-treatment with polyethylene glycol and a mixture of phthalate oils (J. F. Jones and D. M. Segal, "*J. Immunol.,* 125, pp. 926-33 (1980)). The applicability of this method for in vivo treatments, however, may be diminished by the toxic effects that any polyethylene glycol and phthalate oil residues on the antibody-effector cell complex may have on the body.

Alternatively, a method has been proposed for enhancing antibody-directed ADCC by adjuvant chemotherapy with cytotoxic drugs (I. R. Mackay et al., *Cancer Immunol. Immunother.*, 16, pp. 98-100 (1983)). Assays for testing for ADCC are well-known in the art, such as for example, U.S. Pat. No. 5,756,097.

Accordingly, the present embodiments provide antibodies that can bind to cells having a role in neovascularization or angiogenesis of that can enhance phagocytosis and killing of the cells and thereby enhance protection in vivo. Also provided are other antibodies and functional fragments thereof that immunoreact, specifically bind to, or preferentially bind to a binding site or epitope to which such antibodies can bind and which have the same effect.

The antibodies can also be opsonic, or exhibit opsonic activity, for cells having a role in neovascularization or angiogenesis (e.g., endothelial cells). As those in the art recognize, "opsonic activity" refers to the ability of an opsonin (generally either an antibody or the serum factor C3b) to bind to an antigen or cell receptor to promote attachment of the antigen or cell receptor to a phagocyte and thereby enhance phagocytosis. Certain cells become extremely attractive to phagocytes such as neutrophils and macrophages when coated with an opsonic antibody and their rate of clearance from the bloodstream is strikingly enhanced. Opsonic activity may be measured in any conventional manner as described, for example, in U.S. Pat. No. 6,610,293.

In another non-limiting embodiment, a patient having a neovascular disorder or an angiogenesis dependent disorder sheds antigens/peptides (e.g., CD105) from the angiogenesis. These antigens/peptides can be "tumor associated antigens." Such patients can be systemically administered an antibody to the antigen/peptide (e.g., CD105) and can initiate any of the pathways described herein to induce CDC, ADCC, opsonization, or any other form of cell-mediated killing.

Additional Assays

Other assays known in the art can also be used to test the effect of the formulations described herein such as, for example, those described in the examples below.

EXAMPLES

The application may be better understood by reference to the following non-limiting examples, which are provided as exemplary embodiments of the application. The following examples are presented in order to more fully illustrate exemplary embodiments and should in no way be construed, however, as limiting the broad scope of the application. While certain embodiments of the present application have been shown and described herein, it will be obvious that such embodiments are provided by way of example only. Numerous variations, changes, and substitutions may occur; it should be understood that various alternatives to the embodiments described herein may be employed in practicing the methods described herein.

Example 1: Exemplary Dosage Schedules for Administration

Optimal dosage schedules of administration of antibodies and antigen-binding fragments thereof described herein can be determined using art-recognized methods and as described above.

In one non-limiting embodiment, the antibodies described herein can be administered to a subject over various time frames. The dose(s) of an antibody or antigen-binding fragment thereof can be administered twice a week, weekly, every two weeks, every three weeks, every 4 weeks, every 6 weeks, every 8 weeks, every 12 weeks, or any combination of weeks therein. Dosing cycles are also contemplated such as, for example, administering antibodies once or twice a week for 4 weeks, followed by two weeks without therapy. Additional dosing cycles including, for example, different combinations of the doses and weekly cycles described herein are also contemplated herein.

Example 2: BIAcore (Surface Plasmon Resonance: SPR) Analysis

Affinity of antibodies can be assessed using, for example, BIAcore analysis using standard protocols. Briefly, anti-histidine tag antibody is coupled to a BIAcore chip for the capture of His-tagged recombinant human CD105 which will in turn be used to measure the binding of an anti-CD105 antibody. Development of the SPR assay is performed in a minimum of 2 chip preparation batches plus 8 analytical batches. The following parameters are assessed in the development of the assay:

(a) Coupling of Anti-his Antibody to CM5 Chips

An anti-his tag antibody is coupled to a BIAcore CM5 chip by conventional amine chemistry using EDC/NHS. The reaction conditions (concentration and pH) will be optimized (b) Binding of Human CD105 and Regeneration of Biosensor Chip Conditions are tested for binding of human CD105 and regenerating the chip using various buffers (based on previous experience) to elute the bound antibody. Once a candidate method for regeneration has been developed, the binding capacity and background of a single chip surface are measured over at least 25 cycles. The target is to obtain on average an increase in background <10 RU per cycle and decrease in capacity <1% per cycle.

(c) Binding of human CD105

The dose response of human CD105 is measured in order to determine a suitable concentration to approach maximal binding.

(d) Binding of Anti-CD105 Antibody

The dose response of anti-CD105 antibody is measured in order to determine a suitable range for kinetic or equilibrium binding experiments (which can include comparison of relative kinetic constants, $k_a$ and $k_d$ or a comparison of relative potency by the parallel line method).

(e) Pre-Validation Experiments

The binding experiments is repeated at least three times under the chosen conditions using different chips, different flow cells and on different occasions in order to obtain preliminary information about the precision and accuracy of the measurements. All BIAcore experiments are carried out at 25° C. in HBS-EP running buffer.

Example 3: ELISA for Anti-CD105 Antibody Binding

An ELISA can be used to assay binding of anti-CD105 antibodies to CD105. Briefly, an ELISA is performed according to the following steps:
1. Coat a plate with MAB9811-01 (monoclonal anti-CD105 antibody) at 1500 ng/ml in PBS, 100 µl/well. Cover the plate with a sealer and incubate overnight (16-24 hours) at 4° C.
2. Wash the plate 2× with 200 µl of PBS (without Tween).
3. Wash the plate 3× with PBS containing Tween (PBS-T).

4. Add 100 µl/well of CD105 at 100 ng/ml in PBS-T with 0.1% BSA and incubate 60 minutes at room temperature.
5. Wash the plate 3× with PBS-T.
5. In test wells: add 100 µl/well of anti-CD105 antibodies at 20, 10, 4, 2, 1, 0.5 and 0.2 ng/ml (diluted in PBS-T with 0.1% BSA) and incubate 60 minutes at room temperature. In negative control wells: add 100 µl/well of isotype matched control antibody.
7. Wash the plate 3× with PBS-T.
8. Add 100 µl/well of Goat anti-Human IgG conjugated to HRP, diluted 1:10000 in PBS-T with 0.1% BSA to all wells; incubate 30-60 minutes at room temperature.
9. Wash the plate 5× with PBS-T.
10. Add 100 µl/well of TMB substrate solution and incubate uncovered in the dark for 15 minutes.
11. Stop the reaction by addition of 100 µl/well of TMB Stop Solution.

Samples are run in triplicate and the optical density is read to construct a standard curve and determine the binding constant. Statistical analysis is conducted using the Student's t-test or another standard test.

One would understand that a similar protocol can be used to test for binding of antibodies to VEGF.

Example 4: Antibody Avidity and Number of Available Epitopes on CD105-Expressing Cells Antibody avidity and number of available epitopes on CD105-expressing cells can be assessed utilizing Scatchard plot analyses using standard protocols.

Briefly, Scatchard plot analyses of direct binding of radiolabeled anti-CD105 antibodies to CD105-expressing KM-3 leukemia cells and sub-confluent proliferating HUVECs are carried out. The purified anti-CD105 antibodies are individually radiolabeled with $^{125}$I using Iodo-Gen and according to standard methods known to those skilled in the art. The radiolabeled anti-CD105 antibodies are assayed for the iodine atoms per IgG molecule on the average, respectively. Titration experiments are carried out using a fixed amount (0.1 µg) of each $^{125}$I-labeled mAb and 2-fold serial increments of CD105-expressing KM-3 or HUVEC cells to determine antigen-binding activity. Analysis of Scatchard plot of binding data is carried out according to known methods. An equilibrium constant and an average maximal number of mAb bound/cell are estimated by this analysis.

Example 5: Western Blots Assay for Blocking Activity

The ability of anti-CD105 antibodies to block CD105 stimulated activation of cells that express CD105 can be assayed via western blots to detect the phosphorylation of the proteins involved in the CD105 signaling pathway.

Western blot analyses are performed to identify phosphorylated Smad1/5/8 or Smad2 as according to known western blotting techniques. PSmad1 and PSmad2 antibodies specifically recognize phosphorylated Smad1/5 or phosphorylated Smad2 in non-transfected endothelial cells. Primary antibodies against Smad1, Smad2, Smad5, Id1 (Santa Cruz) and CD105 are utilized to detect molecules in samples. Detection is performed by enhanced chemoluminescence (ECL).

Example 6: Inhibition of HUVEC Growth and $^3$H-Thymidine Incorporation Assay A number of assays are available to assess inhibition of cell growth.

In one example, HUVECs are cultured in 75-cm$^2$ flasks (Falcon, Becton-Dickinson, Franklin Lakes, N.J.) in a CO$_2$ incubator at 37° C. under sub-confluent conditions. Cells are detached by incubating with Hanks' balanced salt solution with 15 mM EDTA in 25 mM HEPES buffer, pH 7.3, at 37° C. for 15 min. After washing twice with ice-cold PBS, cells are re-suspended in endothelial cell growth medium at a concentration of 25,000 cells/ml.

In additional experiments, human umbilical vein endothelial cells (HUVECs) are suspended and cultured in an endothelial cell growth medium free of FBS and bovine brain extracts. A 200 µl aliquot of cell suspension is seeded to each well of 96-well culture plates. Cells are cultured at 37° C. in a CO$_2$ incubator overnight before anti-CD105 antibodies, anti-VEGF antibodies, a combination of anti-CD105 antibodies and anti-VEGF antibodies, control IgG or TGF-β1 are added in triplicate. Culture plates are kept in the incubator for 72 hr, during which fresh media and antibodies or controls are replaced every 24 hr. $^3$H-thymidine (1 µCi) is added into each well and the plates are incubated for 20 hr. Cells are washed with PBS followed by treatment with 100 µl/well trypsin-EDTA (0.05% trypsin, 0.53 mM EDTA) at 37° C. for 15 min. Cells are harvested onto glass fiber filters (Wallac Printed FiltermatA) using Harvester 96 (TOMTEC, Hamden, Conn.) and $^3$H-radioactivity is determined in a Trilux 1540 MicroBeta Liquid Scintillation and Luminescence Counter (Wallac, Turku, Finland).

Example 7: Assay for Inhibition of Cell Migration

Migration (chemokinesis) as a measure of cell proliferation and activation is measured using a Boyden chamber.

Briefly, cell migration is assessed as follows: a Costar nucleopore filter (8 mm pore) is coated with fibronectin overnight at 4° C. The chamber is washed with phosphate-buffered saline (PBS) and the lower chamber was filled with DMEM with or without serum and with or without TGF-β3. Cells are trypsinized and suspended at a final concentration of 50,000 cells/ml in DMEM in the presence of a control antibody, an anti-CD105 antibody, an anti-VEGF antibody or a combination thereof. A 150 µl aliquot of the cell suspension is added to the upper chamber and incubated at 37° C. After 16 hrs, the cells are washed and the upper surface is wiped to remove the non-migrating cells. The membranes are fixed in methanol, washed with water, stained and the numbers of cells present on the lower surface are counted.

Example 8: ADCC Assay

The antibodies described herein can be assessed with respect to their ability to generate IL-2 activated natural killer (NK) cells and to induce ADCC using, for example, the following protocols.

NK Isolation and Generation of IL-2 Activated NK Cells

PBMC are isolated and allowed to rest for 24 hrs at 4° C. in RPMI with 10% FBS. PBMC are then placed in RPMI with 2% FBS (Total Volume=50 mL), and 10 mL of the cell suspension are plated in a petri dish. PBMC are incubated for 2 hrs at 37° C. and the non-adherent cells are collected. NK cells are cultured at 8×10$^6$/mL with 1000 U/mL IL-2 for 48 hrs, followed by normal culturing for 5-8 days before using in an assay.

Natural Cytotoxicity and ADCC Assays

NK cells are scraped from the culture and collected in a 50 mL conical tube. Cells are washed once with RPMI Complete and Spun at 1200 rpm for 10 minutes. NK cells are then re-suspended in 5 mL RPMI Complete media and counted. Prior to performing the assay, the NK cell count is normalized to a effector: target ratio of 10:1. Normalized NK cells are plated and 10 μL of anti-CD105 antibodies added into designated wells and incubated for 30 minutes at 37° C. Control samples include untreated or control-antibody treated cell populations.

Target cells of interest are collected (HUVEC cells), washed, spun at 1200 rpm for 10 minutes, and re-suspended in 5 mL RPMI Complete media. Target cells are washed again and re-suspended in Serum Free RPMI to a final concentration of 1×10$^6$ cells/mL. Target cells are then labeled with a final concentration of 5 μg/mL Calcein AM for 1 hr at 37° C., followed by a two washes with RPMI Complete. Target cells are then re-suspended and added to the NK cell wells. The target cell/NK c$^e$ll combination is incubated at 37° C. for 4 hours. After incubation, the plates are spun at 1200 rpm for 5 minutes, and the cells are washed and re-suspended in DPBS. The fluorescence is read using Excitation/Emission of 450/530 nm and the emission is a measure of the cell killing mediated by the antibodies.

Example 9: Stability Assessment of TRC105 (an Anti-CD105 Antibody) Formulations

The present inventors identified formulations that provided adequate stability for concentration higher than 5 mg/ml of TRC105. Initial studies showed that TRC105 could be concentrated to at least 25 mg/ml without any apparent solubility issues. Therefore, 25 mg/ml TRC105 was selected as the initial concentration for screening studies. During the course of these studies, formulations as high as 50 mg/ml TRC105 were evaluated. Additional formulations with concentrations of 7 mg/ml TRC105 and 100 mg/ml TRC105 were also evaluated.

Procedures

Ultraviolet (UV) Absorbance Spectroscopy.

UV spectroscopy was used to determine protein concentration in various stability samples. The absorbance at 280 nm of bulk substance (7.0 mg/mL) was determined to be 1.13 using a 1 mm pathlength cell, leading to an extinction coefficient of 1.61 mL/mg*cm. This value was used for all calculations in this project. Further measurements were performed using a 0.0096 cm cell, which was more suited for high concentration samples.

Incubation of TRC105 Thermal Stability Samples.

Each thermal stability formulation was passed through a 0.22 micron Millex filter with a Luer lock syringe attachment and then aliquoted into 1 mL lyophilization vials. Each vial was sealed with a butyl stopper and crimped with an aluminum cap. Samples were placed at the indicated temperature in stability chambers and removed after the indicated incubation period, in weeks.

Freeze-Thaw and Agitation of TRC105.

Freeze-thaw (F/T) samples were frozen for 25 minutes, then thawed for 25 minutes either zero, 3 or 5 times. All freezing was performed at −80° C. Thawed samples were examined for complete thawing before returning to freezer. Each freeze-thaw sample contained 100 μL of solution and was stored in 0.5 mL Eppendorf tubes. Each sample contained 0.1% F68, 0.005% Tween 80, or no surfactant.

Agitation study samples were prepared at 350 mL per vial, and were labeled as either quiescent or shaken. All samples were moved to a cold room at 4° C. Samples labeled as shaken were placed on an orbital shaker operating at 150 RPM. Quiescent samples were placed on the shelf next to the orbital shaker. Each sample contained 0.1% F68, 0.005% Tween 80, or no surfactant. Samples were incubated for 24 hours at the indicated conditions.

Size Exclusion Chromatography (SEC).

A mobile phase was prepared containing 0.2 M sodium phosphate monobasic and adjusted to pH 7.0 using 1.0 M sodium hydroxide. A TSK Gel G3000 PW×1 column (7.8 mm×30 cm, 7 μm particles # P0047-02PN) was used for all separations. A flow rate of 1 mL/min was used, and the detection wavelength was set to 280 nm. Injection volume was 2 μL for 25 mg/mL samples, and 1 μL for 50 mg/mL samples. Buffer blanks were run before each triplicate sample analysis, and these chromatograms were subtracted appropriately. All integration of peaks was performed in Chromeleon 6.08.

Capillary IEF (cIEF).

The capillary isoelectric focusing (cIEF) analysis was conducted as described in the PA 800 plus Application Guide published by Beckman Coulter. A more detailed description can be found in Mack et al. (*Electrophoresis* 2009, 30 (23), 4049-4058). All analyses were conducted using a Beckman Coulter P/ACE™ MDQ system (Beckman Coulter, Inc.; Brea, Calif.) operated at ambient temperature with a 30 cm total length (20 cm effective) neutral capillary (50 μm i.d.). The neutral capillary was prepared by immobilizing poly (acrylamide) to the capillary wall using a method described Gao et al. (*Anal Chem* 2004, 76 (24), 7179-7186). All of the cIEF samples were prepared by mixing the protein of interest at 0.25 mg/mL with a mixture of 3M urea-cIEF gel containing ampholyte, cathodic stabilizer, anodic stabilizer, and pI markers. Sample was pressure injected at 9.5 psi into the capillary for 4.1 min, after which time it was focused by applying a voltage of 25 kV for 15 min between anolyte and catholyte. This step was followed by chemical mobilization at 30 kV for 30 min between anolyte and chemical mobilizer. The pI markers and the protein of interest were detected with absorbance at 280 nm during the mobilization step. The pI of the protein was calculated from the resultant regression equation of pI vs. first peak moment obtained from the pI standards.

Results and Discussion

Study 1

Samples of TRC105 were successfully concentrated to concentrations higher than 5 mg/mL. As a result, Study 1 was conducted using a protein concentration of 25 mg/mL. Samples were stored for two weeks at 40° C. Fifteen formulations were prepared focusing on the effects of pH and buffer composition (Table 2). The primary analytical method used to evaluate the stability of these samples was SEC. After storage for two weeks at 40° C., very little change was seen by SEC, either in monomer content or the amount of high molecular weight aggregate (Table 3). All of the formulations still contained more than 99% monomer after storage.

TABLE 2

Composition of the TRC105 formulation evaluated in Study 1

| Formulation Number | pH | phos (mM) | His (mM) | citrate (mM) | acetate (mM) | NaCl (mM) | trehalose (mM) |
|---|---|---|---|---|---|---|---|
| F01 | 7 | 20 | 0 | 0 | 0 | 130 | 0 |
| F02 | 6 | 20 | 0 | 0 | 0 | 130 | 0 |
| F03 | 6 | 0 | 20 | 0 | 0 | 130 | 0 |
| F04 | 5 | 0 | 20 | 0 | 0 | 130 | 0 |
| F05 | 6 | 0 | 0 | 20 | 0 | 130 | 0 |
| F06 | 5 | 0 | 0 | 20 | 0 | 130 | 0 |
| F07 | 4 | 0 | 0 | 0 | 20 | 130 | 0 |

TABLE 2-continued

Composition of the TRC105 formulation evaluated in Study 1

| Formulation Number | pH | phos (mM) | His (mM) | citrate (mM) | acetate (mM) | NaCl (mM) | trehalose (mM) |
|---|---|---|---|---|---|---|---|
| F08 | 5 | 0 | 0 | 0 | 20 | 130 | 0 |
| F09 | 5 | 0 | 20 | 0 | 0 | 0 | 240 |
| F10 | 5 | 0 | 0 | 20 | 0 | 0 | 240 |
| F11 | 5 | 0 | 0 | 0 | 20 | 0 | 240 |
| F12 | 6 | 10 | 0 | 0 | 0 | 0 | 240 |
| F13 | 6 | 0 | 10 | 0 | 0 | 0 | 240 |
| F14 | 6 | 10 | 0 | 0 | 0 | 80 | 120 |
| F15 | 6 | 0 | 10 | 0 | 0 | 80 | 120 |

TABLE 3

Summary of monomer and aggregate levels as measured by SEC for formulations from Study 1 at initial and two week (t2) time points

| Formulation Number | pH | initial % aggregates | initial % monomer | two weeks % aggregates | two weeks % monomer |
|---|---|---|---|---|---|
| F01 | 7 | 0.32 | 99.54 | 0.48 | 99.52 |
| F02 | 6 | 0.19 | 99.70 | 0.22 | 99.71 |
| F03 | 6 | 0.19 | 99.78 | 0.14 | 99.82 |
| F04 | 5 | 0.14 | 99.82 | 0.13 | 99.85 |
| F05 | 6 | 0.19 | 99.78 | 0.28 | 99.71 |
| F06 | 5 | 0.13 | 99.83 | 0.21 | 99.77 |
| F07 | 4 | 0.11 | 99.86 | 0.10 | 99.88 |
| F08 | 5 | 0.11 | 99.85 | 0.26 | 99.72 |
| F09 | 5 | 0.16 | 99.81 | 0.09 | 99.90 |
| F10 | 5 | 0.13 | 99.84 | 0.19 | 99.79 |
| F11 | 5 | 0.15 | 99.82 | 0.16 | 99.82 |
| F12 | 6 | 0.19 | 99.78 | 0.53 | 99.45 |
| F13 | 6 | 0.21 | 99.76 | 0.15 | 99.81 |
| F14 | 6 | 0.20 | 99.76 | 0.45 | 99.52 |
| F15 | 6 | 0.21 | 99.79 | 0.21 | 99.77 |

TRC105 was found to be very stable.

Study 2

With the results from Study 1 in hand, a new study was designed. In Study 2, the pH ranged from 4.0 to 5.5, with acetate, histidine, and citrate were evaluated. The tonicity modifiers/stabilizers selected were sorbitol and trehalose. Finally, in addition to formulations at 25 mg/ml, three formulations at 50 mg/ml were examined.

TABLE 4

Composition of the TRC105 formulation evaluated in Study 2

| Formulation Number | pH | Protein Mg/ml | His (mM) | citrate (mM) | acetate (mM) | sorbitol | trehalose |
|---|---|---|---|---|---|---|---|
| F01 | 5.5 | 25 | 0 | 0 | 20 | 0 | 0 |
| F02 | 4.5 | 25 | 0 | 0 | 20 | 0 | 0 |
| F03 | 5.5 | 25 | 0 | 20 | 0 | 0 | 0 |
| F04 | 5.5 | 25 | 20 | 0 | 0 | 0 | 0 |
| F05 | 4.5 | 25 | 0 | 0 | 10 | 0 | 0 |
| F06 | 4.0 | 25 | 0 | 0 | 10 | 0 | 0 |
| F07 | 5.5 | 25 | 20 | 0 | 0 | 240 | 0 |
| F08 | 5.5 | 25 | 20 | 0 | 0 | 0 | 240 |
| F09 | 4.0 | 25 | 0 | 0 | 20 | 240 | 0 |
| F10 | 4.0 | 25 | 0 | 0 | 20 | 0 | 240 |
| F11 | 5.5 | 25 | 0 | 10 | 0 | 240 | 0 |
| F12 | 5.5 | 25 | 0 | 10 | 0 | 0 | 240 |
| F13 | 5.5 | 25 | 10 | 0 | 0 | 240 | 0 |
| F14 | 5.5 | 25 | 10 | 0 | 0 | 0 | 240 |
| F15 | 4.0 | 50 | 0 | 0 | 10 | 0 | 0 |
| F16 | 5.0 | 50 | 0 | 0 | 20 | 0 | 0 |
| F17 | 5.5 | 50 | 20 | 0 | 0 | 240 | 0 |

Given the stability of TRC105, these sample were stored for four weeks at 40° C. in order to try to distinguish formulations to a greater degree. The primary screening tool was SEC.

TABLE 5

Summary of monomer and aggregate levels as measured by SEC for formulations from Study 1 at initial and week four time points

| Formulation Number | pH | buffer | initial % aggregates | initial % monomer | four weeks % aggregates | four weeks % monomer |
|---|---|---|---|---|---|---|
| F01 | 5.5 | acetate | 0.17 | 99.83 | 0.27 | 99.73 |
| F02 | 4.5 | acetate | 0.10 | 99.90 | 0.16 | 99.84 |
| F03 | 5.5 | citrate | 0.14 | 99.86 | 0.22 | 99.78 |
| F04 | 5.5 | His | 0.17 | 99.83 | 0.13 | 99.87 |
| F05 | 4.5 | acetate | 0.11 | 99.89 | 0.14 | 99.86 |
| F06 | 4.0 | acetate | 0.10 | 99.90 | 0.12 | 99.88 |
| F07 | 5.5 | His | 0.15 | 99.85 | 0.13 | 99.87 |
| F08 | 5.5 | His | 0.23 | 99.77 | 0.16 | 99.84 |
| F09 | 4.0 | acetate | 0.14 | 99.86 | 0.15 | 99.85 |
| F10 | 4.0 | acetate | 0.15 | 99.85 | 0.15 | 99.85 |
| F11 | 5.5 | citrate | 0.16 | 99.84 | 0.30 | 99.70 |
| F12 | 5.5 | citrate | 0.21 | 99.79 | 0.28 | 99.72 |
| F13 | 5.5 | His | 0.19 | 99.81 | 0.15 | 99.85 |
| F14 | 5.5 | His | 0.27 | 99.73 | 0.16 | 99.84 |
| F15 | 4.0 | acetate | 0.17 | 99.83 | 0.16 | 99.84 |
| F16 | 5.0 | acetate | 0.19 | 99.81 | 0.85 | 99.15 |
| F17 | 5.5 | His | 0.24 | 99.76 | 0.26 | 99.74 |

Similar to what was seen in Study 1, the monomer content of nearly all of the formulations is above 99.5%, even after one month at 40° C. (Table 5). One sample seems to show an increased level of aggregation and this was F16; this sample was not retested to see if this was a real result. The indication is that pH 4 in acetate of pH 5.5 in histidine appears to provide adequate and comparable stability. Given concerns of citrate and irritation, it was removed from further consideration.

These samples were also analyzed using capillary isoelectric focusing (cIEF). The overall center of cIEF electropherogram was calculated as the first moment. These values can be considered to be the average pI values of the sample (Table 6).

TABLE 6

Average pI value for TRC formulations from Study 2 at initial and four weeks' time points

| Form No | pH | buffer | Initial | 4 weeks |
|---|---|---|---|---|
| F01 | 5.5 | acetate | 8.97 | 8.88 |
| F02 | 4.5 | acetate | 8.76 | 8.94 |
| F03 | 5.5 | citrate | 8.84 | 8.88 |
| F04 | 5.5 | His | 8.94 | 8.88 |
| F05 | 4.5 | acetate | 8.78 | 8.87 |
| F06 | 4.0 | acetate | 8.86 | 8.89 |
| F07 | 5.5 | His | 8.87 | 8.88 |
| F08 | 5.5 | His | 8.93 | 8.87 |
| F09 | 4.0 | acetate | 8.92 | 8.90 |
| F10 | 4.0 | acetate | 8.92 | 8.92 |
| F11 | 5.5 | citrate | 8.96 | 8.87 |
| F12 | 5.5 | citrate | 8.92 | 8.85 |
| F13 | 5.5 | His | 8.91 | 8.90 |
| F14 | 5.5 | His | 8.95 | 8.92 |
| F15 | 4.0 | acetate | 8.90 | 8.87 |
| F16 | 5.0 | acetate | 8.90 | 8.86 |
| F17 | 5.5 | His | 8.95 | 8.93 |

Overall, the change in pI value for any of the formulations is small, suggesting that deamidation, that is, hydrolysis of Asn side chains to form charged Asp products, is relatively slow (Table 6). Thus, these formulations of TRC105 appear to be physically stable (i.e., little or no aggregation) and chemically stable (i.e., no fragmentation and little or no deamidation).

The other concern was whether these higher concentration formulations displayed adverse viscosity, thereby limiting their clinical utilization.

TABLE 7

Dynamic viscosity of TRC105 in acetate and histidine buffers at ~25 and ~50 mg/ml

| Formulation | pH | [Protein] | Viscosity (cSt) |
|---|---|---|---|
| 20 mM acetate | 4.0 | 25.1 | 1.19 ± 0.01 |
|  | 4.0 | 51.8 | 1.53 ± 0.01 |
| 20 mM histidine | 5.5 | 23.8 | 1.22 ± 0.01 |
|  | 5.5 | 47.6 | 1.65 ± 0.04 |

Even at 50 mg/ml, TRC105 exhibits a viscosity of less than 2 cSt, well below any value that would cause concern for limiting handling and administration (See, Table 7).

Agitation Study

While thermal stress is useful for distinguishing formulations of differing stability, it is not the only stress a protein may encounter. Interfacial damage of proteins is common and the sensitivity to interfacial stress must be evaluated. This was done using agitation and repeated freeze-thaw (F/T) cycling.

TABLE 8

Monomer content by SEC for TRC105 formulations that were agitated for 24 hours at 150 rpm and matching quiescent samples. All samples were held at 4° C.

| Formulation | Surfactant | protein | Monomer (Q) | Monomer (S) |
|---|---|---|---|---|
| pH 5, 20 mM acetate | None | 25 | 99.84 | 99.84 |
|  | F68 | 25 | 99.83 | 99.83 |
|  | PS80 | 25 | 99.81 | 99.82 |
| pH 5, 20 mM acetate | None | 50 | 99.82 | 99.83 |
|  | F68 | 50 | 99.82 | 99.82 |
|  | PS80 | 50 | 99.81 | 99.83 |
| pH 5.5, 20 mM His | None | 25 | 99.75 | 99.76 |
|  | F68 | 25 | 99.74 | 99.76 |
|  | PS80 | 25 | 99.76 | 99.77 |
| pH 5.5, 20 mM His | None | 50 | 99.77 | 99.75 |
|  | F68 | 50 | 99.76 | 99.75 |
|  | PS80 | 50 | 99.76 | 99.77 |

There is no appreciable loss of monomer upon agitation, with all formulations exhibiting greater than 99.7% monomer and no significant difference from the quiescent control (Table 8). Adding a surfactant, like Pluronic F-68 or polysorbate 80, does not seem to help or hurt the stability upon agitation.

F/T Study

The second study examining the sensitivity of TRC105 to interfacial stress involved exposure to repeated freeze-thaw cycles. Not only does this provide information on damage at interfaces (like the ice-water interface), it provides essential information on whether TRC105 samples can be frozen for subsequent analysis or during shipping.

TABLE 9

Monomer content by SEC for TRC105 formulations subjected to 0, 3 and 5 F/T cycles.

| Formulation | Surfactant | Protein Mg/ml | 0 cycles | 3 cycles | 5 cycles |
|---|---|---|---|---|---|
| pH 5, 20 mM acetate | None | 25 | 99.86 | 99.83 | 99.82 |
|  | F68 | 25 | 99.84 | 99.81 | 99.82 |
|  | PS80 | 25 | 99.84 | 99.83 | 99.80 |
| pH 5, 20 mM acetate | None | 50 | 99.81 | 99.64 | 99.80 |
|  | F68 | 50 | 99.81 | 99.68 | 99.81 |
|  | PS80 | 50 | 99.82 | 99.65 | 99.80 |
| pH 5.5, 20 mM His | None | 25 | 99.79 | 99.74 | 99.72 |
|  | F68 | 25 | 99.79 | 99.75 | 99.73 |
|  | PS80 | 25 | 99.76 | 99.74 | 99.74 |
| pH 5.5, 20 mM His | None | 50 | 99.76 | 99.79 | 99.75 |
|  | F68 | 50 | 99.75 | 99.82 | 99.73 |
|  | PS80 | 50 | 99.75 | 99.79 | 99.73 |

There is virtually no change in the monomer content upon repeated F/T cycling (Table 9). Surprisingly, adding a surfactant, like Pluronic F-68 or polysorbate 80, did not alter stability upon repeated F/T cycling. Together with the agitation data, there is no indication that TRC105 is surface active to the extent that interfacial damage is a concern. Thus, a surfactant is not needed for a liquid formulation.

SUMMARY

Formulation screening studies were performed on TRC105 at protein concentrations up to 50 mg/ml. This protein is quite stable, showing only small decreases in monomer content by SEC, even after storage at 40° C. for four weeks. No fragmentation was seen at all by SEC. Meanwhile, cIEF analysis showed that only small changes in the overall pI were observed, suggesting that deamidation was minimal across the pH range in question (4.0 to 5.5). There was no evidence for sensitivity to interfacial damage, indicating that a surfactant was not needed in a liquid formulation of TRC105.

The lead formulations employed acetate buffer at pH 4.0 or histidine buffer at pH 5.5, along with sorbitol or trehalose as a tonicity modifier and stabilizer.

Example 10: Long Term Stability Assessment of TRC105 Formulations

A long term stability assessment was performed to verify the results in Study 1 and Study 2. Samples of the formulations presented in Table 10 were stored at 5° C. and 25° C.

TABLE 10

Formulations for verification study

| Formulation Number | Formulation | [protein] |
|---|---|---|
| F01 | pH 5.5, 20 mM histidine, 240 mM trehalose | 25 mg/ml |
| F02 | pH 5.5, 20 mM histidine, 240 mM sorbitol | 25 mg/ml |
| F03 | pH 4.0, 20 mM acetate, 240 mM sorbitol | 25 mg/ml |
| F04 | pH 5.5, 20 mM histidine, 240 mM trehalose | 50 mg/ml |
| F05 | pH 4.0, 20 mM acetate, 240 mM trehalose | 50 mg/ml |
| F06 | pH 5.5, 20 mM histidine, 240 mM trehalose | 100 mg/ml |
| F07 | pH 4.0, 20 mM acetate, 240 mM trehalose | 100 mg/ml |

Results and Discussion

Seven test formulations were evaluated over the course of one year at 5° C. and 6 months at 25° C. At 5° C., all of the formulations performed well. The visual appearances for all samples at all time points in this study were clear and colorless. In general, the pH values remained constant across all of the new formulations for the duration of the study (See Tables 11 and 12). Values were slightly higher than the targets by 0.1 to 0.2 units, but remained stable. Concentration values for new formulations determined by UV remained constant within ~3-4% of the original target values, regardless of the concentration (See Tables 11 and 12). These values did not significantly change over the course of study. There was minimal monomer loss by SEC at 5° C. (See Table 13), and minimal amounts of chemical degradation by cIEF (See Tables 15 and 16). While there was some variability in the CD105 Binding ELISA results, with the exception of the initial results for F05, all values were within the acceptance criterion of 50% to 150% compared to that of a reference standard, which is consistent with the stage of development of the ELISA assay (See Table 17). The results for CE-SDS testing indicated that the samples were comparable to reference material at 5° C. over the course of one year (data not shown).

While samples stored at 5° C. were essentially unchanged, formulation parameters did have an effect on the stability of 25° C. samples. Most notably, formulations containing the acetate buffer system (F03, F05, F07) displayed greater decreases in percent monomer than those containing histidine buffer (F01, F02, F04, and F06) (See Table 14). Meanwhile, changes in protein concentration appear to have little or no effect. The two 100 mg/mL formulations (F06, F07) are comparable to their 50 mg/mL counterparts (F04, F05) in terms of their SEC profiles and cIEF profiles.

TABLE 11 pH and UV concentrations in mg/mL at 5° C.

| Form | Initial pH | Initial conc | 3 Months pH | 3 Months conc | 6 Months pH | 6 Months conc | 12 Months pH | 12 Months conc |
|---|---|---|---|---|---|---|---|---|
| F01 | 5.6 | 25 | 5.6 | 24 | 5.6 | 27 | 5.6 | 24 |
| F02 | 5.6 | 24 | 5.5 | 23 | 5.6 | 25 | 5.6 | 25 |
| F03 | 4.2 | 25 | 4.2 | 25 | 4.3 | 27 | 4.2 | 26 |
| F04 | 5.6 | 50 | 5.6 | 51 | 5.6 | 54 | 5.5 | 52 |
| F05 | 4.2 | 50 | 4.3 | 52 | 4.3 | 54 | 4.2 | 52 |
| F06 | 5.6 | 98 | 5.7 | 99 | 5.7 | 104 | 5.6 | 105 |
| F07 | 4.3 | 99 | 4.4 | 102 | 4.4 | 108 | 4.3 | 102 |

TABLE 12 pH and UV concentrations in mg/mL at 25° C.

| Form | Initial pH | Initial conc | 3 Months pH | 3 Months conc | 6 Months pH | 6 Months conc | 12 Months pH | 12 Months conc |
|---|---|---|---|---|---|---|---|---|
| F01 | n/a | n/a | 5.6 | 25 | 5.6 | 27 | 5.6 | 26 |
| F02 | n/a | n/a | 5.6 | 24 | 5.6 | 25 | 5.6 | 24 |
| F03 | n/a | n/a | 4.3 | 25 | 4.3 | 27 | 4.3 | 26 |
| F04 | n/a | n/a | 5.8 | 50 | 5.6 | 53 | 5.6 | 51 |
| F05 | n/a | n/a | 4.3 | 53 | 4.3 | 53 | 4.3 | 52 |
| F06 | n/a | n/a | 5.7 | 100 | 5.8 | 105 | 5.6 | 105 |
| F07 | n/a | n/a | 4.4 | 109 | 4.5 | 104 | 4.4 | 103 |

TABLE 13

Size Exclusion Chromatography (SEC) at 5° C.

| | % Monomer | | | |
|---|---|---|---|---|
| Form | Initial | 3 Months | 6 Months | 12 Months |
| F01 | 99.36 | 99.36 | 99.38 | 99.37 |
| F02 | 99.37 | 99.37 | 99.34 | 99.37 |
| F03 | 99.37 | 99.35 | 99.31 | 99.24 |
| F04 | 99.35 | 99.33 | 99.32 | 99.31 |
| F05 | 99.38 | 99.35 | 99.31 | 99.24 |
| F06 | 99.24 | 99.22 | 99.19 | 99.18 |
| F07 | 99.35 | 99.29 | 99.23 | 99.17 |

TABLE 14

Size Exclusion Chromatography (SEC) at 25° C.

| | % Monomer | | |
|---|---|---|---|
| Form | Initial | 3 Months | 6 Months |
| F01 | 99.36 | 99.27 | 96.37 |
| F02 | 99.37 | 99.28 | 96.25 |
| F03 | 99.37 | 96.02 | 93.64 |
| F04 | 99.35 | 99.18 | 96.51 |
| F05 | 99.38 | 96.07 | 93.70 |
| F06 | 99.24 | 98.99 | 96.23 |
| F07 | 99.35 | 96.02 | 93.84 |

TABLE 15 cIEF-Average pI at 5° C.

| | Average pI | | | |
|---|---|---|---|---|
| Form | Initial | 3 Months | 6 Months | 12 Months |
| F01 | 9.0 | 8.9 | 9.0 | 9.0 |
| F02 | 8.9 | 8.9 | 8.9 | 9.0 |
| F03 | 8.9 | 8.9 | 9.0 | 9.1 |
| F04 | 8.9 | 8.9 | 8.9 | 9.0 |
| F05 | 8.9 | 8.9 | 8.9 | 9.0 |
| F06 | 8.9 | 8.9 | 8.9 | 9.0 |
| F07 | 8.9 | 8.9 | 8.9 | 9.0 |

TABLE 16 cIEF-Average pI at 25° C.

| | Average pI | | |
|---|---|---|---|
| Form | Initial | 3 Months | 6 Months |
| F01 | 9.0 | 8.9 | 9.0 |
| F02 | 8.9 | 9.0 | 8.9 |
| F03 | 8.9 | 8.9 | 8.9 |
| F04 | 8.9 | 8.9 | 8.9 |
| F05 | 8.9 | 8.9 | 8.8 |
| F06 | 8.9 | 8.9 | 8.9 |
| F07 | 8.9 | 8.9 | 8.9 |

TABLE 17

CD105 Binding ELISA at 5° C.

Percent Relative CD105 Binding Potency

| Form | Initial | 6 Months | 12 Months |
|---|---|---|---|
| F01 | 101 | 94 | 68 |
| F02 | 90 | 90 | 69 |
| F03 | 124 | NT | 77 |
| F04 | 123 | 97 | 74 |
| F05 | 179 | NT | 96 |
| F06 | 93 | 95 | 115 |
| F07 | 100 | NT | 86 |

Example 11: Long Term Stability Assessment of a 4 mg/mL TRC105 Formulation

Stability studies were performed on TRC105 formulated at 4 mg/mL in 17 mM phosphate buffer with 145 mM sodium chloride at pH 7.2 (Lot FIN-0536). Thirty-six months of stability data are available at the recommended storage condition (2-8° C.) and one month of data are available at the accelerated condition of 25° C./60% RH. The stability data is presented in the Tables below. No significant changes were observed for any of the tests performed. Consequently, these studies indicate that TRC105 formulated at 4 mg/mL in 17 mM phosphate buffer with 145 mM sodium chloride at pH 7.2 is stable for at least 36 months when stored at 2-8° C.

TABLE 18

Stability Data for TRC105 Stored at the Recommended Storage Condition of 2-8° C.

| Test | Initial | 6 months | 9 months | 12 months |
|---|---|---|---|---|
| Appearance and Description | Clear colorless solution. Minor grey dust like particulates. | Clear colorless solution with no visible particulates present | Clear colorless solution with minor white particulates present. | Clear colorless solution with minor white particulates present. |
| SDS-PAGE Non-Reduced | Compares to reference | Compares to reference | Compares to reference | Compares to reference |
| SDS-PAGE Reduced | 98% | 96% | 97% | 98% |
| IEF | Compares to reference | Compares to reference | Compares to reference | Compares to reference |
| SEC-HPLC | 96.62% | 96.97 % | 96.91 % | 96.77 % |
| CD105 Binding by ELISA | Binding activity is 88% relative to reference standard | Binding activity is 110% relative to reference standard | Binding activity is 104% relative to reference standard | Binding activity is 91% relative to reference standard |
| UV Absorbance($A_{280}$) | 4.3 mg/mL | 4.2 mg/mL | 4.2 mg/mL | 4.2 mg/mL |
| pH | 7.2 | 7.3 | 7.2 | 7.2 |
| Sterility | Not tested | Not tested | Not tested | Not tested |
| Test | 18 months | 24 months | 30 months | 36 months |
| Appearance and Description | Clear colorless solution with minor white particulates present | Clear colorless solution with no particulates present | Clear colorless solution with no particulates present | Clear colorless solution with no particulates present |
| SDS-PAGE Non-Reduced | Compares to reference | Compares to reference | Compares to reference | Compares to reference |
| SDS-PAGE Reduced | 97% | 96% | 97% | 96% |
| IEF | Compares to reference | Compares to reference | Compares to reference | Compares to reference |
| SEC-HPLC | 96.32 % | 96.86 % | 96.60 % | 94.04% |
| CD105 Binding by ELISA | Binding activity is 88% relative to reference standard | Binding activity is 136% relative to reference standard | Binding activity is 88% relative to reference standard | Binding activity is 105% relative to reference standard |
| UV Absorbance ($A_{280}$) | 4.2 mg/mL | 4.2 mg/mL | 4.2 mg/mL | 4.2 mg/mL |
| pH | 7.2 | 7.2 | 7.2 | 7.3 |
| Sterility | Not tested | Pass | Not tested | Pass |

TABLE 19

Stability Data for Lot FIN-0536 Stored at the Accelerated Storage Condition of 25° C/60% RH

| Test | Initial | 1 month |
| --- | --- | --- |
| Appearance and Description | Clear colorless solution. Minor grey dust like particulates. | Clear colorless solution with no visible particulates present. |
| SDS-PAGE Non-Reduced | Compares to reference | Compares to reference |
| SDS-PAGE Reduced | 98% | 96% |
| IEF | Compares to reference | Compares to reference |
| SEC-HPLC | 96.62% | 96.45% |
| CD105 Binding by ELISA | Binding activity is 88% relative to reference standard | Binding activity is 91% relative to reference standard |
| UV Absorbance($A_{280}$) | 4.3 mg/mL | 4.2 mg/mL |
| pH | 7.2 | 7.3 |

The analytical procedure for SEC-HPLC and UV is the same as that described in Example 9. The analytical procedure for CD105 Binding ELISA is the same as that described in Examplo 3. The analytical procedures for SDS-PAGE Non-Reduced, SDS-PAGE Reduced, and IEF are described below.

SDS-Page of Non-Reduced Proteins and Peptides, Coomassie Stain

Identity and purity are evaluated using polyacrylamide gel electrophoresis analysis. Proteins are separated under denaturing conditions. Pre-cast 4-12% Bis-Tris SDS-containing gels are used. SDS is an anionic detergent, which interacts with proteins to form negatively charged complexes. These complexes migrate through polyacrylamide gels according to their size such that smaller proteins migrate faster than larger proteins. Standards, controls, and test articles are denatured and loaded onto the gel. Following the completion of the run, gels are stained with Coomassie Blue. Gels are scanned using an imaging densitometer.

The relative quantity of each stained band is determined by densitometry for each test article lane. These quantities are expressed as a percentage of the total band quantity obtained for that lane. The molecular weight (kDa) values of the test article bands are determined based on comparison to the molecular weight markers.

SDS-Page of Reduced Proteins, Coomassie Stain

The SDS-PAGE method for reduced proteins is the same as described in Section 1.3.2 (above) for non-reduced samples, with the addition of a reducing step (to cleave the inter- and intra-molecular disulfide bonds to liberate protein subunits as well as other aggregates). To reduce proteins, dithiothreitol (50 mM) is added to samples and references prior to heating at 85° C. for five minutes. Antioxidant is added to the running buffer when reduced proteins are run.

Horizontal Isoelectric Focusing (IEF)

The varying charge on proteins under an applied electric force is exploited to separate proteins. A pH gradient is established between a cathode and an anode, with the cathode at the higher pH value. Since proteins have amphoteric properties, they will possess a positively charged value below their pI and a negatively charged value above their pI. Under the influence of an electrical force a pH gradient is established and the proteins will migrate and focus at their isoelectric point. The procedure involves the use of isoelectric focusing of protein samples using pre-cast gels in a horizontal format. Following electrophoresis, the gels are Coomassie-stained. The area of each band is determined by densitometry for each sample lane. The area of the bands is calculated as a percentage of the total band area. The pI and Rf values are also determined for each band.

Example 12: Clinical Trial for Colorectal Cancer

This example describes a randomized, blinded, placebo-controlled, multicenter, Phase II study designed to provide a preliminary assessment of the safety and efficacy of anti-CD105 antibody in patients with colorectal cancer. Approximately about 100 to about 800 patients are enrolled, with about 50 to about 400 patients being assigned to a treatment group from about 50 to about 400 patients assigned to a placebo group. The trial will consist of the administration of intravenous repeating doses of anti-CD105 antibody at about 0.1 to about 10 mg/kg or placebo every two weeks for 6-10 cycles. Chemotherapy may be used in all groups. A VEGF inhibitor may be used in all groups. The time frame of the study is estimated at about 6 months-about 5 years, with continued therapy for responders as indicated at the end of the initial study. Additional outcome measures are as follows:

Primary outcome measure: overall response rate. One goal of the study is to demonstrate an increase overall response rate from treatment with anti-CD105 antibody as compared to the control IgG.

Secondary outcome measures that can be assessed include duration of response, time to tumor progression, overall survival, serious and non-serious adverse events. For example, a treatment may prevent progression of the disease (i.e., stasis) or may result in an improvement. Alternately, or in addition, other goals can be measured with respect to one or more of the following: decreased tumor burden, decreased neovascularization, reduced side effects, decreased adverse reactions, and/or increased patient compliance.

Example 13: Clinical Trial for Kidney Cancer

This example describes a randomized, blinded, placebo-controlled, multicenter, Phase II study designed to provide a preliminary assessment of the safety and efficacy of anti-CD105 antibody in patients with renal cell cancer (kidney cancer). Approximately about 100 to about 800 patients are enrolled, with about 50-about 400 patients being assigned to a treatment group and about 50-about 400 patients assigned to a placebo group. The trial will consist of the administration of intravenous repeating doses of anti-CD105 antibody at about 0.1-about 30 mg/kg or placebo every one to three weeks for 3-6 cycles or until progression. Interferon may also be used in both treatment arms. A VEGF inhibitor may be used in both treatment arms. The time frame of the study is estimated at about 6 months-about 5 years, with continued therapy for responders as indicated at the end of the initial study. Additional outcome measures are as follows:

Primary outcome measure: progression-free survival. One goal of the study is to demonstrate an increase in progression free survival following treatment with anti-CD105 antibody as compared to the placebo.

Secondary outcome measures that can be assessed include duration of response, time to tumor progression, overall survival, serious and non-serious adverse events. For example, a treatment may prevent progression of the disease (i.e., stasis) or may result in an improvement. Alternately, or in addition, other goals can be measured with respect to one or more of the following: decreased tumor burden, decreased neovascularization, reduced side effects, decreased adverse reactions, and/or increased patient compliance.

Example 14: Clinical Trial for Hepatocellular Cancer

This example describes a randomized, blinded, placebo-controlled, multicenter, Phase II study designed to provide a preliminary assessment of the safety and efficacy of anti-CD105 antibody in patients with hepatocellular cancer (liver cancer). Approximately about 100 to about 800 patients are enrolled, with about 50 to about 400 patients being assigned to a treatment group from about 50 to about 400 patients assigned to a placebo group. A VEGF inhibitor may be used in both groups. The trial will consist of the administration of intravenous repeating doses of anti-CD105 antibody at about 0.1 to about 30 mg/kg or placebo every one to three weeks or until progression. The time frame of the study is estimated at about 6 months to about 5 years, with continued therapy for responders as indicated at the end of the initial study. Additional outcome measures are as follows:

Primary Outcome Measures: Progression-free survival. One goal of the study is to demonstrate an increase in progression free survival following treatment with anti-CD105 antibody as compared to the placebo.

Secondary outcome measures that can be assessed include duration of response, time to tumor progression, overall survival, serious and non-serious adverse events. For example, a treatment may prevent progression of the disease (i.e., stasis) or may result in an improvement. Alternately, or in addition, other goals can be measured with respect to one or more of the following: decreased tumor burden, decreased neovascularization, reduced side effects, decreased adverse reactions, and/or increased patient compliance.

Example 15: Clinical Trial for Ovarian Cancer

This example describes a randomized, blinded, placebo-controlled, multicenter, Phase II study designed to provide a preliminary assessment of the safety and efficacy of anti-CD105 antibody in patients with ovarian cancer. Approximately about 100 to about 800 patients are enrolled, with about 50 to about 400 patients being assigned to a treatment group from about 50 to about 400 patients assigned to a placebo group. The trial will consist of the administration of intravenous repeating doses of anti-CD105 antibody at about 0.1 to about 30 mg/kg or placebo every one to three weeks for 5 cycles. Chemotherapy may also be used in both treatment arms. A VEGF inhibitor may be used in both treatment arms. The time frame of the study is estimated at 6 months to about 5 years, with continued therapy for responders as indicated at the end of the initial study. Additional outcome measures are as follows:

Primary Outcome Measure: Progression-free survival. One goal of the study is to demonstrate an increase in progression free survival following treatment with anti-CD105 antibody as compared to the placebo.

Secondary outcome measures that can be assessed include duration of response, time to tumor progression, overall survival, serious and non-serious adverse events. For example, a treatment may prevent progression of the disease (i.e., stasis) or may result in an improvement. Alternately, or in addition, other goals can be measured with respect to one or more of the following: decreased tumor burden, decreased neovascularization, reduced side effects, decreased adverse reactions, and/or increased patient compliance.

Example 16: Treatment of Age-Related Macular Degeneration

First Study

Patients manifesting age-related macular degeneration are treated with an intravitreal injection of anti-CD105 antibody or control antibody to reduce or prevent the development of neovascularization, macular disease, and retinal damage.

As the first step of treatment, the patients are to receive a full ophthalmic examination to establish a baseline of ocular health. The ophthalmic examination includes indirect ophthalmoscopy, slit-lamp biomicroscopy, peripheral retinal examination, intraocular pressure measurements, visual acuity (unaided and best corrected) symptomatology, fundus photography, fluorescein angiography, optical coherence tomography, electroretinography and A-scan measurements.

Following the preliminary examination, an intravitreal injection as described above is given to a patient's affected eye manifesting AMD. If both eyes are affected, they may be treated separately. The eye to be treated is injected with an ophthalmic solution.

After treatment, the patients' eyes are to be examined on days one (1), two (2), seven (7), fifteen (15), thirty (30) and sixty (60) and every month thereafter for 2 years. Because of the possibility of reoccurrence, the patients should return for periodic examinations on a monthly basis thereafter. On each examination day the patient is monitored for vitreous liquefaction. Additionally, the patients are monitored for posterior vitreous detachments using indirect ophthalmoscopy with scleral depression. Finally, the extent of AMD presented by the patients is continuously monitored through periodic retinal examinations, optical coherence tomography and fluorescein angiograms to monitor for the presence of subretinal fluid, blood, exudates, RPE detachment, cystic retinal changes, or the presence of grayish green subretinal neovascular membrane. Additional treatments may be required if indicia of reoccurring neovascularization are observed. Additional treatments may be given on weekly or monthly basis. In a preferred embodiment, an initial treatment is followed by subsequent treatments between 1 to 6 months apart.

Second Study

Purpose: To demonstrate the efficacy of intravitreal anti-CD105 antibodies for treatment of neovascular age-related macular degeneration (AMD). A VEGF inhibitor may be used in all patients.

Methods: Fifty to 500 patients (50 to 500 eyes) with subfoveal choroidal neovascularization (CNV) resulting from AMD will participated in the study at an approved site.

The criteria for reinjection are presence of fluid in the macula, increased central retinal thickness (CRT) of at least 100 micron, loss of at least 5 letters of vision associated with increased fluid in the macula, new classic CNV, or new macular hemorrhage. The main outcome measure is the proportion of eyes losing fewer than 15 letters of vision after 12 months. Best-corrected visual acuity measurement and clinical ocular examination are performed at 1 week, 1 month and then monthly for 5-12 months.

Mean visual acuity and mean CRT are measured compared to baseline. Ocular and/or systemic side effects are noted.

Example 17: Humanized-Deimmunized Antibody Sequences

An isolated humanized, de-immunized anti-CD105 antibody can comprise a heavy chain variable region having the amino acid sequence set forth as SEQ ID NO: 11 and a light chain variable region having the amino acid sequence set forth as SEQ ID NO: 12.

```
SEQ ID NO: 11:
Glu Val Gln Leu Val Glu Ser Gly Gly Gly Leu Val
Lys Pro Gly Gly Ser Leu Arg Leu Ser Cys Ala Ala
Ser Gly Phe Thr Phe Ser Asp Ala Trp Met Asp Trp
Val Arg Gln Ala Pro Gly Lys Gly Leu Glu Trp Val
Gly Glu Ala Arg Ser Lys Ala Ser Asn His Ala Thr
Tyr Tyr Ala Glu Ser Val Lys Gly Arg Phe Thr Ile
Ser Arg Asp Asp Ser Lys Asn Thr Leu Tyr Leu Gln
Met Asn Ser Leu Lys Thr Glu Asp Thr Ala Val Tyr
Tyr Cys Thr Arg Trp Arg Arg Phe Phe Asp Ser Trp
Gly Gln Gly Thr Leu Val Thr Val Ser Ser

SEQ ID NO: 12:
Asp Ile Gln Met Thr Gln Ser Pro Ser Ser Leu Ser
Ala Ser Val Gly Asp Arg Ala Thr Ile Thr Cys Arg
Ala Ser Ser Ser Val Ser Tyr Met His Trp Tyr Gln
Gln Lys Pro Gly Lys Ala Pro Lys Pro Trp Ala Tyr
Ala Thr Ser Asn Leu Ala Ser Gly Val Pro Ser Arg
Phe Ser Gly Ser Gly Ser Gly Thr Asp Tyr Thr Leu
Thr Ile Ser Ser Leu Gln Pro Glu Asp Phe Ala Thr
Tyr Tyr Cys Gln Gln Trp Ser Ser Asn Pro Leu Thr
Phe Gly Gly Gly Thr Lys Val Glu Ile Lys
```

Other non-limiting examples of humanized-deimmunized heavy chains include, but are not limited to, SEQ ID NOS: 13, 14, 15 and 16.

```
SEQ ID NO: 13:
Glu Val Gln Leu Val Glu Ser Gly Gly Gly Leu Val
Lys Pro Gly Gly Ser Leu Arg Leu Ser Cys Ala Ala
Ser Gly Phe Thr Phe Ser Asp Ala Trp Met Asp Trp
Val Arg Gln Ala Pro Gly Lys Gly Leu Glu Trp Val
Ala Glu Ile Arg Ser Lys Ala Ser Asn His Ala Thr
Tyr Tyr Ala Glu Ser Val Lys Gly Arg Phe Thr Ile
Ser Arg Asp Asp Ser Lys Asn Thr Leu Tyr Leu Gln
Met Asn Ser Leu Lys Thr Glu Asp Thr Ala Val Tyr
Tyr Cys Thr Arg Trp Arg Arg Phe Phe Asp Ser Trp
Gly Gln Gly Thr Leu Val Thr Val Ser Ser

SEQ ID NO: 14:
Glu Val Gln Leu Val Glu Ser Gly Gly Gly Leu Val
Lys Pro Gly Gly Ser Leu Arg Leu Ser Cys Ala Ala
Ser Gly Phe Thr Phe Ser Asp Ala Trp Met Asp Trp
Val Arg Gln Ala Pro Gly Lys Gly Leu Glu Trp Val
Gly Glu Ile Arg Ser Gln Ala Ser Asn His Ala Thr
Tyr Tyr Ala Glu Ser Val Lys Gly Arg Phe Thr Ile
Ser Arg Asp Asp Ser Lys Asn Thr Leu Tyr Leu Gln
Met Asn Ser Leu Lys Thr Glu Asp Thr Ala Val Tyr
Tyr Cys Thr Arg Trp Arg Arg Phe Phe Asp Ser Trp
Gly Gln Gly Thr Leu Val Thr Val Ser Ser

SEQ ID NO: 15:
Glu Val Gln Leu Val Glu Ser Gly Gly Gly Leu Val
Lys Pro Gly Gly Ser Leu Arg Leu Ser Cys Ala Ala
Ser Gly Phe Thr Phe Ser Asp Ala Trp Met Asp Trp
Val Arg Gln Ala Pro Gly Lys Gly Leu Glu Trp Val
Gly Glu Ile Arg Ser Arg Ala Ser Asn His Ala Thr
Tyr Tyr Ala Glu Ser Val Lys Gly Arg Phe Thr Ile
Ser Arg Asp Asp Ser Lys Asn Thr Leu Tyr Leu Gln
Met Asn Ser Leu Lys Thr Glu Asp Thr Ala Val Tyr
Tyr Cys Thr Arg Trp Arg Arg Phe Phe Asp Ser Trp
Gly Gln Gly Thr Leu Val Thr Val Ser Ser

SEQ ID NO: 16:
Glu Val Gln Leu Val Glu Ser Gly Gly Gly Leu Val
Lys Pro Gly Gly Ser Leu Arg Leu Ser Cys Ala Ala
Ser Gly Phe Thr Phe Ser Asp Ala Trp Met Asp Trp
Val Arg Gln Ala Pro Gly Lys Gly Leu Glu Trp Val
Ser Glu Ile Arg Ser Lys Ala Ser Asn His Ala Thr
Tyr Tyr Ala Glu Ser Val Lys Gly Arg Phe Thr Ile
Ser Arg Asp Asp Ser Lys Asn Thr Leu Tyr Leu Gln
Met Asn Ser Leu Lys Thr Glu Asp Thr Ala Val Tyr
Tyr Cys Thr Arg Trp Arg Arg Phe Phe Asp Ser Trp
Gly Gln Gly Thr Leu Val Thr Val Ser Ser
```

Other non-limiting examples of humanized-deimmunized light chains include, but are not limited to, SEQ ID NOS: 17, 18, 19, 20, 21, 22, and 23.

```
SEQ ID NO: 17:
Asp Ile Gln Leu Thr Gln Ser Pro Ser Ser Leu Ser
Ala Ser Val Gly Asp Arg Ala Thr Ile Thr Cys Arg
Ala Ser Ser Ser Val Ser Tyr Met His Trp Tyr Gln
```

Gln Lys Pro Gly Lys Ala Pro Lys Pro Trp Ala Tyr

Ala Thr Ser Asn Leu Ala Ser Gly Val Pro Ser Arg

Phe Ser Gly Ser Gly Ser Gly Thr Asp Tyr Thr Leu

Thr Ile Ser Ser Leu Gln Pro Glu Asp Phe Ala Thr

Tyr Tyr Cys Gln Gln Trp Ser Ser Asn Pro Leu Thr

Phe Gly Gly Gly Thr Lys Val Glu Ile Lys

SEQ ID NO: 18:
Asp Ile Gln Leu Thr Gln Ser Pro Ser Ser Leu Ser

Ala Ser Val Gly Asp Arg Ala Thr Ile Thr Cys Arg

Ala Ser Ser Val Ser Tyr Met His Trp Tyr Gln

Gln Lys Pro Gly Lys Ala Pro Lys Pro Trp Ile Tyr

Ala Ser Ser Asn Leu Ala Ser Gly Val Pro Ser Arg

Phe Ser Gly Ser Gly Ser Gly Thr Asp Tyr Thr Leu

Thr Ile Ser Ser Leu Gln Pro Glu Asp Phe Ala Thr

Tyr Tyr Cys Gln Gln Trp Ser Ser Asn Pro Leu Thr

Phe Gly Gly Gly Thr Lys Val Glu Ile Lys

SEQ ID NO: 19:
Asp Ile Gln Leu Thr Gln Ser Pro Ser Ser Leu Ser

Ala Ser Val Gly Asp Arg Val Thr Ile Ser Cys Arg

Ala Ser Ser Val Ser Tyr Met His Trp Tyr Gln

Gln Lys Pro Gly Lys Ala Pro Lys Pro Trp Ala Tyr

Ala Thr Ser Asn Leu Ala Ser Gly Val Pro Ser Arg

Phe Ser Gly Ser Gly Ser Gly Thr Asp Tyr Thr Leu

Thr Ile Ser Ser Leu Gln Pro Glu Asp Phe Ala Thr

Tyr Tyr Cys Gln Gln Trp Ser Ser Asn Pro Leu Thr

Phe Gly Gly Gly Thr Lys Val Glu Ile Lys

SEQ ID NO: 20:
Asp Ile Gln Leu Thr Gln Ser Pro Ser Ser Leu Ser

Ala Ser Val Gly Asp Arg Val Thr Ile Ser Cys Arg

Ala Ser Ser Val Ser Tyr Met His Trp Tyr Gln

Gln Lys Pro Gly Lys Ala Pro Lys Pro Trp Ile Tyr

Ala Ser Ser Asn Leu Ala Ser Gly Val Pro Ser Arg

Phe Ser Gly Ser Gly Ser Gly Thr Asp Tyr Thr Leu

Thr Ile Ser Ser Leu Gln Pro Glu Asp Phe Ala Thr

Tyr Tyr Cys Gln Gln Trp Ser Ser Asn Pro Leu Thr

Phe Gly Gly Gly Thr Lys Val Glu Ile Lys

SEQ ID NO: 21:
Asp Ile Gln Met Thr Gln Ser Pro Ser Ser Leu Ser

Ala Ser Val Gly Asp Arg Val Thr Ile Ser Cys Arg

Ala Ser Ser Val Ser Tyr Met His Trp Tyr Gln

Gln Lys Pro Gly Lys Ala Pro Lys Pro Trp Ile Tyr

Ala Ser Ser Asn Leu Ala Ser Gly Val Pro Ser Arg

Phe Ser Gly Ser Gly Ser Gly Thr Asp Tyr Thr Leu

Thr Ile Ser Ser Leu Gln Pro Glu Asp Phe Ala Thr

Tyr Tyr Cys Gln Gln Trp Ser Ser Asn Pro Leu Thr

Phe Gly Gly Gly Thr Lys Val Glu Ile Lys

SEQ ID NO: 22:
Asp Ile Gln Met Thr Gln Ser Pro Ser Ser Leu Ser

Ala Ser Val Gly Asp Arg Ala Thr Ile Thr Cys Arg

Ala Ser Ser Val Ser Tyr Met His Trp Tyr Gln

Gln Lys Pro Gly Lys Ala Pro Lys Pro Trp Ile Tyr

Ala Ser Ser Asn Leu Ala Ser Gly Val Pro Ser Arg

Phe Ser Gly Ser Gly Ser Gly Thr Asp Tyr Thr Leu

Thr Ile Ser Ser Leu Gln Pro Glu Asp Phe Ala Thr

Tyr Tyr Cys Gln Gln Trp Ser Ser Asn Pro Leu Thr

Phe Gly Gly Gly Thr Lys Val Glu Ile Lys

SEQ ID NO: 23:
Asp Ile Gln Met Thr Gln Ser Pro Ser Ser Leu Ser

Ala Ser Val Gly Asp Arg Val Thr Ile Ser Cys Arg

Ala Ser Ser Val Ser Tyr Met His Trp Tyr Gln

Gln Lys Pro Gly Lys Ala Pro Lys Pro Trp Ala Tyr

Ala Thr Ser Asn Leu Ala Ser Gly Val Pro Ser Arg

Phe Ser Gly Ser Gly Ser Gly Thr Asp Tyr Thr Leu

Thr Ile Ser Ser Leu Gln Pro Glu Asp Phe Ala Thr

Tyr Tyr Cys Gln Gln Trp Ser Ser Asn Pro Leu Thr

Phe Gly Gly Gly Thr Lys Val Glu Ile Lys

Aspects of the embodiments described herein may be embodied in other forms or carried out in other ways without departing from the spirit or essential characteristics thereof. The present disclosure is therefore to be considered as in all aspects illustrated and not restrictive, and all changes which come within the meaning and range of equivalency are intended to be embraced therein.

What is claimed is:

1. A formulation that comprises from about 1 mg/ml to about 150 mg/ml of an anti-CD105 antibody, or an antigen-binding fragment thereof; from about 10 mM to about 20 mM of a buffering agent; from about 120 mM to about 240 mM of a polyol; and a pH of about 4.0; wherein the buffering agent comprises acetate.

2. The formulation of claim 1, wherein the average isoelectric point (pI) of the anti-CD105 antibody, or the antigen-binding fragment thereof, is from about 8.7 to about 9.2 after storage at 2 to 8° C. for at least 12 months, as measured by capillary electrophoresis-isoelectric focusing.

3. The formulation of claim 1, wherein the anti-CD105 antibody comprises a light chain variable region ($V_L$) having the amino acid sequence set forth as SEQ ID NO: 1; a light chain constant region having the amino acid sequence set forth as SEQ ID NO: 2; a heavy chain variable region ($V_H$) having the amino acid sequence set forth as SEQ ID NO: 3; and a constant region having the amino acid sequence set forth as SEQ ID NO: 4.

4. The formulation of claim 1, wherein the anti-CD105 antibody, or the antigen-binding fragment thereof, comprises a $V_L$ CDR1 having the amino acid sequence set forth as SEQ ID NO: 5; a $V_L$ CDR2 having the amino acid sequence set forth as SEQ ID NO: 6; a $V_L$ CDR3 having the amino acid sequence set forth as SEQ ID NO: 7; a $V_H$ CDR1 having the amino acid sequence set forth as SEQ ID NO: 8; a $V_H$ CDR2 having the amino acid sequence set forth as SEQ ID NO: 9; and a $V_H$ CDR3 having the amino acid sequence set forth as SEQ ID NO: 10.

5. The formulation of claim 1, that comprises about 25 mg/ml, about 50 mg/ml, or about 100 mg/ml of the anti-CD105 antibody or the antigen-binding fragment thereof.

6. The formulation of claim 1, that comprises about 10 mM or about 20 mM acetate.

7. The formulation of claim 1, wherein the formulation is formulated for intravitreal or intravenous administration.

8. The formulation of claim 1, that further comprises an acceptable carrier or excipient.

9. The formulation of claim 1, which is isotonic or hypertonic.

10. The formulation of claim 1, wherein the formulation is made isotonic with a salt.

11. The formulation of claim 1, wherein the polyol comprises a sugar.

12. The formulation of claim 11, wherein the sugar comprises a non-reducing sugar.

13. The formulation of claim 12, wherein the non-reducing sugar comprises trehalose or sucrose.

14. The formulation of claim 11, wherein the sugar comprises sorbitol.

15. The formulation of claim 1, that further comprises a surfactant.

16. A pre-filled syringe suitable for intravenous or intravitreal administration that comprises the formulation of claim 1.

17. The formulation of claim 1, wherein the pH of the formulation is 4.0±0.1.

18. The formulation of claim 1, wherein the anti-CD105 antibody, or antigen binding fragment thereof, comprises a light chain variable region ($V_L$) having the amino acid sequence set forth as SEQ ID NO: 1; and a heavy chain variable region ($V_H$) having the amino acid sequence set forth as SEQ ID NO: 3.

19. The formulation of claim 1, wherein the pH of the formulation is from 3.8 to 4.2.

20. The formulation of claim 1, wherein the pH of the formulation is 3.8, 3.9, 4.0, 4.1, or 4.2.

21. A formulation that comprises from about 25 mg/ml to about 150 mg/ml of an anti-CD105 antibody, or antigen-binding fragment thereof; from about 10 mM to about 20 mM of a buffering agent; from about 10 mM to about 20 mM of a buffering agent; from about 120 mM to about 240 mM of a polyol; and a pH of 4.0±0.2; wherein the buffering agent comprises acetate and the polyol comprises trehalose or sorbitol.

22. The formulation of claim 21, wherein the pH of the formulation is from 3.9 to 4.1.

23. The formulation of claim 21, wherein the pH of the formulation is 4.0.

24. The formulation of claim 21, wherein the formulation is formulated for intravitreal administration.

25. The formulation of claim 21, wherein the formulation is formulated for intravenous administration.

26. A prefilled syringe that comprises the formulation of claim 21.

27. The formulation of claim 15, wherein the surfactant comprises polysorbate 20 or polysorbate 80.

28. The formulation of claim 15, wherein the surfactant is present in the formulation in an amount of about 0.1% or about 0.005%.

29. The formulation of claim 21, wherein the formulation further comprises a surfactant.

30. The formulation of claim 29, wherein the surfactant comprises polysorbate 20 or polysorbate 80.

31. The formulation of claim 30, wherein the surfactant is present in the formulation in an amount of about 0.1% or about 0.005%.

32. The formulation of claim 21, that further comprises an acceptable carrier or excipient.

33. The formulation of claim 1, that comprises about 10 mM or about 20 mM of the buffering agent.

34. The formulation of claim 21, that comprises about 10 mM or about 20 mM of the buffering agent.

35. The formulation of claim 1, that comprises about 120 mM or about 240 mM of the polyol.

36. The formulation of claim 21, that comprises about 120 mM or about 240 mM of the polyol.

* * * * *

SEQUENCE LISTING

<160> NUMBER OF SEQ ID NOS: 23

<210> SEQ ID NO 1
<211> LENGTH: 106
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 1

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Val Ser Tyr Met
            20                  25                  30

His Trp Tyr Gln Gln Lys Pro Gly Ser Ser Pro Lys Pro Trp Ile Tyr
        35                  40                  45

Ala Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu Leu Lys
            100                 105

<210> SEQ ID NO 2
<211> LENGTH: 107
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 2

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 3
<211> LENGTH: 118
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 3

Glu Val Lys Leu Glu Glu Ser Gly Gly Gly Leu Val Gln Pro Gly Gly
1               5                   10                  15

Ser Met Lys Leu Ser Cys Ala Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Ser Lys Ala Ser Asn His Ala Thr Tyr Tyr Ala Glu

```
                50                  55                  60
Ser Val Lys Gly Arg Phe Thr Ile Ser Arg Asp Asp Ser Lys Ser Ser
 65                  70                  75                  80

Val Tyr Leu Gln Met Asn Ser Leu Arg Ala Glu Asp Thr Gly Ile Tyr
                 85                  90                  95

Tyr Cys Thr Arg Trp Arg Arg Phe Phe Asp Ser Trp Gly Gln Gly Thr
                100                 105                 110

Thr Leu Thr Val Ser Ser
            115

<210> SEQ ID NO 4
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285
```

```
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Ala Ser Ser Ser Val Ser Tyr Met His
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Thr Ser Asn Leu Ala Ser
1               5

<210> SEQ ID NO 7
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Gln Trp Ser Ser Asn Pro Leu Thr
1               5

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Ala Trp Met Asp
1               5

<210> SEQ ID NO 9
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Glu Ile Arg Ser Lys Ala Ser Asn His Ala Thr Tyr Tyr Ala Glu Ser
1               5                   10                  15
```

Val Lys Gly

<210> SEQ ID NO 10
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Trp Arg Arg Phe Phe Asp Ser
1               5

<210> SEQ ID NO 11
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Gly Glu Ala Arg Ser Lys Ala Ser Asn His Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Arg Trp Arg Arg Phe Phe Asp Ser Trp Gly Gln Gly Thr
            100                 105                 110

Leu Val Thr Val Ser Ser
        115

<210> SEQ ID NO 12
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Asp Ile Gln Met Thr Gln Ser Pro Ser Ser Leu Ser Ala Ser Val Gly
1               5                   10                  15

Asp Arg Ala Thr Ile Thr Cys Arg Ala Ser Ser Ser Val Ser Tyr Met
            20                  25                  30

His Trp Tyr Gln Gln Lys Pro Gly Lys Ala Pro Lys Pro Trp Ala Tyr
        35                  40                  45

Ala Thr Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

```
Phe Gly Gly Gly Thr Lys Val Glu Ile Lys
            100                 105
```

```
<210> SEQ ID NO 13
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Ala Glu Ile Arg Ser Lys Ala Ser Asn His Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Arg Trp Arg Arg Phe Phe Asp Ser Trp Gly Gln Gly Thr
            100                 105                 110

Leu Val Thr Val Ser Ser
        115
```

```
<210> SEQ ID NO 14
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Gly Glu Ile Arg Ser Gln Ala Ser Asn His Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Arg Trp Arg Arg Phe Phe Asp Ser Trp Gly Gln Gly Thr
            100                 105                 110

Leu Val Thr Val Ser Ser
        115
```

```
<210> SEQ ID NO 15
<211> LENGTH: 118
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 15

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Gly Glu Ile Arg Ser Arg Ala Ser Asn His Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Arg Trp Arg Arg Phe Phe Asp Ser Trp Gly Gln Gly Thr
            100                 105                 110

Leu Val Thr Val Ser Ser
            115

<210> SEQ ID NO 16
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Ala
            20                  25                  30

Trp Met Asp Trp Val Arg Gln Ala Pro Gly Lys Gly Leu Glu Trp Val
        35                  40                  45

Ser Glu Ile Arg Ser Lys Ala Ser Asn His Ala Thr Tyr Tyr Ala Glu
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Arg Trp Arg Arg Phe Phe Asp Ser Trp Gly Gln Gly Thr
            100                 105                 110

Leu Val Thr Val Ser Ser
            115

<210> SEQ ID NO 17
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Asp Ile Gln Leu Thr Gln Ser Pro Ser Ser Leu Ser Ala Ser Val Gly
1               5                   10                  15

```
Asp Arg Ala Thr Ile Thr Cys Arg Ala Ser Ser Val Ser Tyr Met
            20                  25                  30

His Trp Tyr Gln Gln Lys Pro Gly Lys Ala Pro Lys Pro Trp Ala Tyr
            35                  40                  45

Ala Thr Ser Asn Leu Ala Ser Gly Val Pro Ser Arg Phe Ser Gly Ser
50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 18
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Ile Gln Leu Thr Gln Ser Pro Ser Ser Leu Ser Ala Ser Val Gly
1               5                   10                  15

Asp Arg Ala Thr Ile Thr Cys Arg Ala Ser Ser Val Ser Tyr Met
            20                  25                  30

His Trp Tyr Gln Gln Lys Pro Gly Lys Ala Pro Lys Pro Trp Ile Tyr
            35                  40                  45

Ala Ser Ser Asn Leu Ala Ser Gly Val Pro Ser Arg Phe Ser Gly Ser
50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 19
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Asp Ile Gln Leu Thr Gln Ser Pro Ser Ser Leu Ser Ala Ser Val Gly
1               5                   10                  15

Asp Arg Val Thr Ile Ser Cys Arg Ala Ser Ser Val Ser Tyr Met
            20                  25                  30

His Trp Tyr Gln Gln Lys Pro Gly Lys Ala Pro Lys Pro Trp Ala Tyr
            35                  40                  45

Ala Thr Ser Asn Leu Ala Ser Gly Val Pro Ser Arg Phe Ser Gly Ser
50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95
```

Phe Gly Gly Gly Thr Lys Val Glu Ile Lys
            100                 105

<210> SEQ ID NO 20
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Gln Leu Thr Gln Ser Pro Ser Ser Leu Ser Ala Ser Val Gly
1               5                   10                  15

Asp Arg Val Thr Ile Ser Cys Arg Ala Ser Ser Ser Val Ser Tyr Met
            20                  25                  30

His Trp Tyr Gln Gln Lys Pro Gly Lys Ala Pro Lys Pro Trp Ile Tyr
        35                  40                  45

Ala Ser Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 21
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Asp Ile Gln Met Thr Gln Ser Pro Ser Ser Leu Ser Ala Ser Val Gly
1               5                   10                  15

Asp Arg Val Thr Ile Ser Cys Arg Ala Ser Ser Ser Val Ser Tyr Met
            20                  25                  30

His Trp Tyr Gln Gln Lys Pro Gly Lys Ala Pro Lys Pro Trp Ile Tyr
        35                  40                  45

Ala Ser Ser Asn Leu Ala Ser Gly Val Pro Ser Arg Phe Ser Gly Ser
    50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 22
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Asp Ile Gln Met Thr Gln Ser Pro Ser Ser Leu Ser Ala Ser Val Gly

```
                                  -continued
1               5                   10                  15

Asp Arg Ala Thr Ile Thr Cys Arg Ala Ser Ser Ser Val Ser Tyr Met
                20                  25                  30

His Trp Tyr Gln Gln Lys Pro Gly Lys Ala Pro Lys Pro Trp Ile Tyr
            35                  40                  45

Ala Ser Ser Asn Leu Ala Ser Gly Val Pro Ser Arg Phe Ser Gly Ser
        50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Val Glu Ile Lys
            100                 105

<210> SEQ ID NO 23
<211> LENGTH: 106
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Ile Gln Met Thr Gln Ser Pro Ser Ser Leu Ser Ala Ser Val Gly
1               5                   10                  15

Asp Arg Val Thr Ile Ser Cys Arg Ala Ser Ser Ser Val Ser Tyr Met
                20                  25                  30

His Trp Tyr Gln Gln Lys Pro Gly Lys Ala Pro Lys Pro Trp Ala Tyr
            35                  40                  45

Ala Thr Ser Asn Leu Ala Ser Gly Val Pro Ser Arg Phe Ser Gly Ser
        50                  55                  60

Gly Ser Gly Thr Asp Tyr Thr Leu Thr Ile Ser Ser Leu Gln Pro Glu
65                  70                  75                  80

Asp Phe Ala Thr Tyr Tyr Cys Gln Gln Trp Ser Ser Asn Pro Leu Thr
                85                  90                  95

Phe Gly Gly Gly Thr Lys Val Glu Ile Lys
            100                 105
```